(12) United States Patent
Bremer et al.

(10) Patent No.: US 11,261,163 B2
(45) Date of Patent: Mar. 1, 2022

(54) CYANOPYRIMIDINE DERIVATIVES

(71) Applicant: Merck Patent GmbH, Darmstadt (DE)

(72) Inventors: Matthias Bremer, Darmstadt (DE); Atsutaka Manabe, Bensheim (DE)

(73) Assignee: Merck Patent GmbH, Darmstadt (DE)

( * ) Notice: Subject to any disclaimer, the term of this patent is extended or adjusted under 35 U.S.C. 154(b) by 352 days.

(21) Appl. No.: 16/087,354

(22) PCT Filed: Mar. 22, 2017

(86) PCT No.: PCT/EP2017/056754
§ 371 (c)(1),
(2) Date: Sep. 21, 2018

(87) PCT Pub. No.: WO2017/162707
PCT Pub. Date: Sep. 28, 2017

(65) Prior Publication Data
US 2020/0262795 A1    Aug. 20, 2020

(30) Foreign Application Priority Data
Mar. 24, 2016 (EP) ..................................... 16162306

(51) Int. Cl.
*C09K 19/06* (2006.01)
*C07D 239/26* (2006.01)
*C09K 19/18* (2006.01)
*C09K 19/32* (2006.01)
*C09K 19/34* (2006.01)

(52) U.S. Cl.
CPC ............ *C07D 239/26* (2013.01); *C09K 19/18* (2013.01); *C09K 19/322* (2013.01); *C09K 19/3458* (2013.01); *C09K 2019/181* (2013.01)

(58) Field of Classification Search
CPC .. C09K 19/18; C09K 19/322; C09K 19/3458; C09K 2019/181; C09K 2019/3422; C07D 239/26
USPC ................................................... 252/299.61
See application file for complete search history.

(56) References Cited

U.S. PATENT DOCUMENTS

| 5,454,975 A | 10/1995 | Reiffenrath et al. |
| 9,822,305 B2 * | 11/2017 | Wittek .............. C09K 19/3458 |
| 9,938,462 B2 | 4/2018 | Manabe et al. |
| 2015/0322344 A1 | 11/2015 | Manabe et al. |

FOREIGN PATENT DOCUMENTS

| DE | 4409431 A1 | 10/1994 |
| DE | 4410606 A1 | 10/1994 |
| WO | 2014/094973 A1 | 6/2014 |

OTHER PUBLICATIONS

International Search Report dated May 3, 2017 issued in corresponding PCT/EP2017/056754 application (4 pages).
English Abstract of DE 4410606 A1 published Oct. 6, 1994.

* cited by examiner

*Primary Examiner* — Geraldina Visconti
(74) *Attorney, Agent, or Firm* — Millen, White, Zelano and Branigan, P.C.; Harry B. Shubin

(57) ABSTRACT

The present invention relates to compounds of formula M

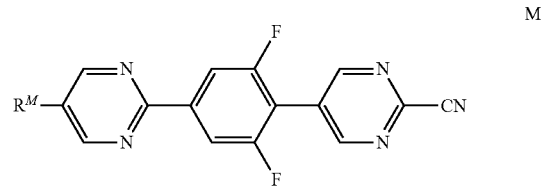

in which $R^M$ has the meaning indicated in claim 1, to liquid crystal mixture comprising the same, to the use of these liquid-crystal media, in particular in components for high-frequency technology, and to components of this type which contain media according to the invention, and to the production and use of these components. The components according to the invention are suitable, in particular, as phase shifters in the microwave and millimetre wave region, for microwave and millimetre wave array antennae and very particularly for so-called tunable "reflectarrays".

8 Claims, No Drawings

CYANOPYRIMIDINE DERIVATIVES

The present invention relates to cyanopyrimidine derivatives, liquid-crystalline media comprising the same and their use, in particular for high-frequency technology, especially components for high-frequency devices, in particular antennas, especially for the gigahertz region and the terahertz region, which are operated in the microwave or millimetre wave region.

Liquid-crystalline media have been used for many years in electro-optical displays (liquid crystal displays—LCDs) in order to display information.

However, liquid-crystalline media have recently also increasingly been proposed for use in components for high-frequency technology, in particular microwave technology, such as, for example, in DE 10 2004 029 429 A and in JP 2005-120208 (A).

An industrially valuable application of liquid-crystalline media in high-frequency technology is based on their property that their dielectric properties can be controlled by a variable voltage, particularly for the gigahertz region. Thus, tuneable antennae can be designed which contain no moving parts (A. Gaebler, A. Moessinger, F. Goelden, et al., "Liquid Crystal-Reconfigurable Antenna Concepts for Space Applications at Microwave and Millimeter Waves", International Journal of Anntenae and Propagation, Vol. 2009, Article ID 876989, 7 pages, 2009. doi:10.1155/2009/876989).

The publication A. Penirschke, S. Müller, P. Scheele, C. Weil, M. Wittek, C. Hock and R. Jakoby: "Cavity Perturbation Method for Characterization of Liquid Crystals up to 35 GHz", 34$^{th}$ European Microwave Conference—Amsterdam, 545-548, describes, inter alia, the properties of the known, liquid-crystalline single substance K15 (Merck KGaA, Germany) at a frequency of 9 GHz.

In DE 10 2004 029 429 A cited above the use of conventional liquid-crystal media in microwave technology, inter alia in phase shifters, is described. Liquid-crystalline media have already been investigated therein with respect to their properties in the corresponding frequency range.

Liquid crystal media comprising for example compounds of the formula below,

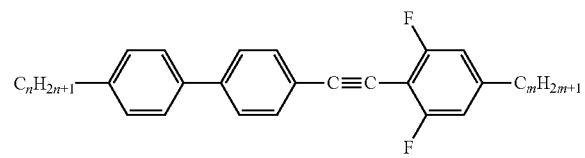

are used as a host mixture for the investigation of compounds, which are suggested for the usage in components for microwave applications and are described in F. Gölden, "Liquid Crystal Based Microwave Components with Fast Response Times: Materials, Technology, Power Handling Capability", Dissertation, Technische Universität Darmstadt, 2009, (D17); A. Lapanik, "Single compounds and mixtures for microwave applications, Dielectric, microwave studies on selected systems", Dissertation, Technische Universität Darmstadt, 2009, (D17); "Nematic LC mixtures with high birefringence in microwave region", A. Lapanik, F. Gölden, S. Müller, A. Penirschke, R. Jakoby und W. Haase, Frequenz 2011, 65, 15-19; "Highly birefringent nematic mixtures at room temperature for microwave applications", A. Lapanik, F. Gölden, S. Müller, R. Jakoby und W. Haase, Journal of Optical Engineering, published online, as well as in the laid-open document WO2013/045029.

In EP2935513 A1 polar pyrimidine derivatives of the following structures are proposed as co-component in liquid crystal mixtures for microwave applications:

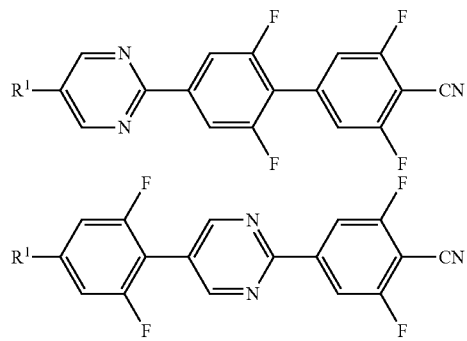

However, the compositions or individual compounds known to date are generally afflicted with disadvantages. Most of them result, besides other deficiencies, in disadvantageously high losses and/or inadequate phase shifts or inadequate material quality. Whereas, for example, some individual compounds do not have favourable liquid-crystalline phases and have very high melting points, other substances in turn lack sufficiently high values of the optical anisotropy (Δn) and the dielectric anisotropy (Δε).

For use in high-frequency technology, liquid-crystalline media having particular, to date rather unusual, non-standard properties, or combinations of properties, are required. In particular, the loss in the microwave region and/or millimetre wave region must be reduced and the material quality (η) must be improved.

Furthermore, applications in antenna technology take place under in some cases strongly varying outside boundary conditions, such as, for example, large temperature variations. Hence, there is a demand for an improvement in the low-temperature stability of the liquid-crystalline media (i.e. no crystallisation of the liquid crystal or one of its components upon cooling must occur). Both an improvement in the operating properties and also in the shelf life are necessary here.

Thus, novel components for liquid-crystalline media having improved properties are necessary and there is a considerable demand for improved liquid-crystalline media having suitable properties for corresponding practical applications.

It is an aim of the present invention to provide improved liquid crystal media for the use for high-frequency components, in particular antennae, especially for the gigahertz range having a suitably high Δε, a suitably high Δn, a suitable nematic phase range and high clearing temperature and low rotational viscosity, which do not have the disadvantages of the prior-art materials, or at least only do so to a considerably reduced extent.

Surprisingly, it has been found that the problem can be solved by the use of compounds of formula M below.

The present invention relates to compounds of formula M

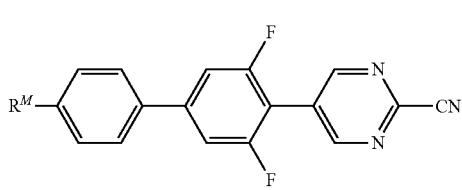

wherein
$R^M$ is alkyl having 1 to 20 C atoms, which is straight chain or branched, and which is unsubstituted, mono- or polysubstituted by F, Cl or CN, preferably by F, and in which one or more $CH_2$ groups are optionally replaced, in each case independently from one another, by —O—, —S—, —$NR^{O1}$—, —$SiR^{O1}R^{O2}$—, —CO—, —COO—, —OCO—, —OCO—O—, —S—CO—, —CO—S—, —$CY^{O1}$=$CY^{O2}$— or —C≡C— in such a manner that O and/or S atoms are not linked directly to one another, preferably n-alkyl or n-alkoxy with 1 to 9 C-atoms, preferably with 2 to 5 C-atoms, alkenyl, alkenyloxy or alkoxyalkyl with 2 to 9 C-atoms, preferably with 2 to 5 C-atoms or halogenated alkyl, halogenated alkenyl or halogenated alkoxy with preferably up to 9 C-atoms, preferably mono fluorinated, di-fluorinated or oligofluorinated alkyl, alkenyl or alkoxy with preferably up to 9 C-atoms, most preferably n-alkyl, n-alkoxy, alkenyl, alkenyloxy or alkoxyalkyl with preferably up to 9 C-atoms, $Y^{O1}$ and $Y^{O2}$ independently of each other, denote F, Cl or CN, and alternatively one of them may be H, and
$R^{O1}$ and $R^{O2}$ independently of each other, denote H or alkyl with 1 to 12 C-atoms.

The compounds of the general formula M can be prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can be made here of variants known per se which are not mentioned here in greater detail.

If desired, the starting materials can also be formed in situ by not isolating them from the reaction mixture, but instead immediately converting them further into the compounds of the general formula M.

The syntheses of compounds of the general formula M according to the invention are described by way of example in the examples. The starting substances can be obtained by generally accessible literature procedures or are commercially available. Preferred synthetic routes are described for pyrimidine derivatives in DE4409431A1 and can easily be adapted by the skilled person for the preparation of compounds of formula M.

Particularly suitable synthetic routes to the compounds according to the invention are explained below with reference to Scheme 1.

Scheme 1. Synthesis of the compounds of the formula M. The radical $R^M$ has the meaning defined above, X denotes Cl, Br, or I.

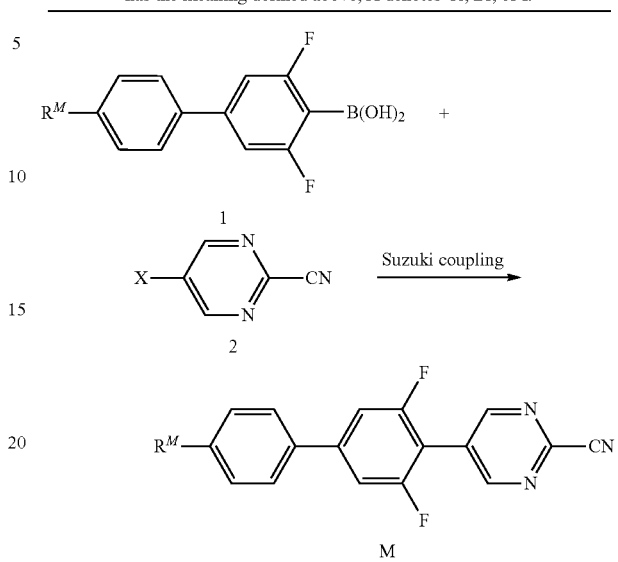

Suitably substituted biphenyl boronic acids (1) can be prepared as described in the literature and in the synthesis example below. Pyrimidine-2-carbonitriles 2 are commercially available.

Scheme 1 should only be regarded as illustrative. The person skilled in the art will be able to carry out corresponding variations of the syntheses presented, and also follow other suitable synthetic routes, in order to obtain compounds of the formula M.

In accordance with the synthesis depicted above, the present invention in an embodiment also encompasses one or more processes for the preparation of compounds of the formula M.

The invention thus encompasses a process for the preparation of compounds of the formula M which is characterised in that it comprises a process step in which a 4-chloro, 4-bromo- or 4-iodopyrimidine-2-carbonitrile (2) is reacted in a transition metal catalysed coupling reaction, e.g. a Suzuki coupling, a Kumada coupling or alike, to give 4-aryl-pyrimidine carbonitriles.

The process and the subsequent work-up of the reaction mixture can basically be carried out as a batch reaction or in a continuous reaction procedure. The continuous reaction procedure encompasses, for example, reaction in a continuous stirred-tank reactor, a stirred-reactor cascade, a loop or cross-flow reactor, a flow tube or in a microreactor. The reaction mixtures are optionally worked up, as necessary, by filtration via solid phases, chromatography, separation between immiscible phases (for example extraction), adsorption onto solid supports, removal of solvents and/or azeotropic mixtures by distillation, selective distillation, sublimation, crystallisation, co-crystallisation or by nanofiltration on membranes.

As already mentioned, the compounds of the general formula M can be used in liquid-crystalline media. The present invention therefore also relates to a liquid-crystalline medium comprising at least two liquid-crystalline compounds, comprising at least one compound of the general formula M.

The compounds of formula M are preferably selected from the group of compounds of formulae M-1 and M-2

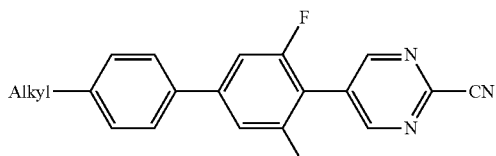
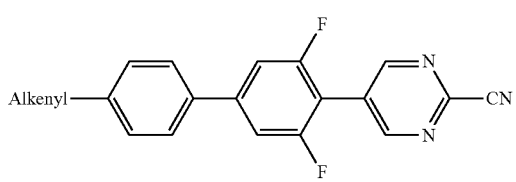
wherein alkyl denotes unbranched alkyl having 2 to 7 C atoms and alkenyl denotes alkenyl having 2 to 7 C atoms.
In a preferred embodiment of the present invention the liquid-crystalline media additionally comprise one or more compounds of the formula I,
in which
denotes
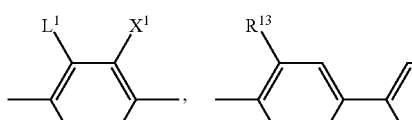
preferably
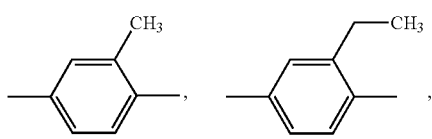
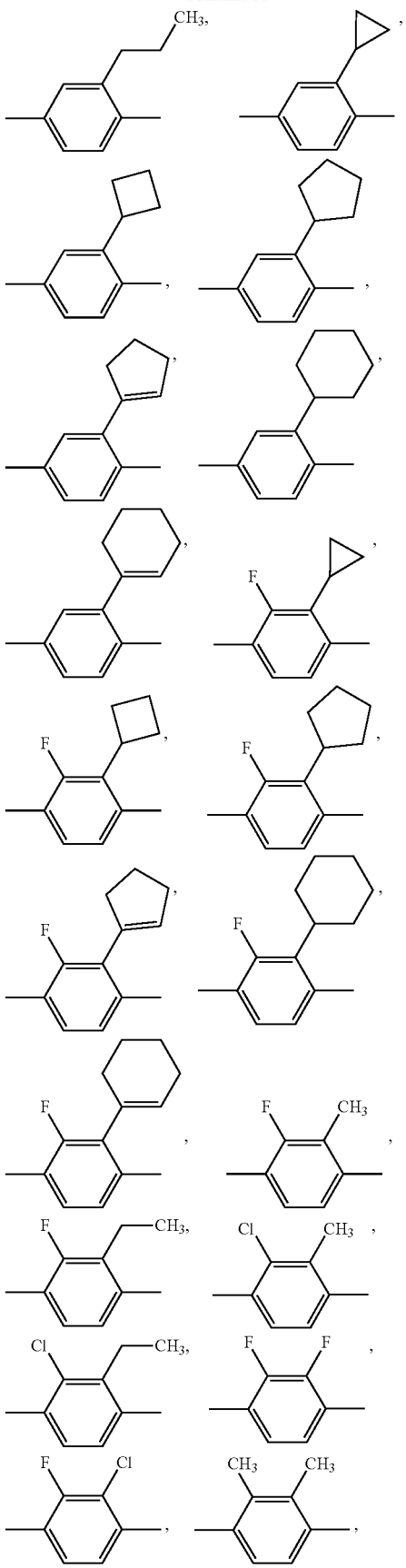

-continued

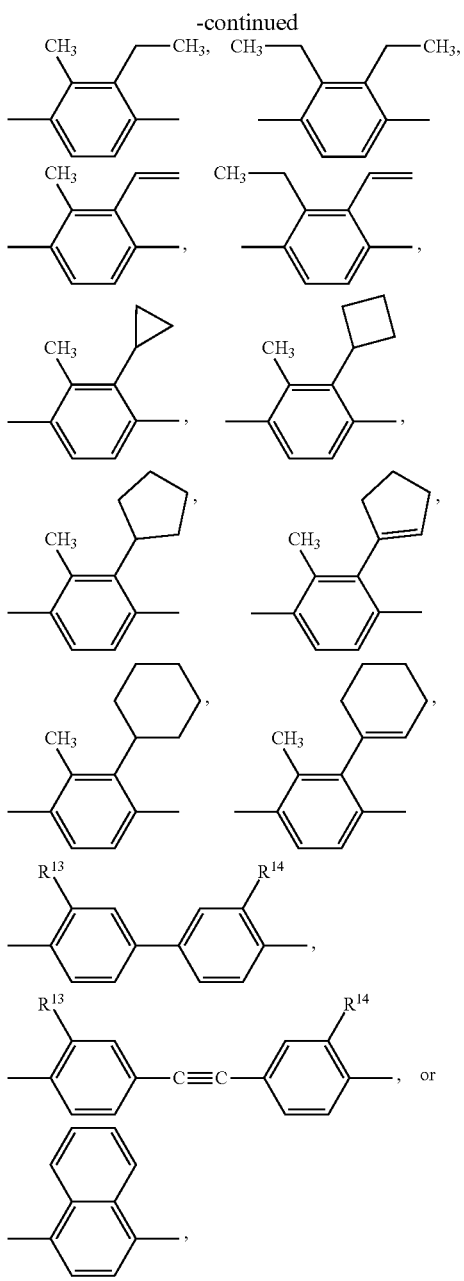

particularly preferably

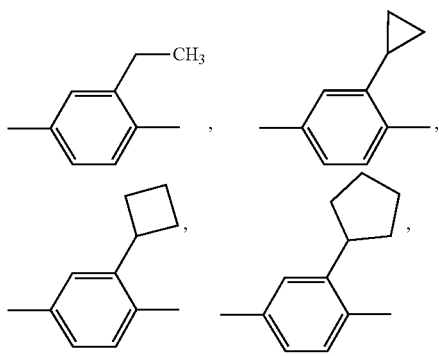

-continued

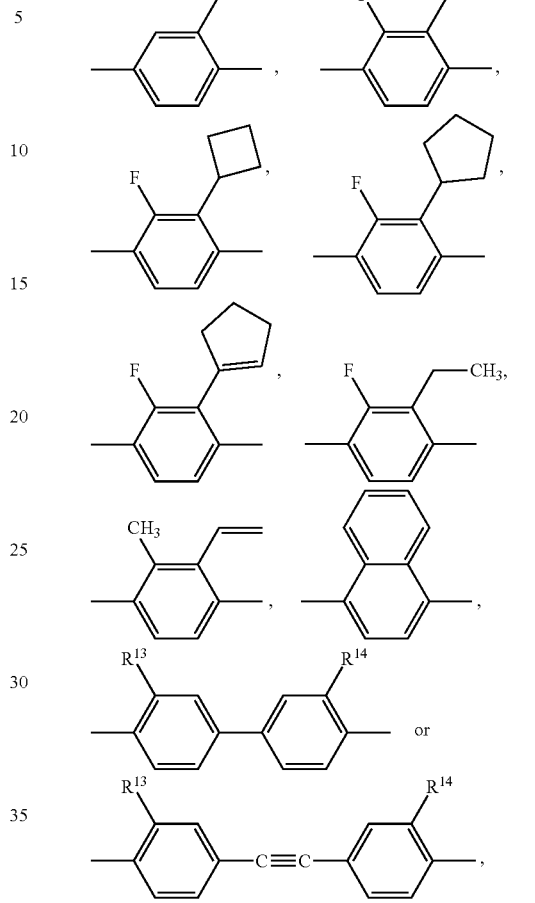

$L^1$ denotes alkyl having 1 to 6 C atoms, cycloalkyl having 3 to 6 C atoms or cycloalkenyl having 4 to 6 C atoms, preferably $CH_3$, $C_2H_5$, n-$C_3H_7$(—$(CH_2)_2CH_3$), i-$C_3H_7$ (—$CH(CH_3)_2$), cyclopropyl, cyclobutyl, cyclohexyl, cyclopent-1-enyl or cyclohex-1-enyl, and particularly preferably $CH_3$, $C_2H_5$, cyclopropyl or cyclobutyl, $X^1$ denotes H, alkyl having 1 to 3 C atoms or halogen, preferably H, F or Cl, and particularly preferably H or F and very particularly preferably F, $R^{11}$ to $R^{14}$, independently of one another, denote unfluorinated alkyl or unfluorinated alkoxy, each having 1 to 15 C atoms, unfluorinated alkenyl, unfluorinated alkenyloxy or unfluorinated alkoxyalkyl, each having 2 to 15 C atoms, or cycloalkyl, alkylcycloalkyl, cycloalkenyl, alkylcycloalkenyl, alkylcycloalkylalkyl or alkylcycloalkenylalkyl, each having up to 15 C atoms, and alternatively one of $R^{13}$ and $R^{14}$ or both also denote H, preferably, $R^{11}$ and $R^{12}$, independently of one another, denote unfluorinated alkyl or unfluorinated alkoxy, each having 1 to 7 C atoms, or unfluorinated alkenyl, unfluorinated alkenyloxy or unfluorinated alkoxyalkyl, each having 2 to 7 C atoms, particularly preferably, $R^{11}$ denotes unfluorinated alkyl having 1 to 7 C atoms or unfluorinated alkenyl, unfluorinated alkenyloxy or unfluorinated alkoxyalkyl, each having 2 to 7 C atoms, and particularly preferably R$^{12}$ denotes unfluorinated alkyl or unfluorinated alkoxy, each having 1 to 7 C atoms, and preferably R$^{13}$ and R$^{14}$ denote H, unfluorinated alkyl having 1 to 5 C atoms, unfluorinated cycloalkyl or cycloalkenyl having 3 to 7 C atoms, unfluorinated alkylcyclohexyl or unfluorinated cyclohexylalkyl, each having 4 to 12 C atoms, or unfluorinated alkylcyclohexylalkyl having 5 to 15 C atoms, particularly preferably cyclopropyl, cyclobutyl or cyclohexyl, and very particularly preferably at least one of R$^{13}$ and R$^{14}$ denotes n-alkyl, particularly preferably methyl, ethyl or n-propyl, and the other denotes H or n-alkyl, particularly preferably H, methyl, ethyl or n-propyl.

The liquid-crystal media according to the invention are eminently suitable for use in components for high-frequency technology or for the microwave region and/or millimetre wave region of the electromagnetic spectrum. The present invention relates to this use of the media and to these components.

In a first preferred embodiment of the present invention, the component for high-frequency technology contains a liquid-crystal medium which comprises a component A which consists of one, two or more compounds of the formula M.

In accordance with a further preferred embodiment of the present invention, the component for high-frequency technology contains a liquid-crystalline medium comprising a first component, component A, which consists of one or more compounds of the above-mentioned formula M, and one or more further components selected from the group of components B to F defined below, a component, component B, consisting of one or more compounds of formula I and/or IA, a strongly dielectrically positive component, component C, which has a dielectric anisotropy of 10.0 or more, a strongly dielectrically negative component, component D, which has a dielectric anisotropy of −5.0 or less, a further component, component E, which has a dielectric anisotropy in the range from more than −5.0 to less than 10.0 and consists of compounds having seven or more, preferably eight or more, five- or six-membered rings, and a further component, component F, which likewise has a dielectric anisotropy in the range from more than −5.0 to less than 10.0 and consists of compounds having up to six five- or six-membered rings.

Typical examples of five-membered rings are

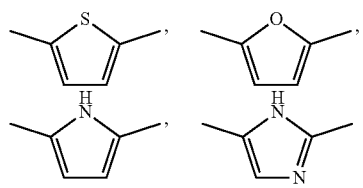

and others.

Typical examples of six-membered rings are

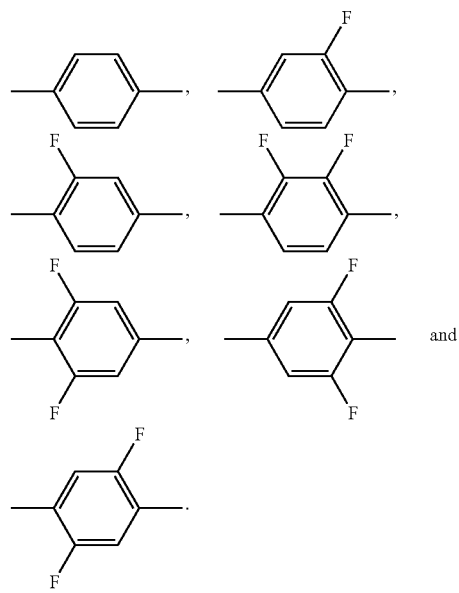

The five- and six-membered rings also include saturated and partially saturated rings, as well as heterocyclic rings.

For the purposes of the present application, condensed ring systems which consist of two of these rings, i.e. two five-membered rings, one five-membered ring or two six-membered rings, such as, for example,

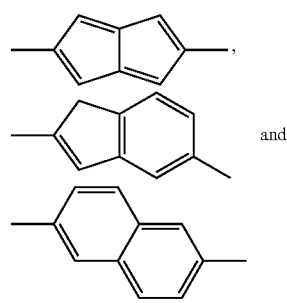

are counted as one of these five- or six-membered rings on assignment of the compounds to components B or E.

Correspondingly, condensed ring systems which consist of a combination of three or more of these rings which are incorporated into the molecule in the longitudinal direction, such as, for example,

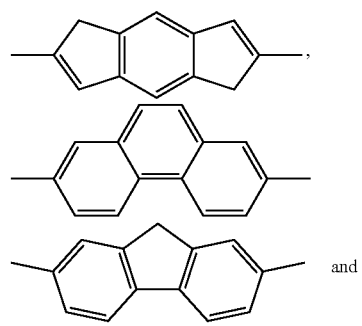

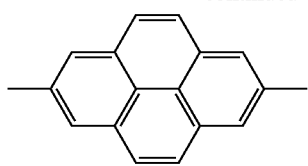

are counted as two of these five- or six-membered rings.

By contrast, condensed ring systems which are incorporated into the molecule in the transverse direction, such as, for example,

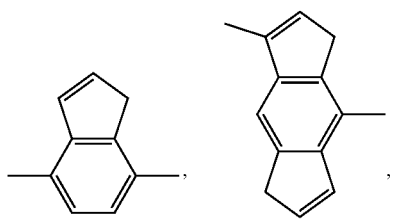

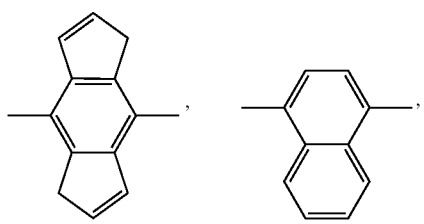

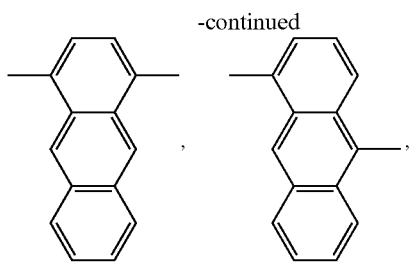

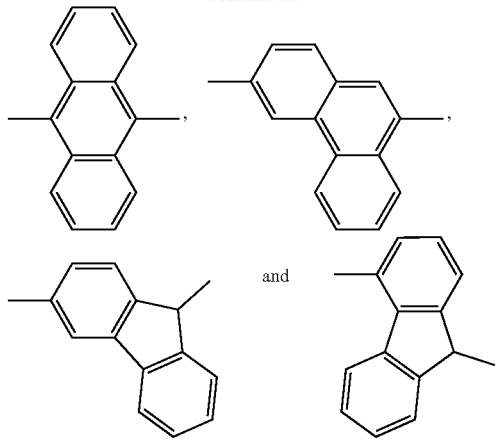

are counted as one of these five- or six-membered rings.

The present invention likewise relates to the directly preceding liquid-crystalline media and to those described below, and to the use thereof in electro-optical displays and in particular in components for high-frequency technology.

In a preferred embodiment of the present invention, the liquid-crystal medium, or component B of the liquid crystal medium, comprises one or more compounds of the formula I, preferably selected from the group of the compounds of the formulae I-1 to I-4, preferably of the formulae I-1 and/or I-2 and/or I-3 and/or I-4, preferably of the formulae I-1 and I-2, these compounds more preferably predominantly consist thereof, even more preferably essentially consist thereof and very particularly preferably completely consist thereof:

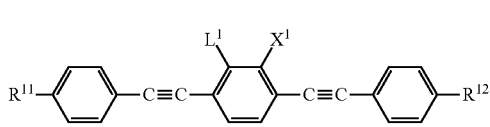

I-1

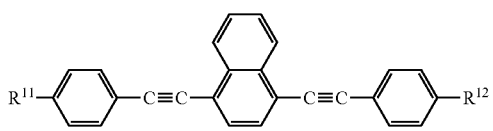

I-2

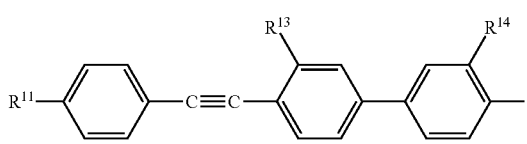

I-3

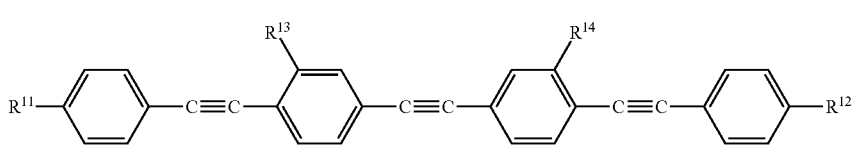

I-4 in which $L^1$ denotes alkyl having 1 to 6 C atoms, alkenyl having 2 to 6 C atoms, cycloalkyl having 3 to 6 C atoms or cycloalkenyl having 4 to 6 C atoms, preferably $CH_3$, $C_2H_5$, n-$C_3H_7$ (—$(CH_2)_2CH_3$), i-$C_3H_7$ (—$CH(CH_3)_2$), —$CH=CH_2$, cyclopropyl, cyclobutyl, cyclopentyl, cyclohexyl, cyclopent-1-enyl or cyclohex-1-enyl, and particularly preferably $CH_3$, $C_2H_5$, cyclopropyl or cyclobutyl, $X^1$ denotes H, alkyl having 1 to 3 C atoms or halogen, preferably H, F or Cl, and particularly preferably H, F or CH$_3$, even more preferably H or F and very particularly preferably F, and the other parameters have the respective meanings indicated above for formula I, and preferably $R^{11}$ denotes unfluorinated alkyl having 1 to 7 C atoms, and
$R^{12}$ denotes unfluorinated alkyl having 1 to 7 C atoms or unfluorinated alkoxy having 1 to 7 C atoms, and one of
$R^{13}$ and $R^{14}$ denotes methyl, ethyl or n-propyl, and
the other of
$R^{13}$ and $R^{14}$ denotes H, methyl, ethyl or n-propyl.

In a particularly preferred embodiment of the present invention, the liquid-crystal medium, or component B of the liquid crystal medium, comprises one or more compounds of the formula I-1, preferably selected from the group of the compounds of the formulae I-1a-1 to I-1a-12 and I-1 b-1 to I-1b-12

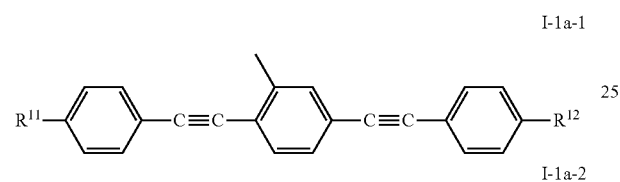

-continued

I-1b-5
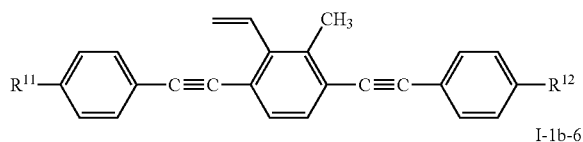

I-1b-6
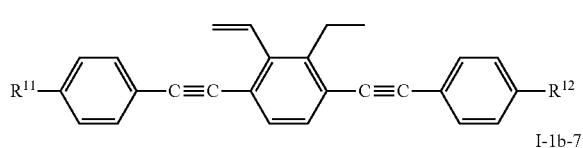

I-1b-7
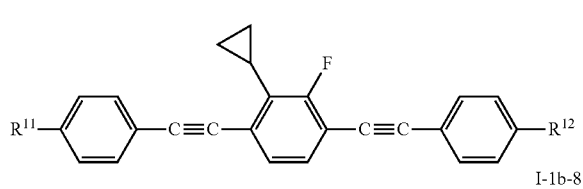

I-1b-8
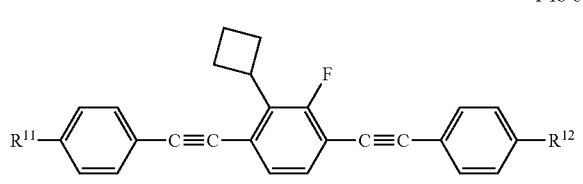

I-1b-9
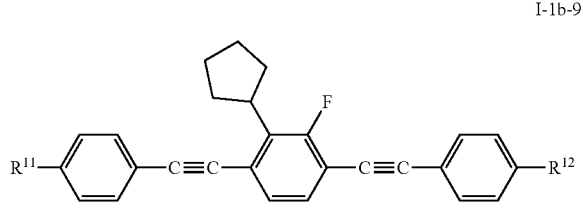

I-1b-10
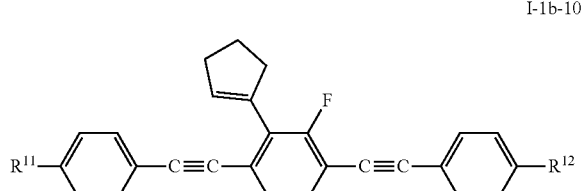

I-1b-11
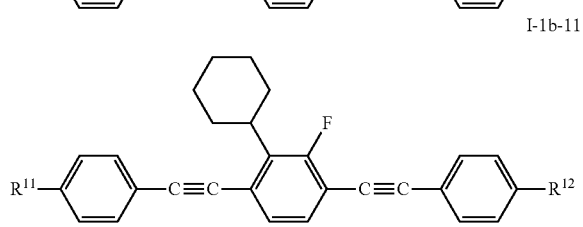

-continued

I-1b-12
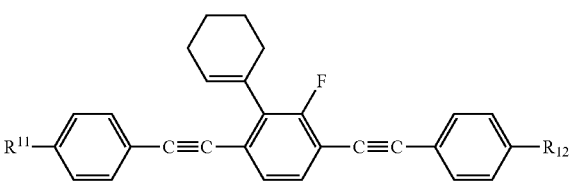

in which the parameters have the meanings as given above under formula I-1, and preferably $R^{11}$ and $R^{12}$, independently of one another, denote an alkyl radical having 2 to 7 C atoms, for example a propyl or hexyl radical, or each denote a propyl, butyl, pentyl or hexyl radical.

In a very particularly preferred embodiment of the present invention, the liquid-crystal medium, or component B of the liquid-crystal medium, comprises one or more compounds of the formula I, preferably selected from the group of the compounds of the formulae I-1a-2, I-1a-5, I-1a-7, I-1a-8, I-1a-9, I-1a-10, I-1 b-5, I-1 b-7, I-1 b-8, I-1 b-9, I-1b-10, where the parameters have the meaning given above, and particularly preferably $R^{11}$ and $R^{12}$, independently of one another, denote unfluorinated alkyl having 1 to 7 C atoms or unfluorinated alkoxy having 1 to 6 C atoms, particularly preferably one of $R^{11}$ and $R^{12}$ denotes alkyl and the other denotes alkyl or alkoxy, and very particularly preferably $R^{11}$ and $R^{12}$ have different meanings from one another.

In a preferred embodiment of the present invention, the liquid-crystal medium, or component B of the liquid-crystal medium, comprises one or more compounds of the formula I-2, in which preferably $R^{11}$ and $R^{12}$, independently of one another, denote an alkyl radical having 2 to 7 C atoms, for example a propyl or hexyl radical, or each denote a propyl, butyl, pentyl or hexyl radical.

In a preferred embodiment of the present invention, the liquid-crystal medium, or component B of the liquid-crystal medium, comprises one or more compounds of the formula I-3, preferably selected from the group of the compounds of the formulae I-3a-1 to I-3a-3 and I-3b-1 to I-3b-3, preferably I-3a-2, I-3b-2, I-3a-1
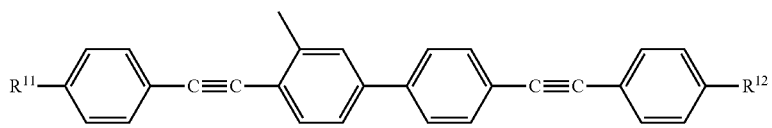

I-3a-2
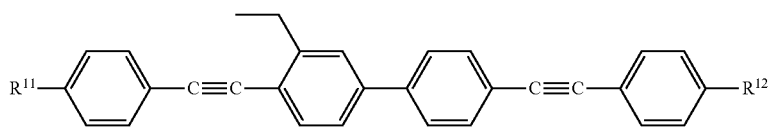

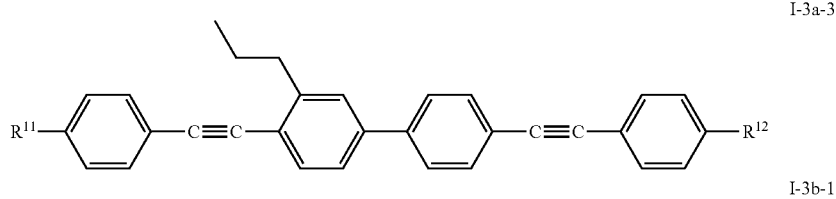

I-3a-3

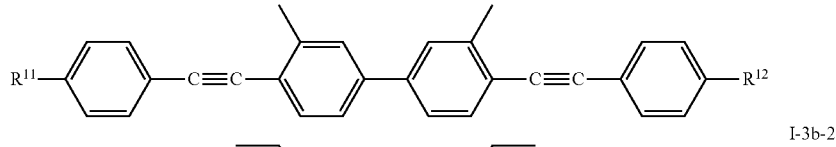

I-3b-1

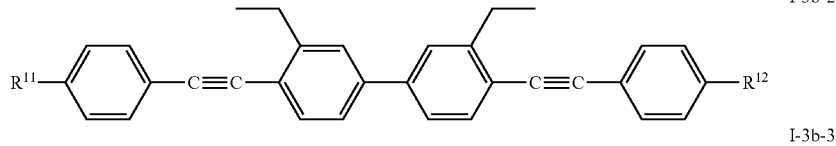

I-3b-2

I-3b-3 in which the parameters have the meanings given above under formula I-3, and preferably $R^{11}$ and $R^{12}$, independently of one another, denote an alkyl radical having 2 to 7 C atoms, for example a propyl or hexyl radical, or each denote a propyl, butyl, pentyl or hexyl radical.

In a preferred embodiment of the present invention, the liquid-crystal medium, or component B of the liquid-crystal medium, comprises one or more compounds of the formula I-4, preferably selected from the group of the compounds of the formulae I-4a-1 to I-4a-3 and I-4b-1 to I-4b-3, preferably I-4b-2,

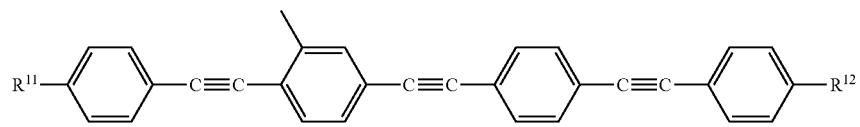

I-4a-1

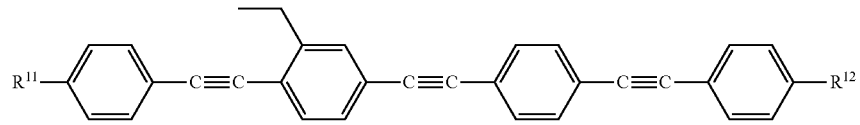

I-4a-2

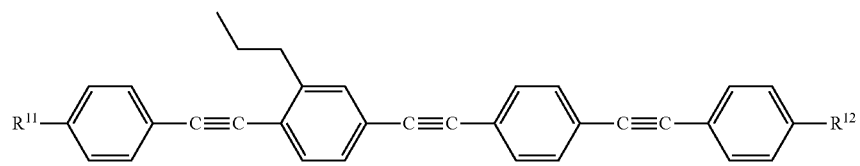

I-4a-3

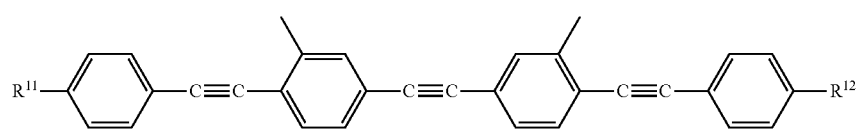

I-4b-1

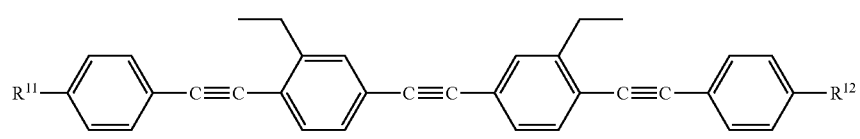

I-4b-2

-continued

I-4b-3

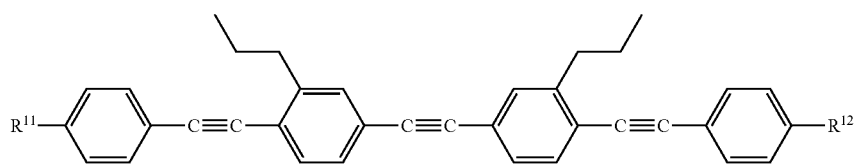

in which the parameters have the meanings given above under formula I-4, and preferably $R^{11}$ and $R^{12}$, independently of one another, denote an alkyl radical having 2 to 7 C atoms, for example a propyl or hexyl radical, or each denote a propyl, butyl, pentyl or hexyl radical.

In a preferred embodiment of the present invention the liquid-crystal medium comprises one or more compounds of formula IA

IA

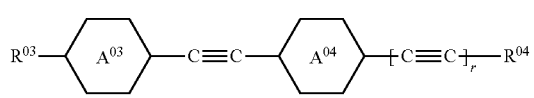

wherein
r denotes 0 or 1,

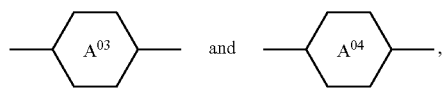

independently of one another, denote

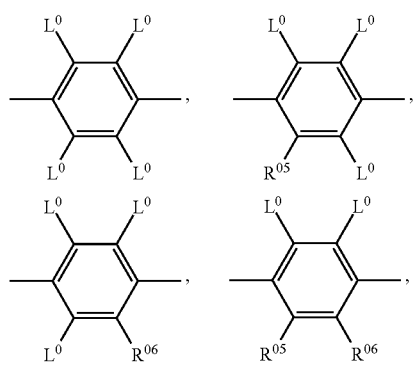

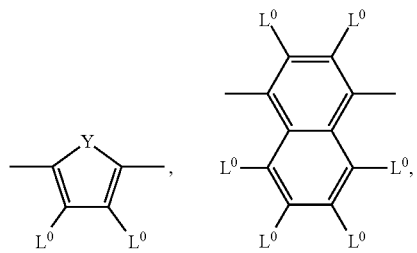

-continued

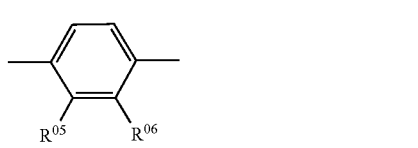

preferably

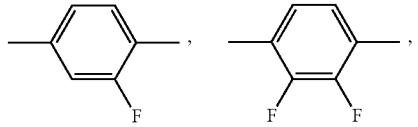

particularly preferably

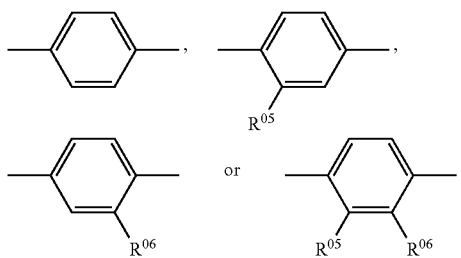

wherein Y denotes S or O, and wherein in the 1,4-phenylene groups, one C—H group or a plurality of CH groups, preferably one CH group or two CH groups, preferably not adjacent, particularly preferably one CH group, may be replaced by N, and $L^0$ on each occurrence, independently of one another, denotes H, Br, Cl, F, —CN, —NCS, —SCN, SF$_5$, C$_1$-C$_{10}$ alkyl, C$_1$-C$_{10}$ alkoxy, C$_3$-C$_6$ cycloalkyl or a mono- or polyfluorinated C$_1$-C$_{10}$ alkyl or alkoxy group, preferably H, F or C$_1$-C$_3$ alkyl $R^{03}$ and $R^{04}$ each, independently of one another, denote a halogenated or unsubstituted alkyl radical having 1 to 15 C atoms, where, in addition, one or more CH$_2$ groups in these radicals may each be replaced, independently of one another, by —C≡C—, —CH=CH—, —CF=CF—, —CF=CH—, —CH=CF—, —(CO)O—, —O(CO)—, —(CO)—, —O— or —S— in such a way that O or S atoms are not linked directly to one another and, optionally, independently of one another, $R^{03}$ may also denote ethynyl (i.e. —C≡CH) and $R^{04}$ may also denote H, and $R^{05}$ and $R^{06}$ each, independently of one another, denote a halogenated or unsubstituted alkyl radical having 1 to 6, preferably having 1 to 4, particularly preferably having 1, 2 or 3, C atoms, where, in addition, one or more CH$_2$ groups in these radicals may each be replaced, independently of one another, by —C≡C—, —CH=CH—, —CF=CF—, —CF=CH—, —CH=CF—, —(CO)O—, —O(CO), —(CO)—, —O— or —S— in such a way that O or S atoms are not linked directly to one another.

According to the present invention the compounds of formula IA are preferably selected from compounds of the formulae IA-1 to IA-7:

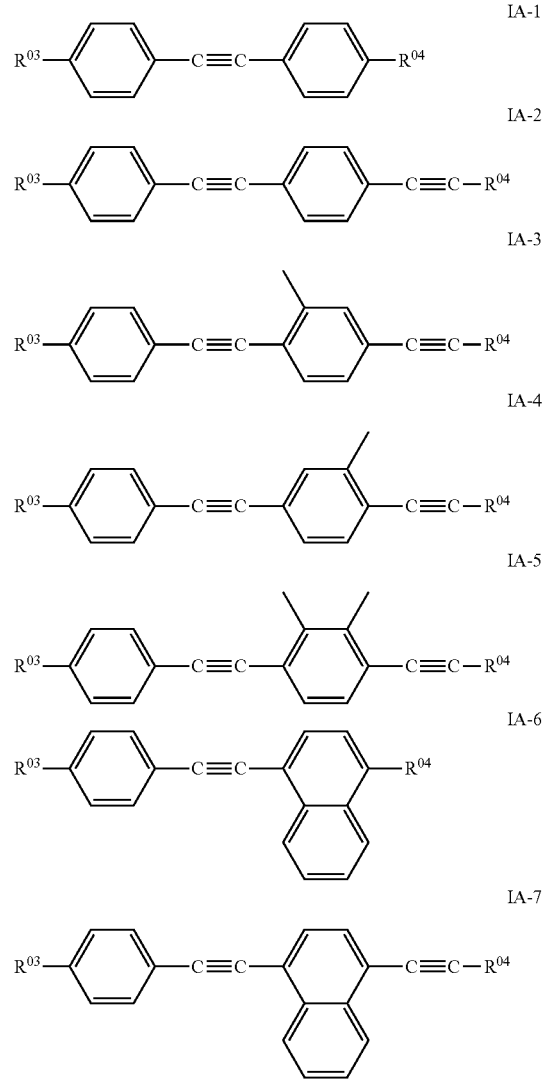

wherein $R^{03}$ and $R^{04}$ have the meaning indicated above for formula IA and preferably, independently of each other, denote alkyl having 1 to 7 C atoms.

In a preferred embodiment of the present invention, component C comprises one or more compounds selected from the group of the compounds of the formulae IIA and IIB,

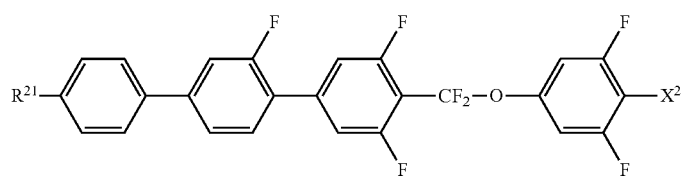

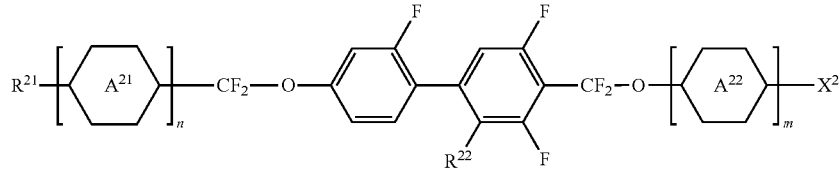

wherein
R²¹ denotes unfluorinated alkyl or unfluorinated alkoxy, each having 1 to 15 C atoms, or unfluorinated alkenyl, unfluorinated alkenyloxy or unfluorinated alkoxyalkyl, each having 2 to 15 C atoms, preferably alkyl, particularly preferably n-alkyl,
R²² denotes H, unfluorinated alkyl or unfluorinated alkoxy, each having 1 to 5, preferably 1 to 3, particularly preferably 3, C atoms,

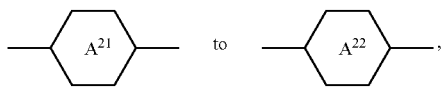

independently of one another and, if they occur more than once, these also in each case independently of one another, denote

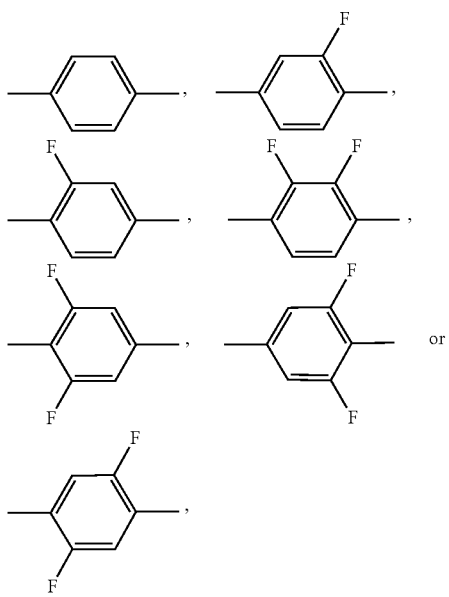

preferably

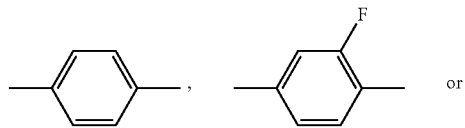

n and m, independently of one another, denote 1 or 2, preferably
(n+m) denotes 3 or 4, and particularly preferably
n denotes 2,
X² denotes F, Cl, —CF₃ or —OCF₃, preferably F or Cl, particularly preferably F.

Preferred compounds of the formula IIA are the compounds of the corresponding sub-formula IIA-1

IIA-1
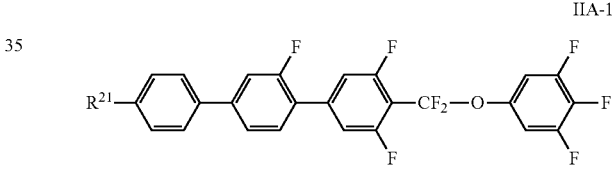

in which R²¹ has the meaning given above.

Preferred compounds of the formula IIB are the compounds of the corresponding sub-formulae IIB-1 and IIB-2:

IIB-1
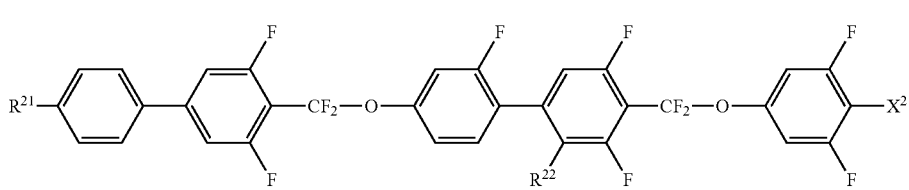

IIB-2
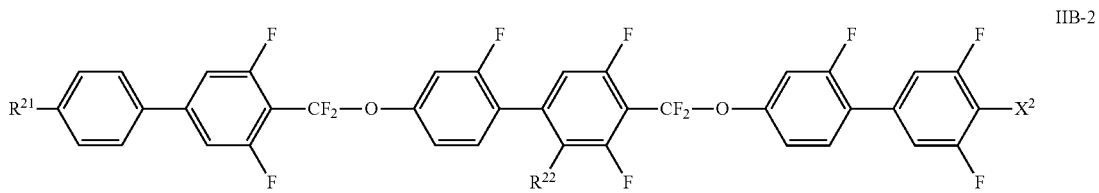

in which $R^{21}$, $R^{22}$ and $X^2$ have the respective meanings given above.

In a preferred embodiment of the present invention, component D comprises one or more compounds selected from the group of the compounds of the formulae IIIA and IIIB:

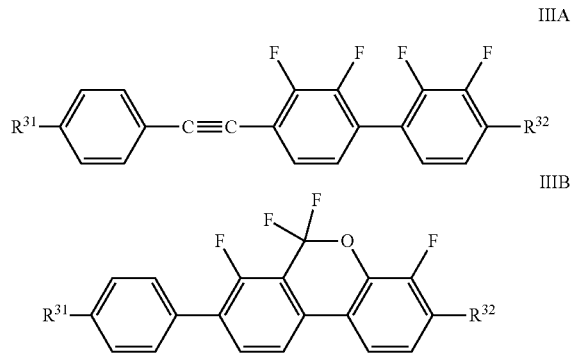

IIIA

IIIB in which
$R^{31}$ and $R^{32}$, independently of one another, have the meanings indicated above for $R^{21}$ under formula IIA,
and preferably
$R^{31}$ denotes $C_nH_{2n+1}$ or $CH_2$=CH—$(CH_2)_z$ and
$R^{32}$ denotes $C_mH_{2m+1}$ or O—$C_mH_{2m+1}$ or $(CH_2)_z$—CH=$CH_2$,
and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{31}$ and $R^{32}$) here are, in particular, ($C_nH_{2n+1}$ and $C_mH_{2m+1}$) and ($C_nH_{2n+1}$ and O—$C_mH_{2m+1}$).

Preferred compounds of the formula IIIB are the compounds of the sub-formulae IIIB-1 and IIIB-2:

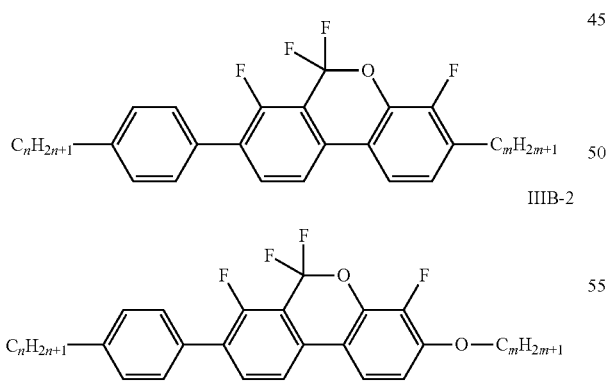

IIIB-1

IIIB-2 in which
n and m each have the meanings given above for formula IIIB and preferably, independently of one another, denote an integer in the range from 1 to 7.

In a preferred embodiment of the present invention, component E comprises one or more compounds of the following formula IV:

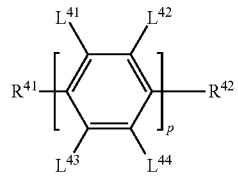

IV in which
$R^{41}$ and $R^{42}$, independently of one another, have one of the meanings indicated above for $R^{11}$ under formula I,
$L^{41}$ to $L^{44}$ on each appearance, in each case independently of one another, denote H, alkyl having 1 to 5 C atoms, F or Cl, and
p denotes an integer in the range from 7 to 14, preferably from 8 to 12 and particularly preferably from 9 to 10, and preferably
at least two of the substituents
$L^{41}$ to $L^{44}$ present have a meaning other than H, and
$R^{41}$ denotes $C_nH_{2n+1}$ or $CH_2$=CH—$(CH_2)_z$, and
$R^{42}$ denotes $C_mH_{2m+1}$ or O—$C_mH_{2m+1}$ or $(CH_2)_z$—CH=$CH_2$,
and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

In a preferred embodiment of the present application, the liquid-crystal medium additionally comprises a further component, component F, which preferably consists of one or more compounds selected from the group of the compounds of the formulae V to IX:

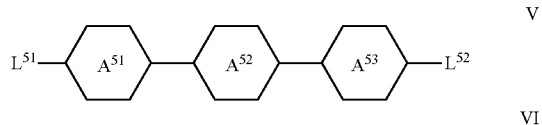

V

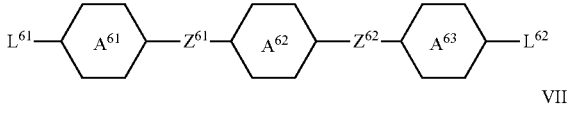

VI

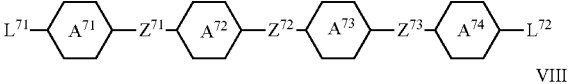

VII

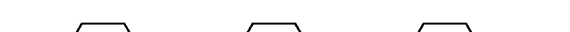

VIII

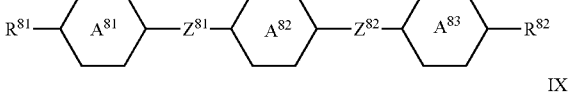

IX

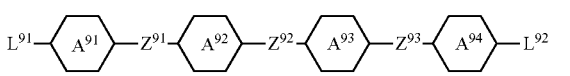

in which
$L^{51}$ denotes $R^{51}$ or $X^{51}$,
$L^{52}$ denotes $R^{52}$ or $X^{52}$,
$R^{51}$ and $R^{52}$, independently of one another, denote H, unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl, X$^{51}$ and X$^{52}$, independently of one another, denote H, F, Cl, —CN, —NCS, —SF$_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably fluorinated alkoxy, fluorinated alkenyloxy, F or Cl, and

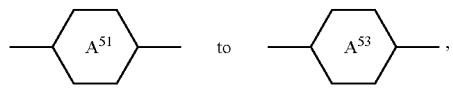

independently of one another, denote

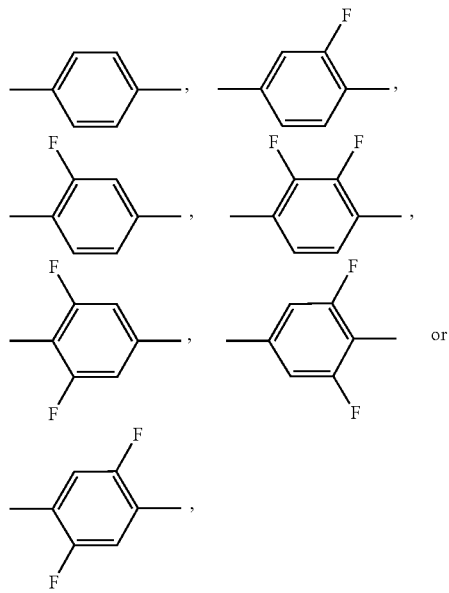

preferably

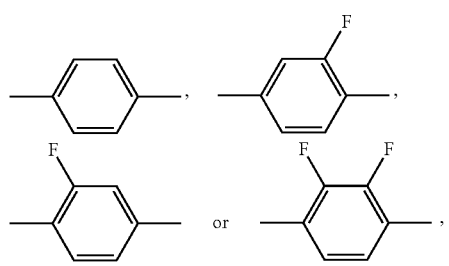

L$^{61}$ denotes R$^{61}$ and, in the case where Z$^{61}$ and/or or Z$^{62}$ denote trans-CH═CH— or trans-CF═CF—, alternatively also denotes X$^{61}$, L$^{62}$ denotes R$^{62}$ and, in the case where Z$^{61}$ and/or Z$^{62}$ denote trans-CH═CH— or trans-CF═CF—, alternatively also denotes X$^{62}$, R$^{61}$ and R$^{62}$, independently of one another, denote H, unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl, X$^{61}$ and X$^{62}$, independently of one another, denote F or Cl, —CN, —NCS, —SF$_5$, fluorinated alkyl or alkoxy having 1 to 7 C atoms or fluorinated alkenyl, alkenyloxy or alkoxyalkyl having 2 to 7 C atoms, preferably —NCS, one of
Z$^{61}$ and Z$^{62}$ denotes trans-CH═CH—, trans-CF═CF— or —C≡C— and the other, independently thereof, denotes trans-CH═CH—, trans-CF═CF— or a single bond, preferably one of them denotes —C≡C— or trans-CH═CH— and the other denotes a single bond, and

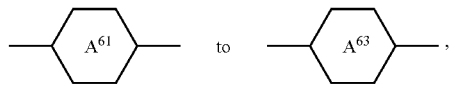

independently of one another, denote

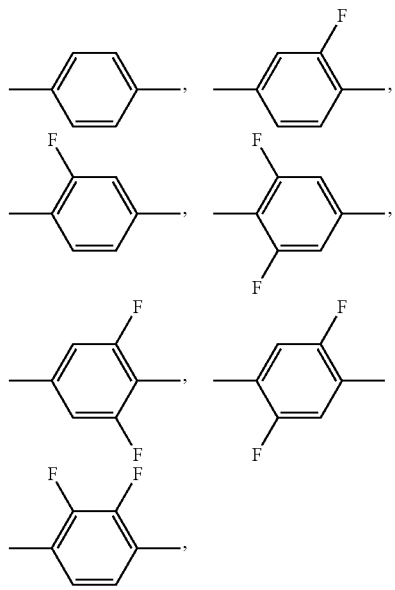

preferably

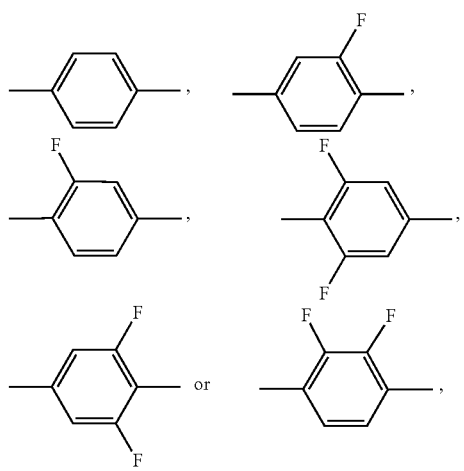

L$^{71}$ denotes R$^{71}$ or X$^{71}$,
L$^{72}$ denotes R$^{72}$ or X$^{72}$, $R^{71}$ and $R^{72}$, independently of one another, denote H, unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl, $X^{71}$ and $X^{72}$, independently of one another, denote H, F, Cl, —CN, —NCS, —SF$_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably fluorinated alkoxy, fluorinated alkenyloxy, F or Cl, and $Z^{71}$ to $Z^{73}$, independently of one another, denote trans-CH=CH—, trans-CF=CF—, —C≡C— or a single bond, preferably one or more of them denote a single bond, particularly preferably all denote a single bond and

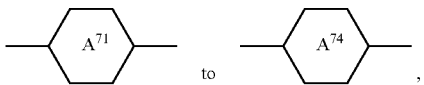

independently of one another, denote

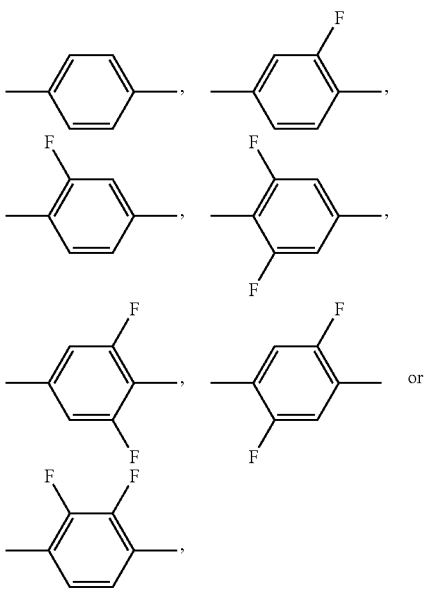

preferably

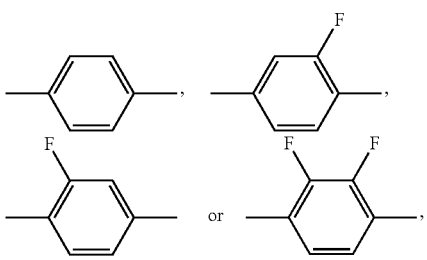

$R^{81}$ and $R^{82}$, independently of one another, denote H, unfluorinated alkyl or alkoxy having 1 to 15, preferably 3 to 10, C atoms or unfluorinated alkenyl, alkenyloxy or alkoxyalkyl having 2 to 15, preferably 3 to 10, C atoms, preferably unfluorinated alkyl or alkenyl, one of $Z^{81}$ and $Z^{82}$ denotes trans-CH=CH—, trans-CF=CF— or —C≡C— and the other, independently thereof, denotes trans-CH=CH—, trans-CF=CF— or a single bond, preferably one of them denotes —C≡C— or trans-CH=CH— and the other denotes a single bond, and

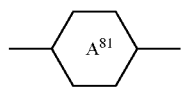

denotes

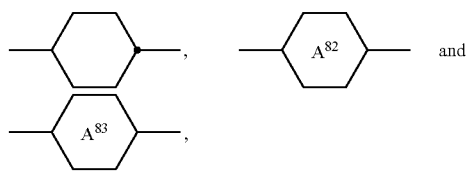

independently of one another, denote

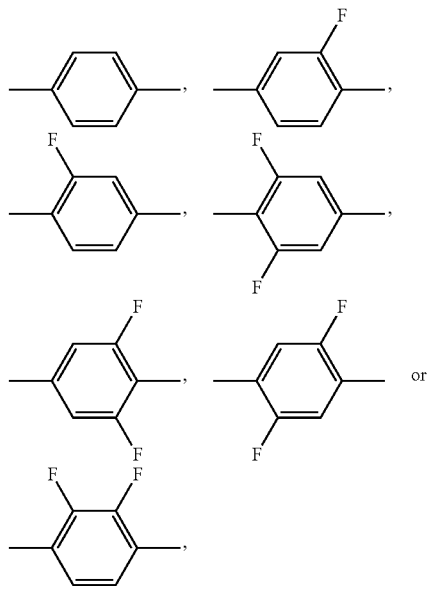

$L^{91}$ denotes $R^{91}$ or $X^{91}$,
$L^{92}$ denotes $R^{92}$ or $X^{92}$,
$R^{91}$ and $R^{92}$, independently of one another, denote H, unfluorinated alkyl or alkoxy having 1 to 15, preferably 3 to 10, C atoms or unfluorinated alkenyl, alkenyloxy or alkoxyalkyl having 2 to 15, preferably 3 to 10, C atoms, preferably unfluorinated alkyl or alkenyl, $X^{91}$ and $X^{92}$, independently of one another, denote H, F, Cl, —CN, —NCS, —SF$_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably fluorinated alkoxy, fluorinated alkenyloxy, F or Cl, and $Z^{91}$ to $Z^{93}$, independently of one another, denote trans-CH=CH—, trans-CF=CF—, —C≡C— or a single bond, preferably one or more of them denotes a single bond, and particularly preferably all denote a single bond,

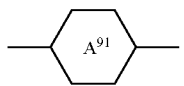

denotes

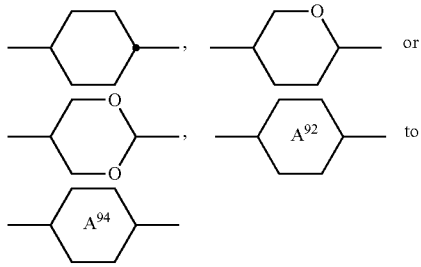

independently of one another, denote

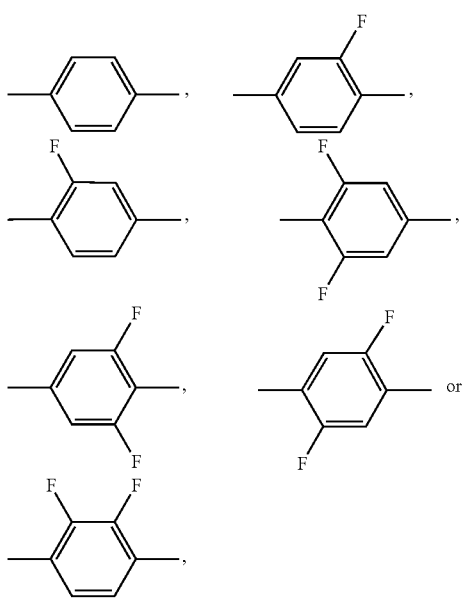

and where compounds of the formula IIIA are excluded from the compounds of the formula VI.

In a preferred embodiment of the present invention, the liquid-crystal medium comprises, more preferably predominantly consists of, even more preferably essentially consists of and very particularly preferably completely consists of one or more compounds of the formula V, preferably selected from the group of the compounds of the formulae V-1 to V-3, preferably of the formulae V-1 and/or V-2 and/or V-3, preferably of the formulae V-1 and V-2:

V-1

V-2

V-3 in which the parameters have the respective meanings indicated above for formula V and preferably $R^{51}$ denotes unfluorinated alkyl having 1 to 7 C atoms or unfluorinated alkenyl having 2 to 7 C atoms, $R^{52}$ denotes unfluorinated alkyl having 1 to 7 C atoms or unfluorinated alkenyl having 2 to 7 C atoms or unfluorinated alkoxy having 1 to 7 C atoms, $X^{51}$ and $X^{52}$, independently of one another, denote F, Cl, —$OCF_3$, —$CF_3$, —CN, —NCS or —$SF_5$, preferably F, Cl, —$OCF_3$ or —CN.

The compounds of the formula V-1 are preferably selected from the group of the compounds of the formulae V-1a to V-1d, more preferably these compounds of the formula V predominantly consist, even more preferably essentially consist and very particularly preferably completely consist thereof:

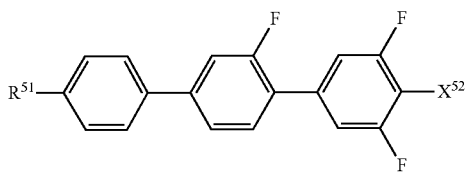
V-1a

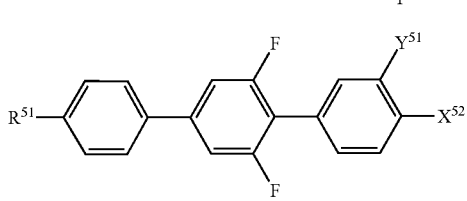
V-1b

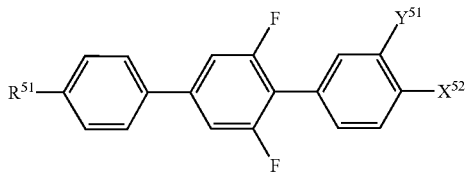
V-1c

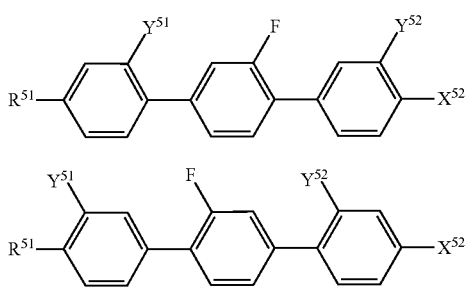
V-1d in which the parameters have the respective meanings indicated above for formula V-1 and in which $Y^{51}$ and $Y^{52}$, in each case independently of one another, denote H or F, and preferably $R^{51}$ denotes alkyl or alkenyl, and $X^{51}$ denotes F, Cl or —$OCF_3$.

The compounds of the formula V-2 are preferably selected from the group of the compounds of the formulae V-2a to V-2e and/or from the group of the compounds of the formulae V-2f and V-2g, more preferably these compounds of the formula V predominantly consist, even more preferably essentially consist and very particularly preferably completely consist thereof:

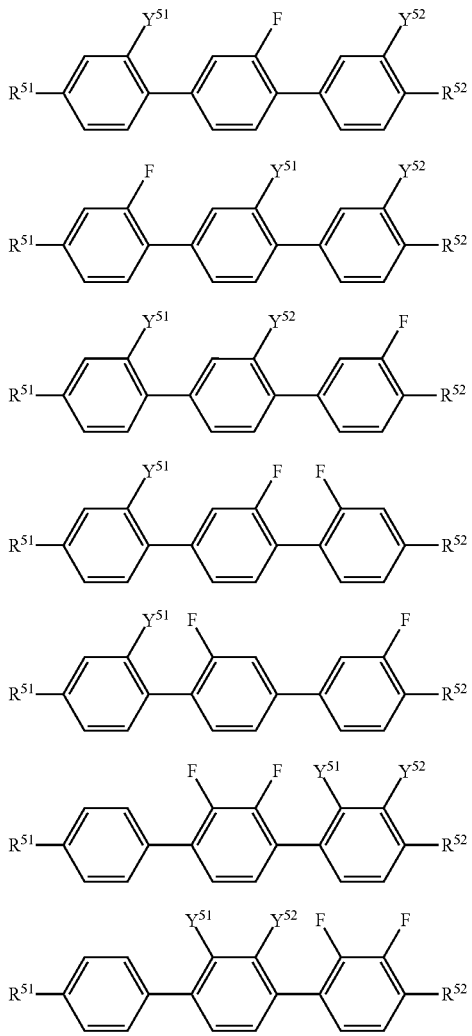

where in each case the compounds of the formula V-2a are excluded from the compounds of the formulae V-2b and V-2c, the compounds of the formula V-2b are excluded from the compounds of the formula V-2c and the compounds of the formula V-2e are excluded from the compounds of the formula V-2f, and in which the parameters have the respective meanings indicated above for formula V-1 and in which
$Y^{51}$ and $Y^{52}$, in each case independently of one another, denote H or F, and preferably
$R^{51}$ denotes unfluorinated alkyl having 1 to 7 C atoms or unfluorinated alkenyl having 2 to 7 C atoms,
$R^{52}$ denotes unfluorinated alkyl having 1 to 7 C atoms or unfluorinated alkenyl having 2 to 7 C atoms or unfluorinated alkoxy having 1 to 7 C atoms,
$X^{51}$ denotes F, Cl or —$OCF_3$, and preferably one of $Y^{51}$ and $Y^{52}$ denotes H and the other denotes H or F, preferably likewise denotes H.

The compounds of the formula V-3 are preferably compounds of the formula V-3a:

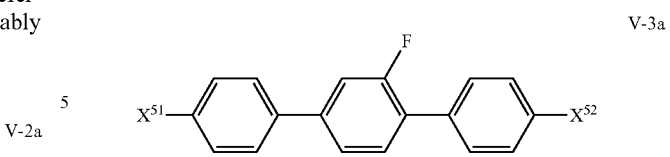

in which the parameters have the respective meanings indicated above for formula V-1 and in which preferably
$X^{51}$ denotes F or Cl, preferably F,
$X^{52}$ denotes F, Cl or $OCF_3$, preferably $OCF_3$.

In an even more preferred embodiment of the present invention, the compounds of the formula V are selected from the group of the compounds V-1a to V-1d, preferably selected from the group of the compounds V-1c and V-1d, more preferably these compounds of the formula V predominantly consist, even more preferably essentially consist and very particularly preferably completely consist thereof:

The compounds of the formula V-1a are preferably selected from the group of the compounds of the formulae V-1a-1 and V-1a-2, more preferably these compounds of the formula V predominantly consist, even more preferably essentially consist and very particularly preferably completely consist thereof:

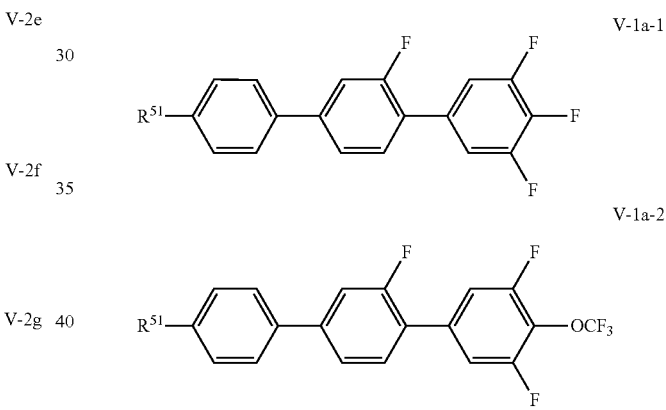

in which
$R^{51}$ has the meaning indicated above and preferably denotes $C_nH_{2n+1}$, in which
n denotes an integer in the range from 0 to 7, preferably in the range from 1 to 5 and particularly preferably 3 or 7.

The compounds of the formula V-1b are preferably compounds of the formula V-1b-1:

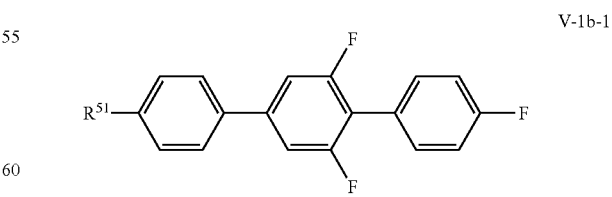

in which
$R^{51}$ has the meaning indicated above and preferably denotes $C_nH_{2n+1}$, in which
n denotes an integer in the range from 0 to 15, preferably in the range from 1 to 7 and particularly preferably 1 to 5.

The compounds of the formula V-1c are preferably selected from the group of the compounds of the formulae V-1c-1 to V-1c-4, preferably selected from the group of the compounds of the formulae V-1c-1 and V-1c-2, more preferably these compounds of the formula V predominantly consist, even more preferably essentially consist and very particularly preferably completely consist thereof:

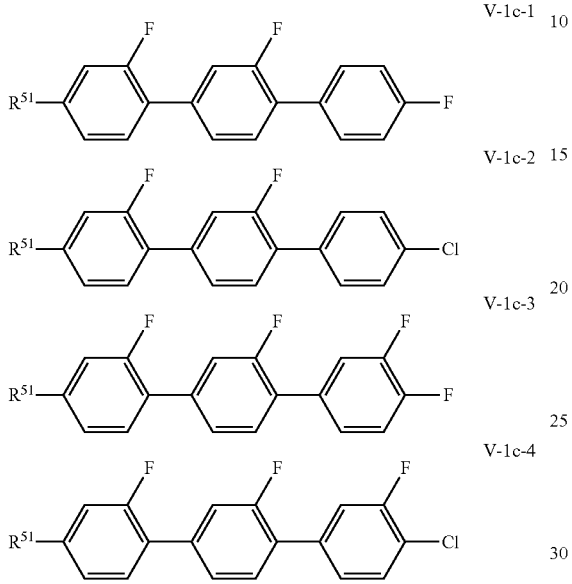

in which
R$^{51}$ has the meaning indicated above and preferably denotes C$_n$H$_{2n+1}$, in which
n denotes an integer in the range from 0 to 15, preferably in the range from 1 to 7 and particularly preferably 1 to 5.

The compounds of the formula V-1d are preferably selected from the group of the compounds of the formulae V-1d-1 and V-1d-2, preferably the compound of the formula V-1d-2, more preferably these compounds of the formula V predominantly consist, even more preferably essentially consist and very particularly preferably completely consist thereof:

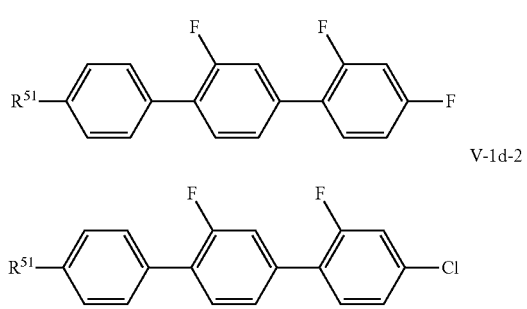

in which
R$^{51}$ has the meaning indicated above and preferably denotes C$_n$H$_{2n+1}$, in which
n denotes an integer in the range from 0 to 15, preferably in the range from 1 to 7 and particularly preferably 1 to 5.

The compounds of the formula V-2a are preferably selected from the group of the compounds of the formulae V-2a-1 and V-2a-2, preferably the compounds of the formula V-2a-1, more preferably these compounds of the formula V predominantly consist, even more preferably essentially consist and very particularly preferably completely consist thereof:

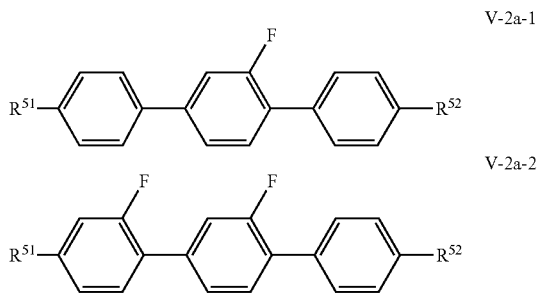

in which
R$^{51}$ has the meaning indicated above and preferably denotes C$_n$H$_{2n+1}$ or CH$_2$=CH—(CH$_2$)$_z$, and
R$^{52}$ has the meaning indicated above and preferably denotes C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

Preferred combinations of (R$^{51}$ and R$^{52}$), in particular in the case of formula V-2a-1, are (C$_n$H$_{2n+1}$ and C$_m$H$_{2m+1}$), (C$_n$H$_{2n+1}$ and O—C$_m$H$_{2m+1}$), (CH$_2$=CH—(CH$_2$)$_z$ and C$_m$H$_{2m+1}$), (CH$_2$=CH—(CH$_2$)$_z$ and O—C$_m$H$_{2m+1}$) and (C$_n$H$_{2n+1}$ and (CH$_2$)$_z$—CH=CH$_2$).

Preferred compounds of the formula V-2b are the compounds of the formula V-2b-1:

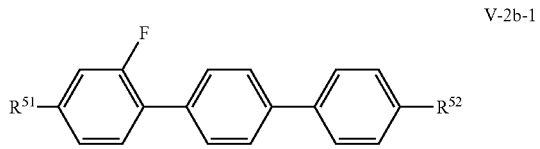

in which
R$^{51}$ has the meaning indicated above and preferably denotes C$_n$H$_{2n+1}$ or CH$_2$=CH—(CH$_2$)$_z$, and
R$^{52}$ has the meaning indicated above and preferably denotes C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combination of (R$^{51}$ and R$^{52}$) here is, in particular, (C$_n$H$_{2n+1}$ and C$_m$H$_{2m+1}$).

Preferred compounds of the formula V-2c are the compounds of the formula V-2c-1:

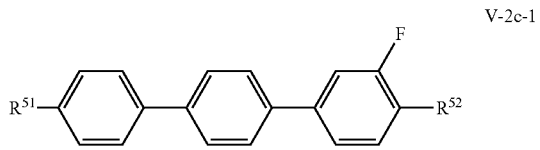

in which

R$^{51}$ has the meaning indicated above and preferably denotes C$_n$H$_{2n+1}$ or CH$_2$=CH—(CH$_2$)$_z$, and R$^{52}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combination of (R$^{51}$ and R$^{52}$) here is, in particular, (C$_n$H$_{2n+1}$ and C$_m$H$_{2m+1}$).

Preferred compounds of the formula V-2d are the compounds of the formula V-2d-1:

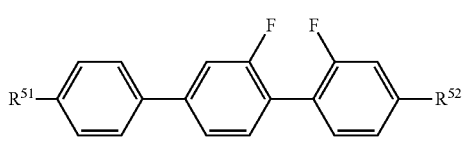

V-2d-1 in which

R$^{51}$ has the meaning indicated above and preferably denotes C$_n$H$_{2n+1}$ or CH$_2$=CH—(CH$_2$)$_z$, and R$^{52}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combination of (R$^{51}$ and R$^{52}$) here is, in particular, (C$_n$H$_{2n+1}$ and C$_m$H$_{2m+1}$).

Preferred compounds of the formula V-2e are the compounds of the formula V-2e-1:

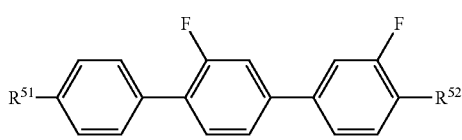

V-2e-1 in which

R$^{51}$ has the meaning indicated above and preferably denotes C$_n$H$_{2n+1}$ or CH$_2$=CH—(CH$_2$)$_z$, and R$^{52}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combination of (R$^{51}$ and R$^{52}$) here is, in particular, (C$_n$H$_{2n+1}$ and O—C$_m$H$_{2m+1}$).

Preferred compounds of the formula V-2f are the compounds of the formula V-2f-1:

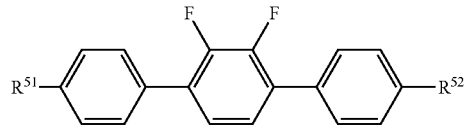

V-2f-1 in which

R$^{51}$ has the meaning indicated above and preferably denotes C$_n$H$_{2n+1}$ or CH$_2$=CH—(CH$_2$)$_z$, and R$^{52}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of (R$^{51}$ and R$^{52}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and C$_m$H$_{2m+1}$).

Preferred compounds of the formula V-2g are the compounds of the formula V-2g-1:

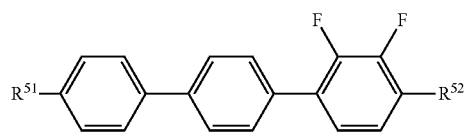

V-2g-1 in which

R$^{51}$ has the meaning indicated above and preferably denotes C$_n$H$_{2n+1}$ or CH$_2$=CH—(CH$_2$)$_z$, and R$^{52}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of (R$^{51}$ and R$^{52}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and O—C$_m$H$_{2m+1}$).

The compounds of the formula VI are preferably selected from the group of the compounds of the formulae VI-1 to VI-4, more preferably these compounds of the formula VI predominantly consist, even more preferably essentially consist and very particularly preferably completely consist thereof:

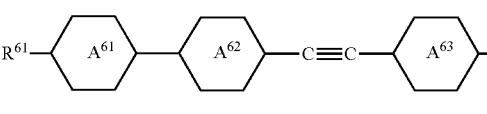

VI-1

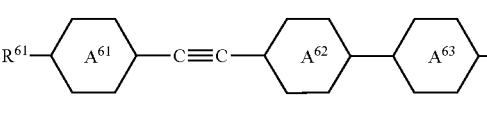

VI-2

-continued

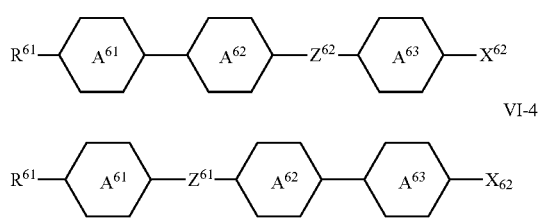

in which
$Z^{61}$ and $Z^{62}$ denote trans-CH=CH— or trans-CF=CF—, preferably trans-CH=CH—, and the other parameters have the meaning given above under formula VI and preferably
$R^{61}$ and $R^{62}$, independently of one another, denote H, unfluorinated alkyl or alkoxy having 1 to 7 C atoms or unfluorinated alkenyl having 2 to 7 C atoms,
$X^{62}$ denotes F, Cl, —CN or —NCS, preferably —NCS,
and one of

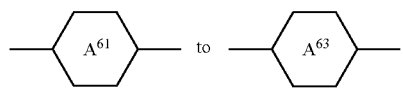

denotes

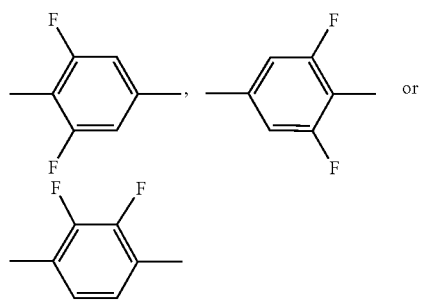

and the others, independently of one another, denote

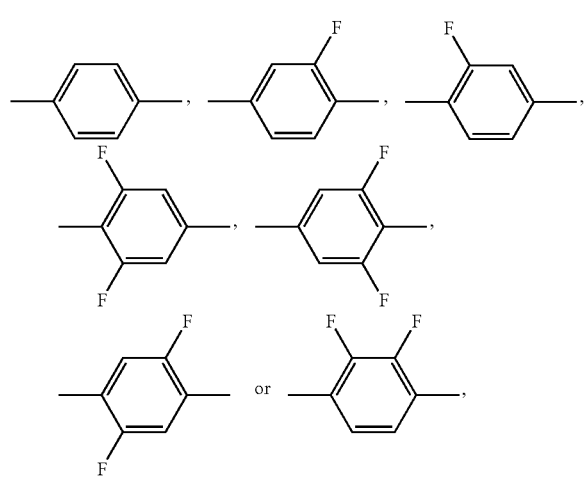

preferably

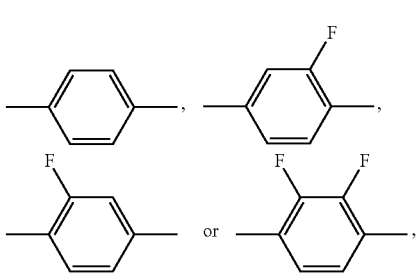

and preferably
$R^{61}$ denotes $C_nH_{2n+1}$ or $CH_2=CH-(CH_2)_z$, and
$R^{62}$ denotes $C_mH_{2m+1}$ or $O-C_mH_{2m+1}$ or $(CH_2)_z-CH=CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2,
with the condition that compounds of formula VI-2 are excluded from compounds of formula VI-1.

The compounds of the formula VI-1 are preferably selected from the group of the compounds of the formulae VI-1a and VI-1b, preferably selected from the compounds of the formula VI-1a, more preferably these compounds of the formula VI predominantly consist, even more preferably essentially consist and very particularly preferably completely consist thereof:

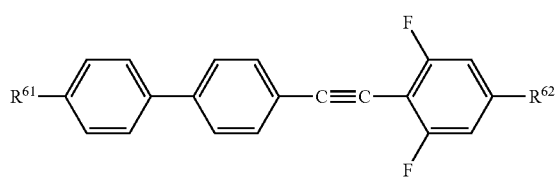

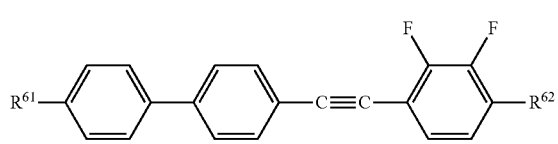

in which
$R^{61}$ has the meaning indicated above and preferably denotes $C_nH_{2n+1}$ or $CH_2=CH-(CH_2)_z$, and
$R^{62}$ has the meaning indicated above and preferably denotes $C_mH_{2m+1}$ or $O-C_mH_{2m+1}$ or $(CH_2)_z-CH=CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{61}$ and $R^{62}$) here are, in particular, ($C_nH_{2n+1}$ and $C_mH_{2m+1}$) and ($C_nH_{2n+1}$ and $O-C_mH_{2m+1}$), in the case of formula VI-1a particularly preferably ($C_nH_{2n+1}$ and $C_mH_{2m+1}$) and in the case of formula VI-1b particularly preferably ($C_nH_{2n+1}$ and $O-C_mH_{2m+1}$).

The compounds of the formula VI-3 are preferably compounds of the formula VI-3a:

VI-3a

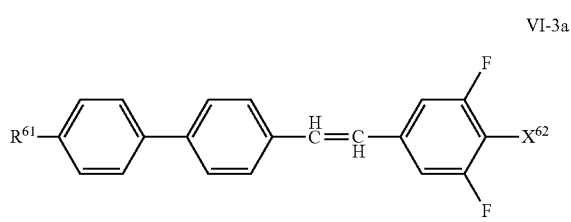

in which the parameters have the meaning given above under formula VI-3 and preferably
R$^{61}$ has the meaning indicated above and preferably denotes C$_n$H$_{2n+1}$, in which
n denotes an integer in the range from 0 to 7, preferably in the range from 1 to 5, and
X$^{62}$ denotes —F, —Cl, —OCF$_3$, —CN or —NCS, particularly preferably —NCS.

The compounds of the formula VI-4 are preferably compounds of the formula VI-4a:

VI-4a

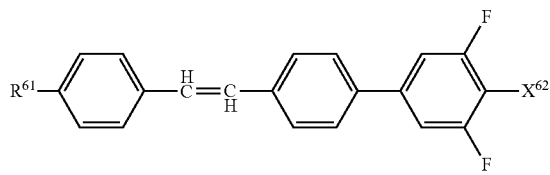

in which the parameters have the meaning given above under formula VI-4 and preferably
R$^{61}$ has the meaning indicated above and preferably denotes C$_n$H$_{2n+1}$, in which
n denotes an integer in the range from 0 to 7, preferably in the range from 1 to 5, and
X$^{62}$ denotes F, Cl, OCF$_3$, —CN or —NCS, particularly preferably —NCS.

Further preferred compounds of the formula VI are the compounds of the following formulae:

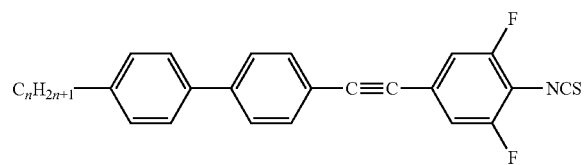

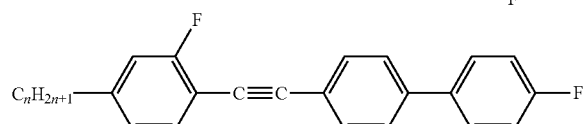

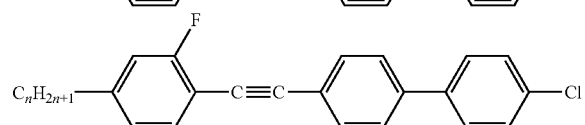

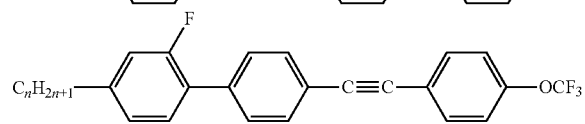

in which
n denotes an integer in the range from 0 to 7, preferably in the range from 1 to 5.

The compounds of the formula VII are preferably selected from the group of the compounds of the formulae VII-1 to VII-6, more preferably these compounds of the formula VII predominantly consist, even more preferably essentially consist and very particularly preferably completely consist thereof:

VII-1

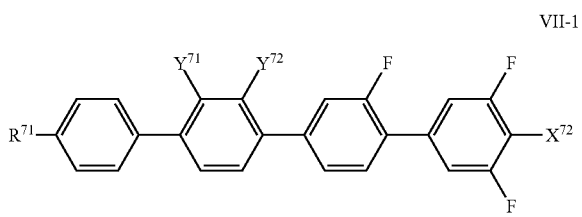

VII-2

VII-3

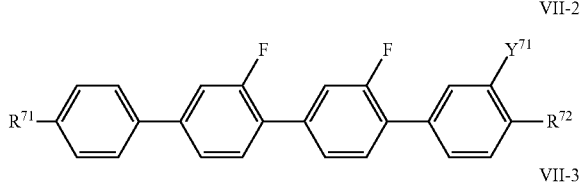

VII-4

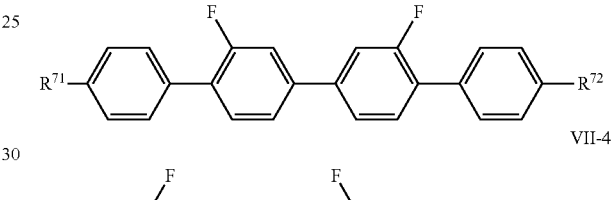

VII-5

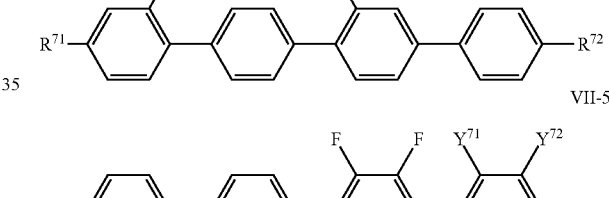

VII-6

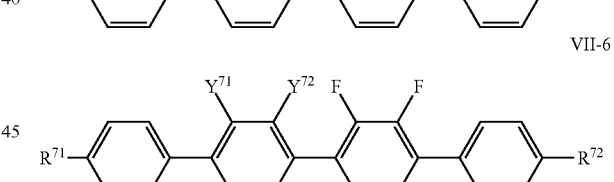

where the compounds of the formula VII-5 are excluded from the compounds of the formula VII-6, and
in which the parameters have the respective meanings indicated above for formula VII, and preferably
R$^{71}$ denotes unfluorinated alkyl or alkoxy, each having 1 to 7 C atoms, or unfluorinated alkenyl having 2 to 7 C atoms,
R$^{72}$ denotes unfluorinated alkyl or alkoxy, each having 1 to 7 C atoms, or unfluorinated alkenyl having 2 to 7 C atoms, and
X$^{72}$ denotes F, Cl or —OCF$_3$, preferably F, and particularly preferably
R$^{71}$ has the meaning indicated above and preferably denotes C$_n$H$_{2n+1}$ or CH$_2$=CH—(CH$_2$)$_z$, and
R$^{72}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The compounds of the formula VII-1 are preferably selected from the group of the compounds of the formulae VII-1a to VII-1d, more preferably these compounds of the formula VII-1 predominantly consist, even more preferably essentially consist and very particularly preferably completely consist thereof:

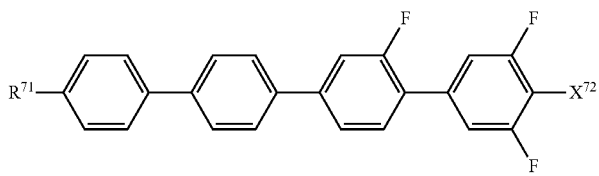
VII-1a

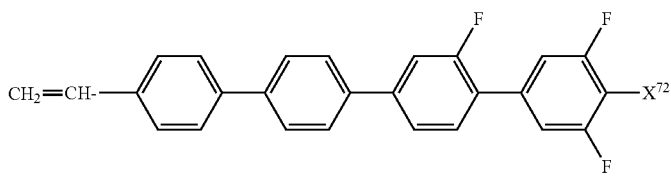
VII-1b

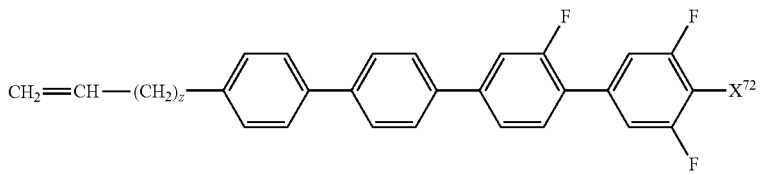
VII-1c

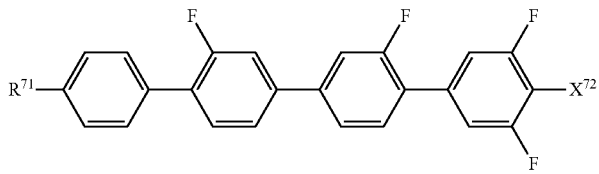
VII-1d

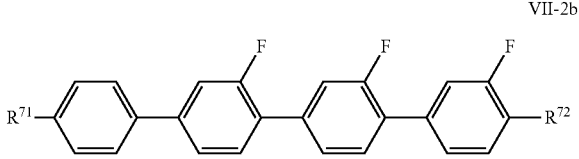
VII-2b in which $X^{72}$ has the meaning given above for formula VII-2 and $R^{71}$ has the meaning indicated above and preferably denotes $C_nH_{2n+1}$, in which n denotes 1 to 7, preferably 2 to 6, particularly preferably 2, 3 or 5, and z denotes 0, 1, 2, 3 or 4, preferably 0 or 2, and $X^{72}$ preferably denotes F.

The compounds of the formula VII-2 are preferably selected from the group of the compounds of the formulae VII-2a and VII-2b, preferably of the formula VII-2a, more preferably these compounds of the formula VII-2 predominantly consist, even more preferably essentially consist and very particularly preferably completely consist thereof:

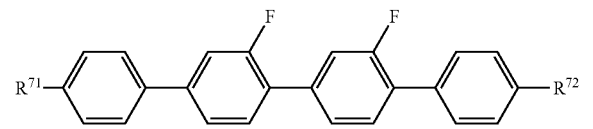
VII-2a in which $R^{71}$ has the meaning indicated above and preferably denotes $C_nH_{2n+1}$ or $CH_2=CH-(CH_2)_z$, and $R^{72}$ has the meaning indicated above and preferably denotes $C_mH_{2m+1}$ or $O-C_mH_{2m+1}$ or $(CH_2)_z-CH=CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and $O-C_mH_{2m+1}$), particularly preferably ($C_nH_{2n+1}$ and $C_mH_{2m+1}$).

The compounds of the formula VII-3 are preferably compounds of the formula VII-3a:

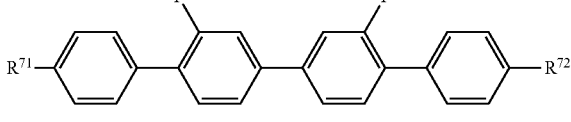
VII-3a in which $R^{71}$ has the meaning indicated above and preferably denotes $C_nH_{2n+1}$ or $CH_2=CH—(CH_2)_z$, and $R^{72}$ has the meaning indicated above and preferably denotes $C_mH_{2m+1}$ or $O—C_mH_{2m+1}$ or $(CH_2)_z—CH=CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and $O—C_mH_{2m+1}$), particularly preferably ($C_nH_{2n+1}$ and $C_mH_{2m+1}$).

The compounds of the formula VII-4 are preferably compounds of the formula VII-4a:

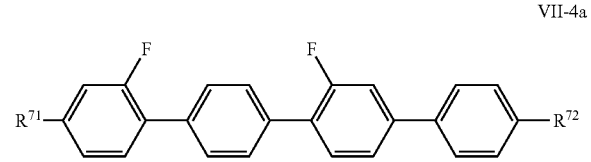

VII-4a in which $R^{71}$ has the meaning indicated above and preferably denotes $C_nH_{2n+1}$ or $CH_2=CH—(CH_2)_z$, and $R^{72}$ has the meaning indicated above and preferably denotes $C_mH_{2m+1}$ or $O—C_mH_{2m+1}$ or $(CH_2)_z—CH=CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and $O—C_mH_{2m+1}$), particularly preferably ($C_nH_{2n+1}$ and $C_mH_{2m+1}$).

The compounds of the formula VII-5 are preferably selected from the group of the compounds of the formulae VII-5a and VII-5b, preferably of the formula VII-5a, more preferably these compounds of the formula VII-5 predominantly consist, even more preferably essentially consist and very particularly preferably completely consist thereof:

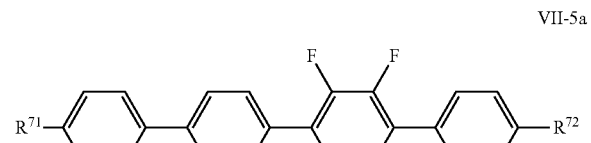

VII-5a

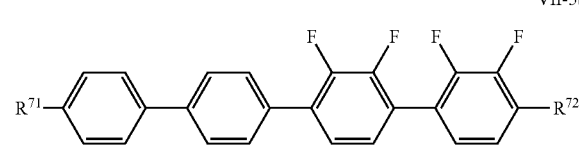

VII-5b in which $R^{71}$ has the meaning indicated above and preferably denotes $C_nH_{2n+1}$ or $CH_2=CH—(CH_2)_z$, and $R^{72}$ has the meaning indicated above and preferably denotes $C_mH_{2m+1}$ or $O—C_mH_{2m+1}$ or $(CH_2)_z—CH=CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and $O—C_mH_{2m+1}$), particularly preferably ($C_nH_{2n+1}$ and $C_mH_{2m+1}$).

The compounds of the formula VII-6 are preferably selected from the group of the compounds of the formulae VII-6a and VII-6b, more preferably these compounds of the formula VII-6 predominantly consist, even more preferably essentially consist and very particularly preferably completely consist thereof:

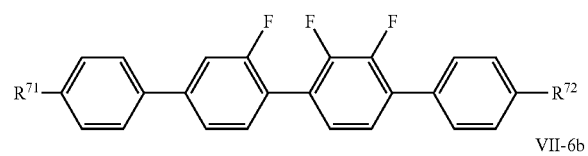

VII-6a

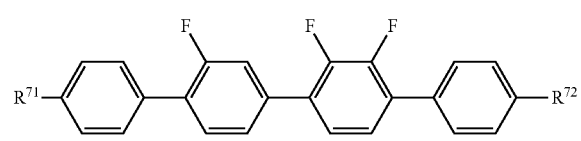

VII-6b in which $R^{71}$ has the meaning indicated above and preferably denotes $C_nH_{2n+1}$ or $CH_2=CH—(CH_2)_z$, and $R^{72}$ has the meaning indicated above and preferably denotes $C_mH_{2m+1}$ or $O—C_mH_{2m+1}$ or $(CH_2)_z—CH=CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and $O—C_mH_{2m+1}$), particularly preferably ($C_nH_{2n+1}$ and $C_mH_{2m+1}$).

The compounds of the formula VIII are preferably selected from the group of the compounds of the formulae VIII-1 to VIII-3, more preferably these compounds of the formula VIII predominantly consist, even more preferably essentially consist and very particularly preferably completely consist thereof:

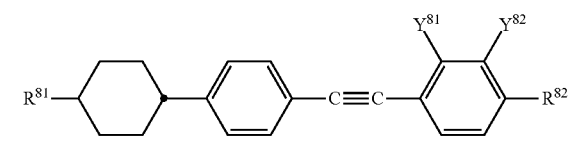

VIII-1

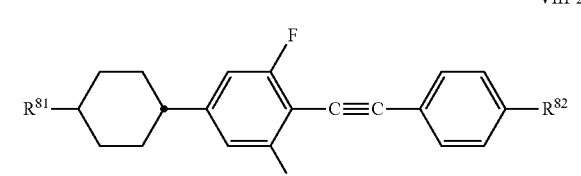

VIII-2

VIII-3

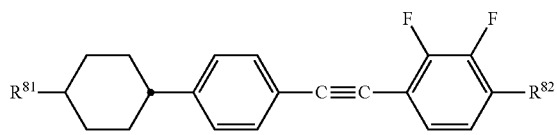

in which
one of
$Y^{81}$ and $Y^{82}$ denotes H and the other denotes H or F, and
$R^{81}$ has the meaning indicated above and preferably denotes
$C_nH_{2n+1}$ or $CH_2=CH-(CH_2)_z$, and
$R^{82}$ has the meaning indicated above and preferably denotes
$C_mH_{2m+1}$ or $O-C_mH_{2m+1}$ or $(CH_2)_z-CH=CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$) and ($C_nH_{2n+1}$ and $O-C_mH_{2m+1}$), particularly preferably ($C_nH_{2n+1}$ and $C_mH_{2m+1}$).

The compounds of the formula VIII-1 are preferably selected from the group of the compounds of the formulae VIII-1a to VIII-1c, more preferably these compounds of the formula VIII-1 predominantly consist, even more preferably essentially consist and very particularly preferably completely consist thereof:

VIII-1a

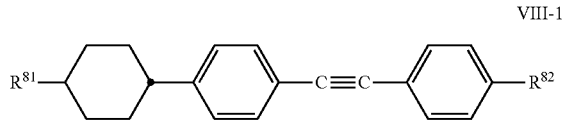

VIII-1b

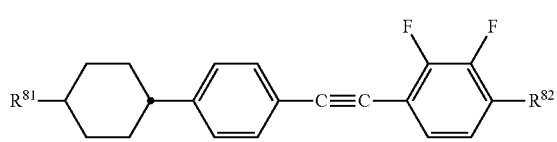

VIII-1c

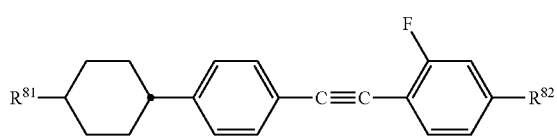

in which
$R^{81}$ has the meaning indicated above and preferably denotes
$C_nH_{2n+1}$ or $CH_2=CH-(CH_2)_z$, and
$R^{82}$ has the meaning indicated above and preferably denotes
$C_mH_{2m+1}$ or $O-C_mH_{2m+1}$ or $(CH_2)_z-CH=CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$) and ($C_nH_{2n+1}$ and $O-C_mH_{2m+1}$), particularly preferably ($C_nH_{2n+1}$ and $C_mH_{2m+1}$).

The compounds of the formula VIII-2 are preferably compounds of the formula VIII-2a:

VIII-2a

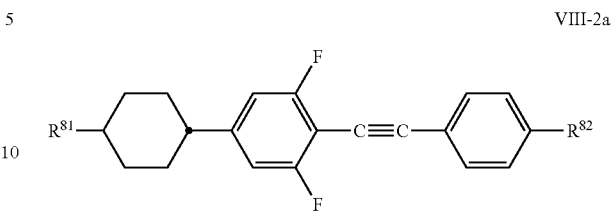

in which
$R^{81}$ has the meaning indicated above and preferably denotes
$C_nH_{2n+1}$ or $CH_2=CH-(CH_2)_z$, and
$R^{82}$ has the meaning indicated above and preferably denotes
$C_mH_{2m+1}$ or $O-C_mH_{2m+1}$ or $(CH_2)_z-CH=CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$), ($C_nH_{2n+1}$ and $O-C_mH_{2m+1}$) and ($CH_2=CH-(CH_2)_z$ and $C_mH_{2m+1}$), particularly preferably ($C_nH_{2n+1}$ and $C_mH_{2m+1}$).

The compounds of the formula VIII-3 are preferably compounds of the formula VIII-3a:

VIII-3a

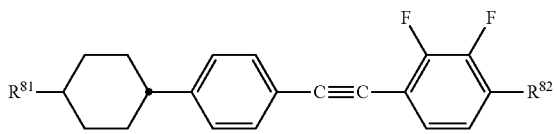

in which
$R^{81}$ has the meaning indicated above and preferably denotes
$C_nH_{2n+1}$ or $CH_2=CH-(CH_2)_z$, and
$R^{82}$ has the meaning indicated above and preferably denotes
$C_mH_{2m+1}$ or $O-C_mH_{2m+1}$ or $(CH_2)_z-CH=CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$) and ($C_nH_{2n+1}$ and $O-C_mH_{2m+1}$).

The compounds of the formula IX are preferably selected from the group of the compounds of the formulae IX-1 to IX-3, more preferably these compounds of the formula IX predominantly consist, even more preferably essentially consist and very particularly preferably completely consist thereof:

IX-1

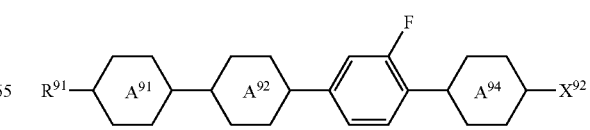

-continued

IX-2
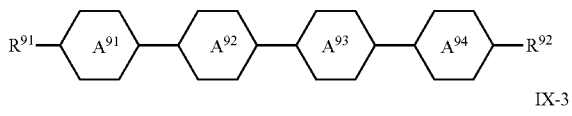

IX-3
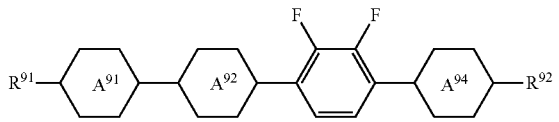

in which the parameters have the respective meaning indicated above under formula IX and preferably one of

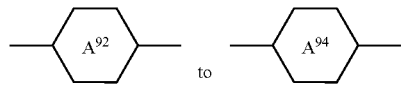

denotes

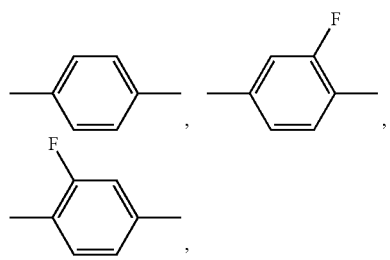

and
in which
R$^{91}$ has the meaning indicated above and preferably denotes C$_n$H$_{2n+1}$ or CH$_2$=CH—(CH$_2$)$_z$, and
R$^{92}$ has the meaning indicated above and preferably denotes C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{91}$ and R$^{92}$) here are, in particular, (C$_n$H$_{2n+1}$ and C$_m$H$_{2m+1}$) and (C$_n$H$_{2n+1}$ and O—C$_m$H$_{2m+1}$).

The compounds of the formula IX-1 are preferably selected from the group of the compounds of the formulae IX-1a to IX-1e, more preferably these compounds of the formula IX-1 predominantly consist, even more preferably essentially consist and very particularly preferably completely consist thereof:

IX-1a
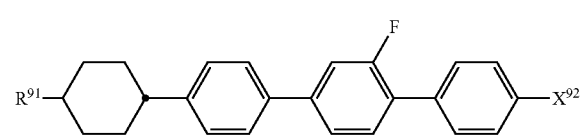

-continued

IX-1b

IX-1c
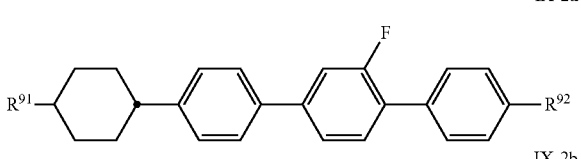

IX-1d

IX-1e
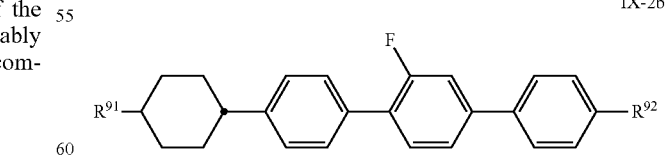

in which the parameters have the meaning given above and preferably
R$^{91}$ has the meaning indicated above and preferably denotes C$_n$H$_{2n+1}$, and
n denotes an integer in the range from 0 to 15, preferably in the range from 1 to 7 and particularly preferably 1 to 5, and
X$^{92}$ preferably denotes F or Cl.

The compounds of the formula IX-2 are preferably selected from the group of the compounds of the formulae IX-2a and IX-2b, more preferably these compounds of the formula IX-2 predominantly consist, even more preferably essentially consist and very particularly preferably completely consist thereof:

IX-2a

IX-2b
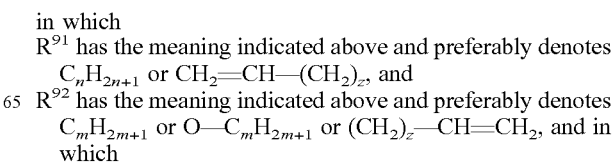

in which
R$^{91}$ has the meaning indicated above and preferably denotes C$_n$H$_{2n+1}$ or CH$_2$=CH—(CH$_2$)$_z$, and
R$^{92}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combination of ($R^{91}$ and $R^{92}$) here is, in particular, ($C_nH_{2n+1}$ and $C_mH_{2m+1}$).

The compounds of the formula IX-3 are preferably compounds of the formulae IX-3a and IX-3b:

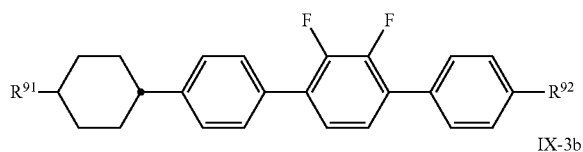

IX-3a

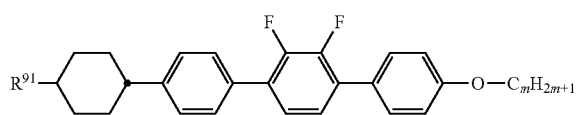

IX-3b in which $R^{91}$ has the meaning indicated above and preferably denotes $C_nH_{2n+1}$ or $CH_2=CH-(CH_2)_z$, and $R^{92}$ has the meaning indicated above and preferably denotes $C_mH_{2m+1}$ or $O-C_mH_{2m+1}$ or $(CH_2)_z-CH=CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{91}$ and $R^{92}$) here are, in particular, ($C_nH_{2n+1}$ and $C_mH_{2m+1}$) and ($C_nH_{2n+1}$ and $O-C_mH_{2m+1}$), particularly preferably ($C_nH_{2n+1}$ and $O-C_mH_{2m+1}$).

The definitions of the abbreviations (acronyms) used for the compounds in the present application are indicated below in Table D or are evident from Tables A to C.

In a preferred embodiment of the present invention, the liquid-crystal medium, or component A of the liquid-crystal medium, comprises one or more compounds of the formulae I-1 and/or I-2 and/or I-3 and/or I-4.

The liquid-crystal medium, or component A of the liquid-crystal medium, preferably comprises one or more compounds selected from the compounds of the formulae I-1a-1 to I-1a-12, particularly preferably of the formula I-1a-2, very particularly preferably one or more compounds of the formula I-1a-2 and one or more compounds selected from the group of the compounds of the formula I-1a-1 and formulae I-1a-3 to I-1a-12, and one or more compounds of the formulae I-1 b-1 to I-1b-12 and/or I-2 and/or I-3 and/or I-4.

In a further preferred embodiment of the present invention, the liquid-crystal medium, or component A of the liquid-crystal medium, comprises one or more compounds selected from the group of the compounds of the formulae I-1 b-1 to I-1b-12, particularly preferably selected from the group of the compounds of the formulae I-1 b-5 and/or I-1 b-7 and/or I-1 b-8 and/or I-1 b-9 and/or I-1b-10, and one or more compounds selected from the group of the compounds of the formulae I-1a-1 to I-1a-12, preferably of the formula I-1a-2, and/or one or more compounds of the formulae I-2 and/or I-3 and/or I-4.

In a further preferred embodiment of the present invention, the liquid-crystal medium, or component A of the liquid-crystal medium, comprises one or more compounds of the formula I-2 and one or more compounds of the formula I-1, preferably of the formula I-1a, preferably of the formulae I-1a-2, and/or I-1b, and/or one or more compounds of the formulae I-3 and/or I-4.

In a further preferred embodiment of the present invention, the liquid-crystal medium, or component A of the liquid-crystal medium, comprises one or more compounds of the formula I-3 and one or more compounds of the formula I-1, preferably of the formula I-1a, preferably of the formula I-1a-2, and/or I-1b, and/or one or more compounds of the formulae I-2 and/or I-4.

In a further preferred embodiment of the present invention, the liquid-crystal medium, or component A of the liquid-crystal medium, comprises one or more compounds of the formula I-4 and one or more compounds of the formula I-1, preferably of the formula I-1a, preferably of the formula I-1a-2, and/or I-1b, and/or one or more compounds of the formulae I-2 and/or I-3.

In a preferred embodiment of the present invention, the medium comprises one or more dielectrically positive compounds of the formula V-1 having a dielectric anisotropy of greater than 3.

In a preferred embodiment of the present invention, the medium comprises one or more compounds of the formula IA.

In a preferred embodiment of the present invention, the medium comprises one or more compounds of the formula VI.

In a preferred embodiment of the present invention, the medium comprises one or more compounds of the formula I and/or IA and VI.

In a further preferred embodiment of the present invention, the medium comprises one or more compounds of the formula VII.

In this application, "comprise" in connection with compositions means that the entity in question, i.e. the medium or the component, comprises the component or components or compound or compounds indicated, preferably in a total concentration of 10% or more and very preferably 20% or more.

In this connection, "predominantly consist of" means that the entity in question comprises 55% or more, preferably 60% or more and very preferably 70% or more, of the component or components or compound or compounds indicated.

In this connection, "essentially consist of" means that the entity in question comprises 80% or more, preferably 90% or more and very preferably 95% or more, of the component or components or compound or compounds indicated.

In this connection, "completely consist of" means that the entity in question comprises 98% or more, preferably 99% or more and very preferably 100.0% of the component or components or compound or compounds indicated.

Other mesogenic compounds which are not explicitly mentioned above can optionally and advantageously also be used in the media in accordance with the present invention. Such compounds are known to the person skilled in the art.

The liquid crystal medium comprises compounds of formula M in a total concentration of 1% to 30%, preferably of 2% to 20% and particularly preferably of 4 to 10%.

In a preferred embodiment of the present invention, the liquid crystal medium comprises compounds of formula IA in a total concentration of 5% to 80%, more preferably 10% to 60% and particularly preferably 20% to 40% of compounds of the formula IA.

In a preferred embodiment of the present invention, the liquid-crystal medium comprises a total concentration of 10% to 90%, more preferably 40% to 80% and particularly preferably 50% to 70% of compounds of formula I and/or VI of the mixture as a whole.

In the embodiment of the present invention in which the liquid-crystal media comprise one or more compounds selected from the group of the compounds of the formulae IIA and IIB, the further compounds are preferably employed as follows.

The compounds selected from the group of the compounds of the formulae IIA and IIB are preferably used in a total concentration of 1% to 30%, more preferably 2% to 20%, even more preferably 3% to 18% and very preferably 4% to 16%, of the mixture as a whole.

The compounds of the formula IV are preferably used in a total concentration of 0% to 20%, more preferably 2% to 15%, and very preferably 5% to 10%, of the mixture as a whole.

In the embodiment of the present invention in which the liquid-crystal media comprise one or more compounds selected from the group of the compounds of the formulae IIIA and IIIB, the further compounds are preferably employed as follows.

The compounds selected from the group of the compounds of the formulae IIIA and IIIB are preferably used in a total concentration of 1% to 60%, more preferably 5% to 55%, even more preferably 7% to 50% and very preferably 10% to 45%, of the mixture as a whole.

If the liquid-crystal media comprise only one or more compounds of the formula IIIA, but no compounds of the formula IIIB, the compounds of the formula IIIA are preferably used in a total concentration of 10% to 60%, more preferably 20% to 55%, even more preferably 30% to 50% and very preferably 35% to 45%, of the mixture as a whole.

If the liquid-crystal media comprise only one or more compounds of the formula IIIB, but no compounds of the formula IIIA, the compounds of the formula IIIB are preferably used in a total concentration of 5% to 45%, more preferably 10% to 40%, even more preferably 15% to 35% and very preferably 20% to 30%, of the mixture as a whole.

If the liquid-crystal media comprise both one or more compounds of the formula IIIA and one or more compounds of the formula IIIB, the compounds of the formula IIIA are preferably used in a total concentration of 5% to 50%, more preferably 10% to 45%, even more preferably 15% to 30% and very preferably 20% to 25%, of the mixture as a whole and the compounds of the formula IIIB are preferably used in a total concentration of 1% to 35%, more preferably 5% to 30%, even more preferably 7% to 25% and very preferably 10% to 20%, of the mixture as a whole.

The compounds of the formula IV are preferably used in a total concentration of 1% to 20%, more preferably 2% to 15%, even more preferably 3% to 12% and very preferably 5% to 10%, of the mixture as a whole.

In a particularly preferred embodiment of the present invention, the liquid-crystalline media comprise one or more compounds of the formula V and one or more compounds of the formula VI.

In a further particularly preferred embodiment of the present invention, the liquid-crystalline media comprise one or more compounds of the formula V and one or more compounds of the formula VII.

The liquid-crystalline media in accordance with the present invention likewise preferably comprise one or more compounds of the formula V, one or more compounds of the formula VI and one or more compounds of the formula VIII.

If the liquid-crystalline media in accordance with the present application comprise one or more compounds of the formula V, the concentration of these compounds is preferably in total 10 to 30%, preferably 15 to 25% and particularly preferably 18 to 22%.

If the liquid-crystalline media in accordance with the present application comprise one or more compounds of the formula VI, the concentration of these compounds is preferably in total 25 to 85%, preferably 45 to 70% and particularly preferably 50 to 60%.

If the liquid-crystalline media in accordance with the present application comprise one or more compounds of the formula VII, the concentration of these compounds is preferably in total 0.5 to 10%, preferably 1 to 8% and particularly preferably 2 to 5%.

If the liquid-crystalline media in accordance with the present application comprise one or more compounds of the formula VIII, the concentration of these compounds is preferably in total 1 to 20%, preferably 2 to 15% and particularly preferably 5 to 10%.

If the liquid-crystalline media in accordance with the present application comprise one or more compounds of the formula IX, the concentration of these compounds is preferably in total 1 to 20%, preferably 2 to 15% and particularly preferably 5 to 10%.

In further preferred embodiments, the media according to the present invention comprise
- one or more compounds of formula CCP-V-m, preferably CCP-V-1;
- one or more compounds of the formula CPP-n-m;
- one or more compounds selected from the group of compounds of the formulae formula PZP-n-N and PZG-n-N, preferably PZG-4-N;
- one or more compounds of the formula PVG-n-S, preferably PVG-3-S
- one or more compounds of the formula PGUQU-n-F, preferably selected from the compounds PGUQU-3-F, PGUQU-4-F and PGUQU-5-F.

In the present application, the expression dielectrically positive describes compounds or components where $\Delta\varepsilon > 3.0$, dielectrically neutral describes those where $-1.5 \leq \Delta\varepsilon \leq 3.0$ and dielectrically negative describes those where $\Delta\varepsilon < -1.5$. $\Delta\varepsilon$ is determined at a frequency of 1 kHz and at 20° C. The dielectric anisotropy of the respective compound is determined from the results of a solution of 10% of the respective individual compound in a nematic host mixture. If the solubility of the respective compound in the host mixture is less than 10%, the concentration is reduced to 5%. The capacitances of the test mixtures are determined both in a cell having homeotropic alignment and in a cell having homogeneous alignment. The cell thickness of both types of cells is approximately 20 μm. The voltage applied is a rectangular wave having a frequency of 1 kHz and an effective value of typically 0.5 V to 1.0 V, but it is always selected to be below the capacitive threshold of the respective test mixture.

The following definitions apply here.

$$\Delta\varepsilon \equiv (\varepsilon_\| - \varepsilon_\perp) \text{ and}$$

$$\varepsilon_{average} \equiv (\varepsilon_\| + 2\varepsilon_\perp)/3.$$

The host mixture used for dielectrically positive compounds is mixture ZLI-4792 and that used for dielectrically neutral and dielectrically negative compounds is mixture ZLI-3086, both from Merck KGaA, Germany. The absolute values of the dielectric constants of the compounds are determined from the change in the respective values of the host mixture on addition of the compounds of interest. The values are extrapolated to a concentration of the compounds of interest of 100%.

Components having a nematic phase at the measurement temperature of 20° C. are measured as such, all others are treated like compounds.

The expression threshold voltage in the present application refers to the optical threshold and is quoted for 10% relative contrast ($V_{10}$), and the expression saturation voltage refers to the optical saturation and is quoted for 90% relative contrast ($V_{90}$), in both cases unless expressly stated otherwise. The capacitive threshold voltage ($V_0$), also called the Freedericks threshold ($V_{Fr}$), is only used if expressly mentioned.

The parameter ranges indicated in this application all include the limit values, unless expressly stated otherwise.

The different upper and lower limit values indicated for various ranges of properties in combination with one another give rise to additional preferred ranges.

Throughout this application, the following conditions and definitions apply, unless expressly stated otherwise. All concentrations are quoted in percent by weight and relate to the respective mixture as a whole, all temperatures are quoted in degrees Celsius and all temperature differences are quoted in differential degrees. All physical properties are determined in accordance with "Merck Liquid Crystals, Physical Properties of Liquid Crystals", Status November 1997, Merck KGaA, Germany, and are quoted for a temperature of 20° C., unless expressly stated otherwise. The optical anisotropy ($\Delta n$) is determined at a wavelength of 589.3 nm. The dielectric anisotropy ($\Delta \varepsilon$) is determined at a frequency of 1 kHz. The threshold voltages, as well as all other electro-optical properties, are determined using test cells produced at Merck KGaA, Germany. The test cells for the determination of $\Delta \varepsilon$ have a cell thickness of approximately 20 µm. The electrode is a circular ITO electrode having an area of 1.13 cm² and a guard ring. The orientation layers are SE-1211 from Nissan Chemicals, Japan, for homeotropic orientation ($\varepsilon_\parallel$) and polyimide AL-1054 from Japan Synthetic Rubber, Japan, for homogeneous orientation ($\varepsilon_\perp$). The capacitances are determined using a Solatron 1260 frequency response analyser using a sine wave with a voltage of 0.3 $V_{rms}$.

The light used in the electro-optical measurements is white light. A set-up using a commercially available DMS instrument from Autronic-Melchers, Germany, is used here. The characteristic voltages have been determined under perpendicular observation. The threshold ($V_{10}$), mid-grey ($V_{50}$) and saturation ($V_{90}$) voltages have been determined for 10%, 50% and 90% relative contrast, respectively.

The liquid-crystalline media are investigated with respect to their properties in the microwave frequency region as described in A. Penirschke et al., "Cavity Perturbation Method for Characterisation of Liquid Crystals up to 35 GHz", 34th European Microwave Conference —Amsterdam, pp. 545-548. Compare in this respect also A. Gaebler et al., "Direct Simulation of Material Permittivites . . . ", 12MTC 2009—International Instrumentation and Measurement Technology Conference, Singapore, 2009 (IEEE), pp. 463-467, and DE 10 2004 029 429 A, in which a measurement method is likewise described in detail.

The liquid crystal is introduced into a cylindrical polytetrafluoroethylene (PTFE) or quartz capillary. The capillary has an internal radius of 180 µm and an external radius of 350 µm. The effective length is 2.0 cm. The filled capillary is introduced into the centre of the cylindrical cavity with a resonance frequency of 19 GHz. This cavity has a length of 11.5 mm and a radius of 6 mm. The input signal (source) is then applied, and the result of the output signal is recorded using a commercial vector network analyser. For other frequencies, the dimensions of the cavity are adapted correspondingly.

The change in the resonance frequency and the Q factor between the measurement with the capillary filled with the liquid crystal and the measurement without the capillary filled with the liquid crystal is used to determine the dielectric constant and the loss angle at the corresponding target frequency by means of equations 10 and 11 of the above-mentioned publication A. Penirschke et al., "Cavity Perturbation Method for Characterisation of Liquid Crystals up to 35 GHz", 34th European Microwave Conference—Amsterdam, pp. 545-548, as described therein.

The values for the components of the properties perpendicular and parallel to the director of the liquid crystal are obtained by alignment of the liquid crystal in a magnetic field. To this end, the magnetic field of a permanent magnet is used. The strength of the magnetic field is 0.35 tesla. The alignment of the magnet is set correspondingly and then rotated correspondingly through 90°.

Preferred components are phase shifters, varactors, wireless and radio wave antenna arrays, matching circuit adaptive filters and others.

In the present application, the term compounds is taken to mean both one compound and a plurality of compounds, unless expressly stated otherwise.

The liquid-crystal media according to the invention preferably have nematic phases of in each case at least from −20° C. to 80° C., preferably from −30° C. to 85° C. and very particularly preferably from −40° C. to 100° C. The phase particularly preferably extends to 120° C. or more, preferably to 140° C. or more and very particularly preferably to 160° C. or more. The expression have a nematic phase here means on the one hand that no smectic phase and no crystallisation are observed at low temperatures at the corresponding temperature and on the other hand that no clearing occurs on heating from the nematic phase. The investigation at low temperatures is carried out in a flow viscometer at the corresponding temperature and checked by storage in test cells having a layer thickness of 5 µm for at least 100 hours. At high temperatures, the clearing point is measured in capillaries by conventional methods.

Furthermore, the liquid-crystal media according to the invention are characterised by high optical anisotropies in the visible region.

The $\Delta n$ of the liquid-crystal media in accordance with the present invention, at 589 nm (Na$^D$) and 20° C., is preferably in the range from 0.200 or more to 0.90 or less, more preferably in the range from 0.300 or more to 0.85 or less, even more preferably in the range from 0.400 or more to 0.800 or less.

In a preferred embodiment of the present invention, the liquid-crystal media employed have positive dielectric anisotropy ($\Delta \varepsilon$). This is preferably 1.8 or more and 15.0 or less, more preferably between 2.0 or more and 10.0 or less, particularly preferably between 3.0 or more and 8.0 or less and very particularly preferably between 3.5 or more and 6.0 or less.

In this preferred embodiment of the present invention, in which the liquid-crystal media employed have negative dielectric anisotropy ($\Delta \varepsilon$), the value thereof is preferably between 1.5 or more and 15.0 or less, particularly preferably between 1.8 or more and 12.0 or less and very particularly preferably between 2.0 or more and 10.0 or less.

Furthermore, the liquid-crystal media according to the invention are characterised by high anisotropies in the microwave region and/or millimetre wave region. The birefringence is, for example, preferably 0.14 or more, particularly preferably 0.15 or more, particularly preferably 0.20 or more, particularly preferably 0.25 or more and very particularly preferably 0.30 or more, at about 8.3 GHz. In addition, the birefringence is preferably 0.80 or less.

The liquid-crystal media in accordance with the present invention preferably have a clearing point of 90° C. or more, more preferably 100° C. or more, even more preferably 120° C. or more, particularly preferably 150° C. or more and very particularly preferably 170° C. or more.

The dielectric anisotropy in the microwave region is defined as $$\Delta\varepsilon_r \equiv (\varepsilon_{r,\parallel} - \varepsilon_{r,\perp}).$$

The tuneability ($\tau$) is defined as $$\tau \equiv (\Delta\varepsilon_r / \varepsilon_{r,\parallel}).$$

The material quality ($\eta$) is defined as $$\eta \equiv (\tau / \tan \delta_{\varepsilon_r,max}), \text{ where}$$

the maximum dielectric loss is $$\tan \delta_{\varepsilon_r,max.} \equiv \max.\{\tan \delta_{\varepsilon_r,\perp}; \tan \delta_{\varepsilon_r,\parallel}\}.$$

The material quality ($\eta$) of the preferred liquid-crystal materials is 6 or more, preferably 8 or more, preferably 10 or more, preferably 15 or more, preferably 17 or more, preferably 20 or more, particularly preferably 25 or more, very particularly preferably 30 and in particular 40 or more or even 50 or more, measured at 19 GHz.

In the corresponding components, the preferred liquid-crystal materials have phase shifter qualities of 15°/dB or more, preferably 20°/dB or more, preferably 30°/dB or more, preferably 40°/dB or more, preferably 50°/dB or more, particularly preferably 80°/dB or more and very particularly preferably 100°/dB or more, measured at 19 GHz.

In some embodiments, however, it is also possible to use liquid crystals having a negative value of the dielectric anisotropy.

The liquid crystals employed are either individual substances or mixtures. They preferably have a nematic phase.

The term "alkyl" preferably encompasses straight-chain and branched alkyl groups, as well as cycloalkyl groups, each having 1 to 15 carbon atoms, in particular the straight-chain groups methyl, ethyl, propyl, butyl, pentyl, hexyl and heptyl, as well as cyclopropyl and cyclohexyl. Groups having 2 to 10 carbon atoms are generally preferred.

The term "alkenyl" preferably encompasses straight-chain and branched alkenyl groups having 2 to 15 carbon atoms, in particular the straight-chain groups. Particularly preferred alkenyl groups are $C_2$- to $C_7$-1E-alkenyl, $C_4$- to $C_7$-3E-alkenyl, $C_5$- to $C_7$-4-alkenyl, $C_6$- to $C_7$-5-alkenyl and $C_7$-6-alkenyl, in particular $C_2$- to $C_7$-1E-alkenyl, $C_4$- to $C_7$-3E-alkenyl and $C_5$- to $C_7$-4-alkenyl. Examples of further preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably encompasses straight-chain groups having a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" or "alkoxyalkyl" preferably encompasses straight-chain radicals of the formula $C_nH_{2n+1}$—O—$(CH_2)_m$, in which n and m each, independently of one another, denote an integer from 1 to 10. Preferably, n here is 1 and m is 1 to 6.

Compounds containing a vinyl end group and compounds containing a methyl end group have low rotational viscosity.

In the present application, both high-frequency technology and hyper-frequency technology denote applications having frequencies in the range from 1 MHz to 100 THz, preferably from 1 GHz to 30 THz, more preferably 2 GHz to 10 THz, particularly preferably from about 5 GHz to 5 THz.

The liquid-crystal media in accordance with the present invention may comprise further additives and chiral dopants in the usual concentrations. The total concentration of these further constituents is in the range from 0% to 10%, preferably 0.1% to 6%, based on the mixture as a whole. The concentrations of the individual compounds used are each preferably in the range from 0.1% to 3%. The concentration of these and similar additives is not taken into consideration when quoting the values and concentration ranges of the liquid-crystal components and liquid-crystal compounds of the liquid-crystal media in this application.

The liquid-crystal media according to the invention consist of a plurality of compounds, preferably 3 to 30, more preferably 4 to 20 and very preferably 4 to 15 compounds. These compounds are mixed in a conventional manner. In general, the desired amount of the compound used in the smaller amount is dissolved in the compound used in the larger amount. If the temperature is above the clearing point of the compound used in the higher concentration, it is particularly easy to observe completion of the dissolution process. It is, however, also possible to prepare the media in other conventional ways, for example using so-called premixes, which can be, for example, homologous or eutectic mixtures of compounds, or using so-called "multibottle" systems, the constituents of which are themselves ready-to-use mixtures.

All temperatures, such as, for example, the melting point T(C,N) or T(C,S), the transition from the smectic (S) to the nematic (N) phase T(S,N) and the clearing point T(N,I) of the liquid crystals, are quoted in degrees Celsius. All temperature differences are quoted in differential degrees.

In the present invention and especially in the following examples, the structures of the mesogenic compounds are indicated by means of abbreviations, also referred to as acronyms. In these acronyms, the chemical formulae are abbreviated as follows using Tables A to C below. All groups $C_nH_{2n+1}$, $C_mH_{2m+1}$ and $C_lH_{2l+1}$ or $C_nH_{2n-1}$, $C_mH_{2m-1}$ and $C_lH_{2l-1}$ denote straight-chain alkyl or alkenyl, preferably 1E-alkenyl, having n, m and l C atoms respectively, where n, m and l, independently of one another, denote an integer from 1 to 9, preferably 1 to 7, or from 2 to 9, preferably 2 to 7, respectively. $C_oH_{2o+1}$ denotes straight-chain alkyl having 1 to 7, preferably 1 to 4, C atoms, or branched alkyl having 1 to 7, preferably 1 to 4, C atoms.

Table A lists the codes used for the ring elements of the core structures of the compounds, while Table C shows the linking groups. Table C gives the meanings of the codes for the left-hand or right-hand end groups. Table D shows illustrative structures of compounds with their respective abbreviations.

TABLE A
| Ring elements | |
|---|---|
|  | C |
| 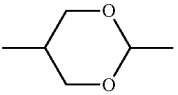 | D |
| 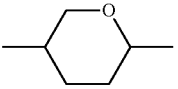 | A |
| 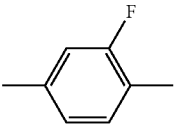 | G |
| 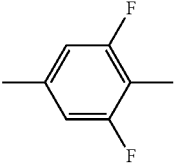 | U |
| 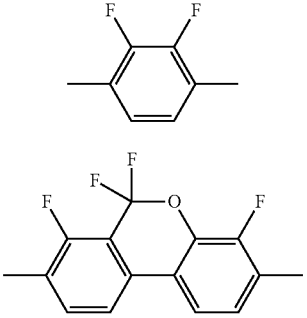 | Y |
| 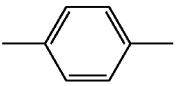 | fX |
| 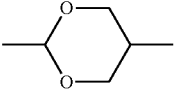 | P |
| 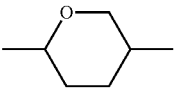 | DI |
| 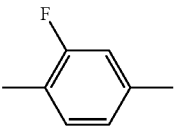 | AI |
| 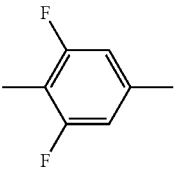 | GI |
| 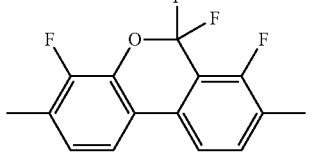 | UI |
TABLE A-continued
| Ring elements | |
|---|---|
| 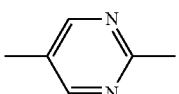 | fXI |
| 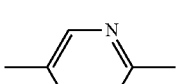 | M |
| 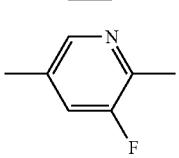 | N |
| 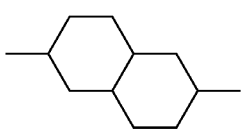 | fN |
| 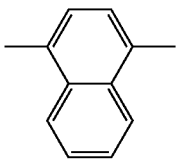 | dH |
| 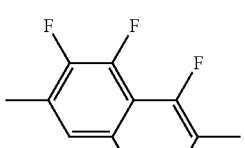 | N(1,4) |
| 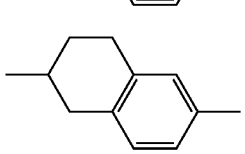 | N3f |
| 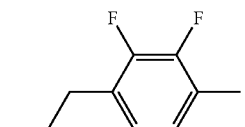 | tH |
| 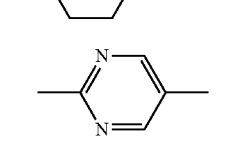 | tH2f |
| 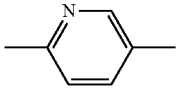 | MI |

TABLE A-continued

| Ring elements | |
|---|---|
| [pyridine with F] | fNI |
| [2,6-naphthalene] | N(2,6) |
| [trifluoronaphthalene] | N3fI |
| [tetrahydronaphthalene] | tHI |
| [difluoro-tetrahydronaphthalene] | tH2fI |
| [difluoro-methyl-indane] | K |
| [cyclohexene] | L |
| [fluoro-cyclohexene] | F |
| [2,5-dimethylphenyl-C$_o$H$_{2o+1}$] | P(o) |
| [isopropyl-phenyl] | P(i3) |
| [tert-butyl-phenyl] | P(t4) |
| [cyclopropyl-phenyl] | P(c3) |
| [cyclobutyl-phenyl] | P(c4) |
| [difluoro-methyl-indane] | KI |
| [cyclohexene] | LI |
| [fluoro-cyclohexene] | FI |
| [C$_o$H$_{2o+1}$-phenyl] | PI(o) |
| [isopropyl-phenyl] | PI(c3) |
| [tert-butyl-phenyl] | PI(t4) |
| [cyclopropyl-phenyl] | PI(c3) |

TABLE A-continued

Ring elements

| Structure | Label |
|---|---|
| (cyclobutyl-dimethylphenyl) | PI(c4) |
| (cyclopentyl-dimethylphenyl) | P(c5) |
| (cyclopentenyl-dimethylphenyl) | P(e5) |
| (cyclohexyl-dimethylphenyl) | P(c6) |
| (cyclohexenyl-dimethylphenyl) | P(e6) |
| F, (CH$_2$)$_o$H on dimethylphenyl; o ∈ {1;2;3;4;5;6} | GI(o) |
| F, isopropyl on dimethylphenyl | GI(i3) |
| F, tert-butyl on dimethylphenyl | GI(t4) |
| (cyclopentyl-dimethylphenyl) | PI(c5) |
| (cyclopentenyl-dimethylphenyl) | PI(e5) |
| (cyclohexyl-dimethylphenyl) | PI(c6) |
| (cyclohexenyl-dimethylphenyl) | PI(e6) |
| H(CH$_2$)$_o$, F on dimethylphenyl; o ∈ {1;2;3;4;5;6} | G(o) |
| isopropyl, F on dimethylphenyl | G(i3) |
| tert-butyl, F on dimethylphenyl | G(t4) |
| cyclopropyl, F on dimethylphenyl | GI(c3) |

TABLE A-continued

Ring elements

| | |
|---|---|
| GI(c4) | (structure: F-phenyl with cyclobutyl) |
| GI(c5) | (structure: F-phenyl with cyclopentyl) |
| GI(e5) | (structure: F-phenyl with cyclopentenyl) |
| GI(c6) | (structure: F-phenyl with cyclohexyl) |
| GI(e6) | (structure: F-phenyl with cyclohexenyl) |
| G(c3) | (structure: F-phenyl with cyclopropyl) |
| G(c4) | (structure: F-phenyl with cyclobutyl) |
| G(c5) | (structure: F-phenyl with cyclopentyl) |
| G(e5) | (structure: F-phenyl with cyclopentenyl) |
| G(c6) | (structure: F-phenyl with cyclohexyl) |
| G(e6) | (structure: F-phenyl with cyclohexenyl) |

TABLE B

Linking groups

| | | | |
|---|---|---|---|
| E | $-CH_2CH_2-$ | Z | $-CO-O-$ |
| V | $-CH=CH-$ | ZI | $-O-CO-$ |
| X | $-CF=CH-$ | O | $-CH_2-O-$ |
| XI | $-CH=CF-$ | OI | $-O-CH_2-$ |
| B | $-CF=CF-$ | Q | $-CF_2-O-$ |
| T | $-C\equiv C-$ | QI | $-O-CF_2-$ |
| W | $-CF_2CF_2-$ | | |

TABLE C

End groups

| Left-hand side | | Right-hand side | |
|---|---|---|---|
| Use alone | | | |
| -n- | $C_nH_{2n+1}-$ | -n | $-C_nH_{2n+1}$ |
| -nO- | $C_nH_{2n+1}-O-$ | -nO | $-O-C_nH_{2n+1}$ |
| -V- | $CH_2=CH-$ | -V | $-CH=CH_2$ |
| -nV- | $C_nH_{2n+1}-CH=CH-$ | -nV | $-C_nH_{2n}-CH=CH_2$ |

TABLE C-continued

| End groups | | | |
|---|---|---|---|
| Left-hand side | | Right-hand side | |
| -Vn- | $CH_2=CH-C_nH_{2n+1}-$ | -Vn | $-CH=CH-C_nH_{2n+1}$ |
| -nVm- | $C_nH_{2n+1}-CH=CH-C_mH_{2m}-$ | -nVm | $-C_nH_{2n}-CH=CH-C_mH_{2m+1}$ |
| -N- | $N\equiv C-$ | -N | $-C\equiv N$ |
| -S- | $S=C=N-$ | -S | $-N=C=S$ |
| -F- | $F-$ | -F | $-F$ |
| -CL- | $Cl-$ | -CL | $-Cl$ |
| -M- | $CFH_2-$ | -M | $-CFH_2$ |
| -D- | $CF_2H-$ | -D | $-CF_2H$ |
| -T- | $CF_3-$ | -T | $-CF_3$ |
| -MO- | $CFH_2O-$ | -OM | $-OCFH_2$ |
| -DO- | $CF_2HO-$ | -OD | $-OCF_2H$ |
| -TO- | $CF_3O-$ | -OT | $-OCF_3$ |
| -OXF- | $CF_2=CH-O-$ | -OXF | $-O-CH=CF_2$ |
| -A- | $H-C\equiv C-$ | -A | $-C\equiv C-H$ |
| -nA- | $C_nH_{2n+1}-C\equiv C-$ | -An | $-C\equiv C-C_nH_{2n+1}$ |
| -NA- | $N\equiv C-C\equiv C-$ | -AN | $-C\equiv C-C\equiv N$ |
| Use together with others | | | |
| -...A...- | $-C\equiv C-$ | -...A... | $-C\equiv C-$ |
| -...V...- | $CH=CH-$ | -...V... | $-CH=CH-$ |
| -...Z...- | $-CO-O-$ | -...Z... | $-CO-O-$ |
| -...ZI...- | $-O-CO-$ | -...ZI... | $-O-CO-$ |
| -...K...- | $-CO-$ | -...K... | $-CO-$ |
| -...W...- | $-CF=CF-$ | -...W... | $-CF=CF-$ | in which n and m each denote integers, and the three dots "..." are placeholders for other abbreviations from this table.

The following table shows illustrative structures together with their respective abbreviations. These are shown in order to illustrate the meaning of the rules for the abbreviations. They furthermore represent compounds which are preferably used.

Table D: Illustrative Structures

The illustrative structures show compounds which are particularly preferably employed.

Examples of Compounds of Component A

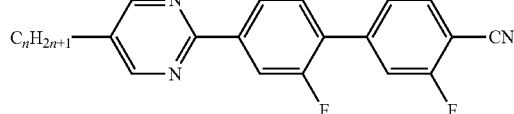

MUU-n-N

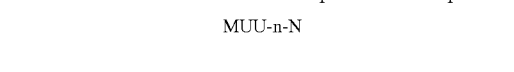

UMU-n-N

-continued

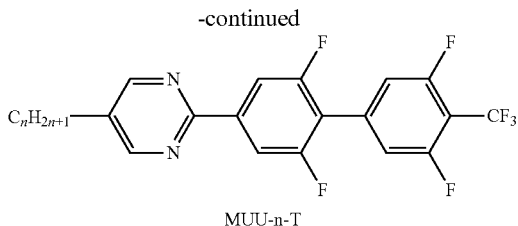

MUU-n-T

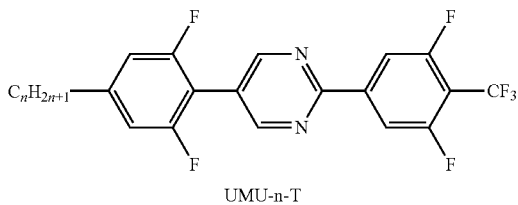

UMU-n-T

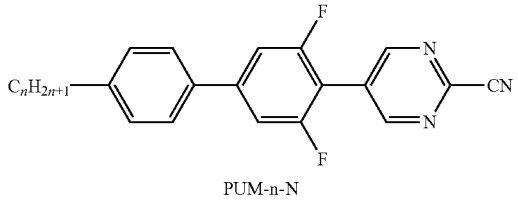

PUM-n-N

Examples of Compounds of Component B

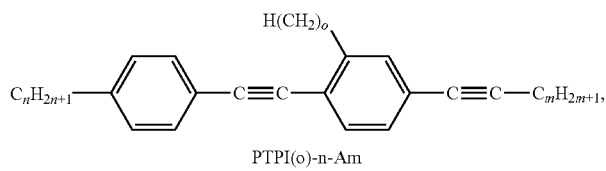

PTPI(o)-n-Am

-continued
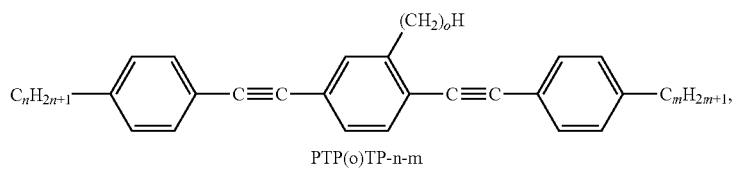
PTP(o)TP-n-m
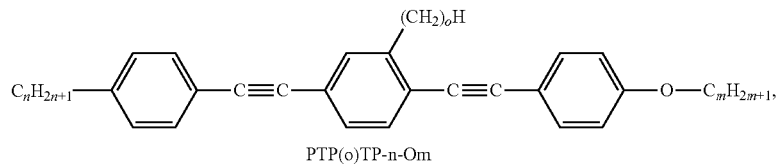
PTP(o)TP-n-Om
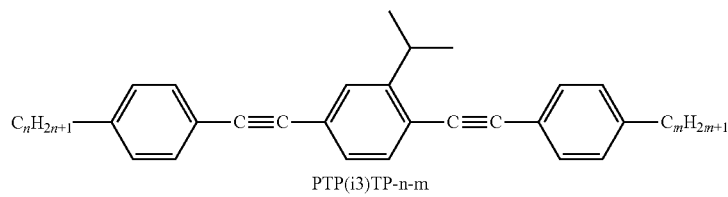
PTP(i3)TP-n-m
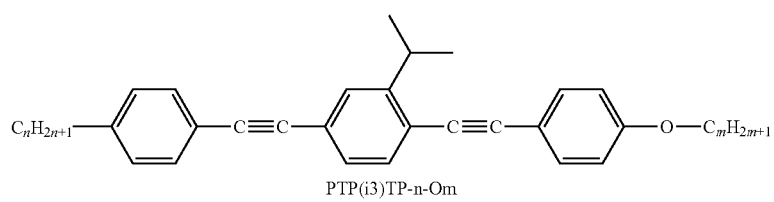
PTP(i3)TP-n-Om
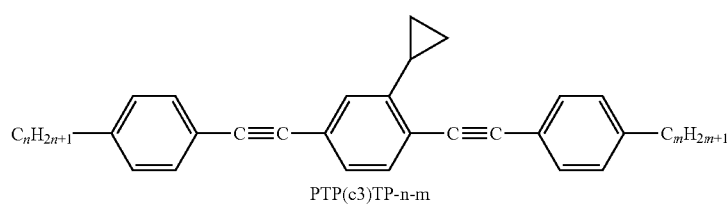
PTP(c3)TP-n-m
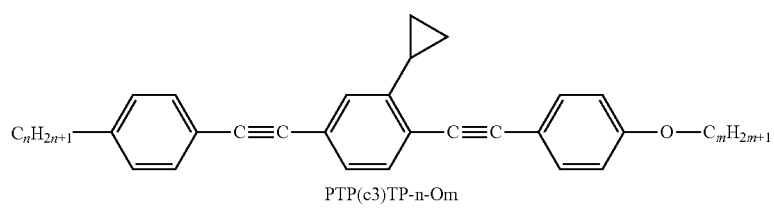
PTP(c3)TP-n-Om
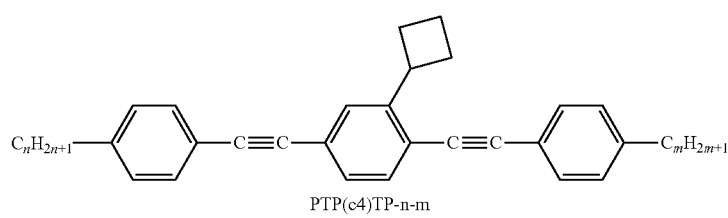
PTP(c4)TP-n-m
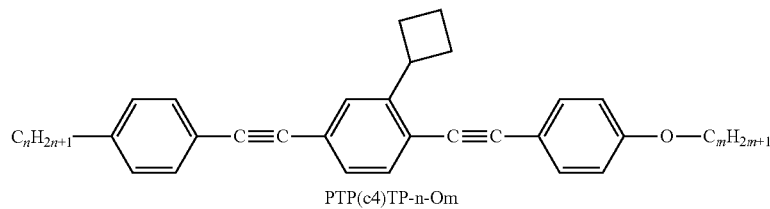
PTP(c4)TP-n-Om -continued
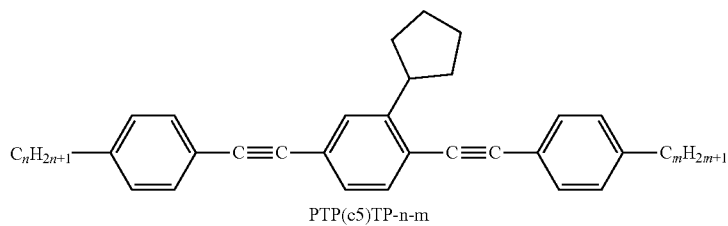
PTP(c5)TP-n-m
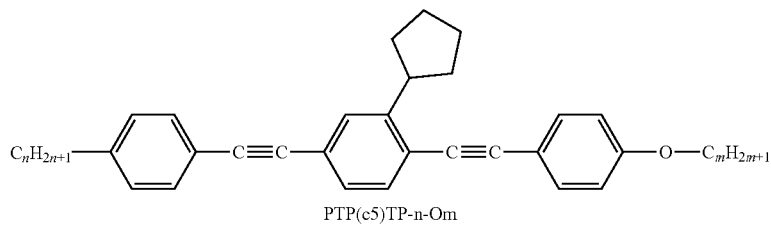
PTP(c5)TP-n-Om
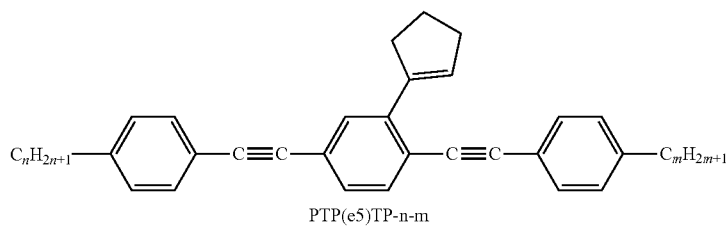
PTP(e5)TP-n-m
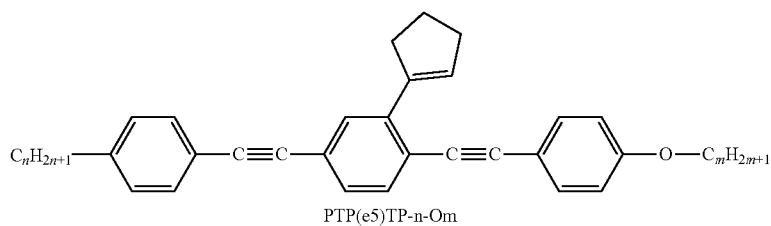
PTP(e5)TP-n-Om
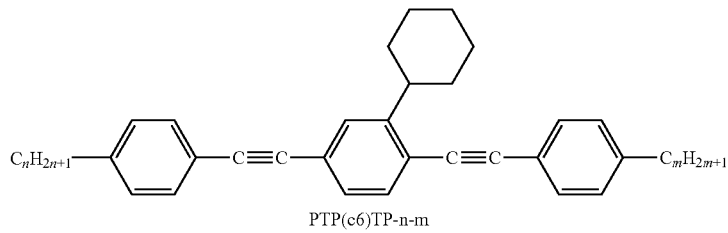
PTP(c6)TP-n-m
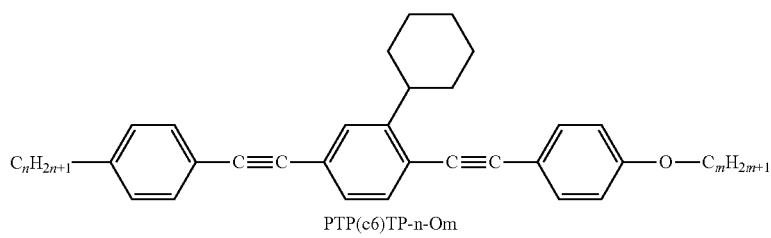
PTP(c6)TP-n-Om
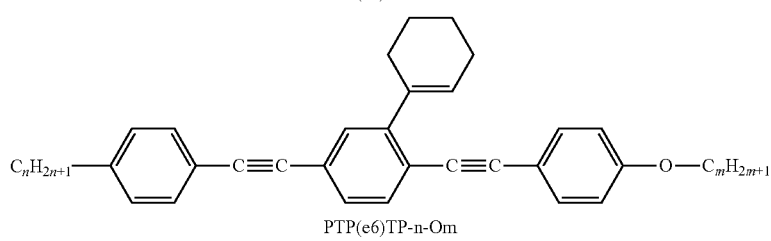
PTP(e6)TP-n-Om -continued
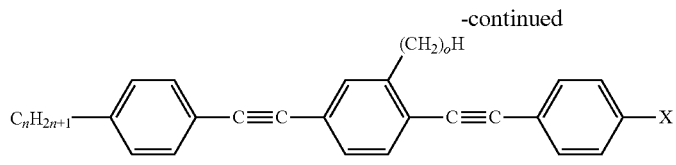
PTP(o)TP-n-X
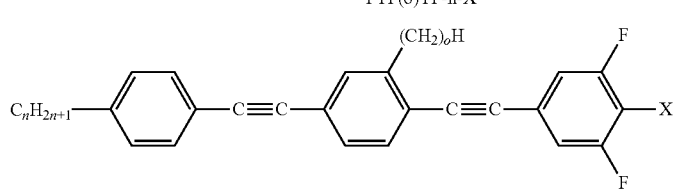
PTP(o)TU-n-X
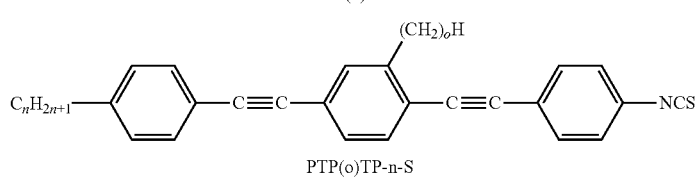
PTP(o)TP-n-S
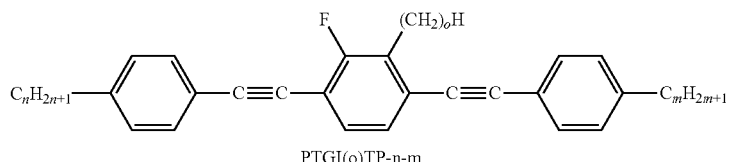
PTGI(o)TP-n-m
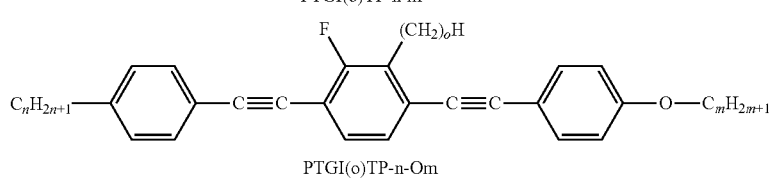
PTGI(o)TP-n-Om
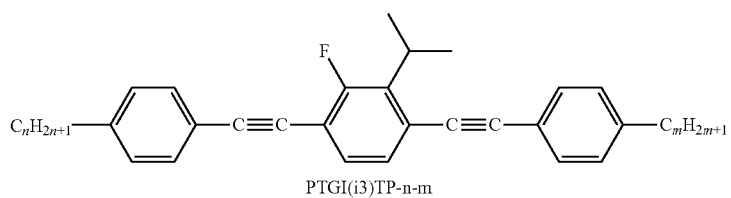
PTGI(i3)TP-n-m
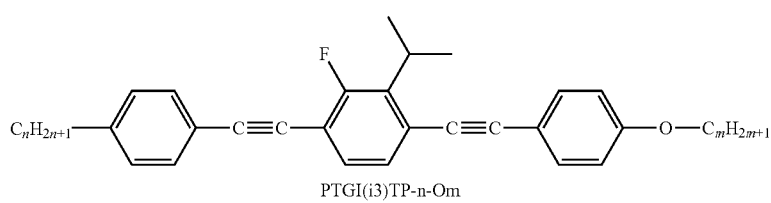
PTGI(i3)TP-n-Om
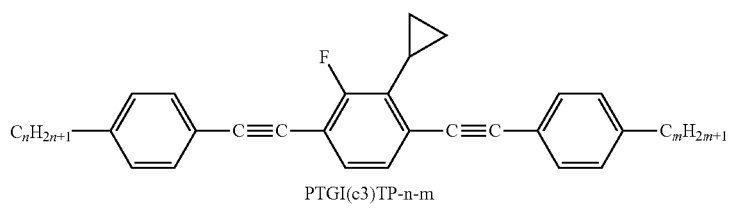
PTGI(c3)TP-n-m
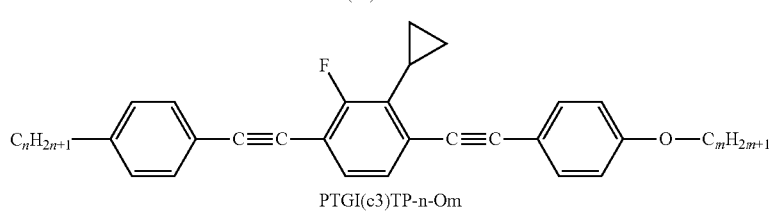
PTGI(c3)TP-n-Om

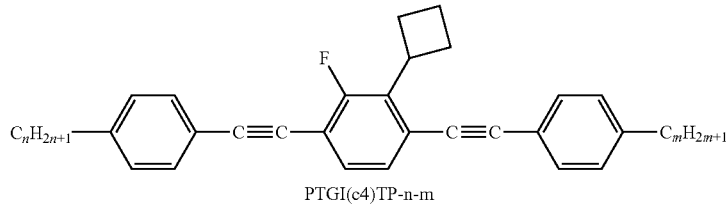
PTGI(c4)TP-n-m
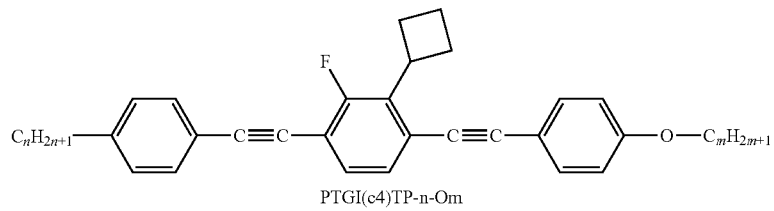
PTGI(c4)TP-n-Om
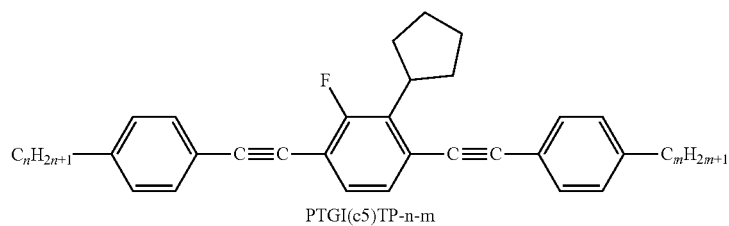
PTGI(c5)TP-n-m
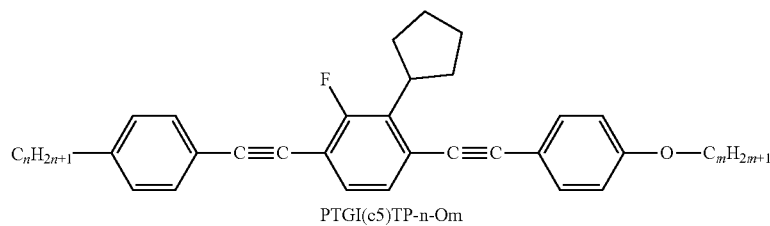
PTGI(c5)TP-n-Om
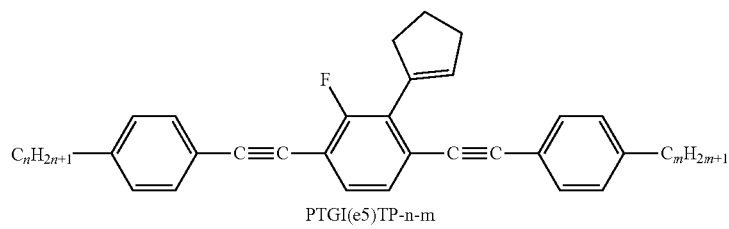
PTGI(e5)TP-n-m
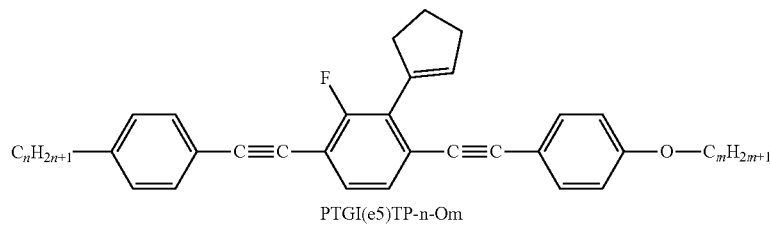
PTGI(e5)TP-n-Om
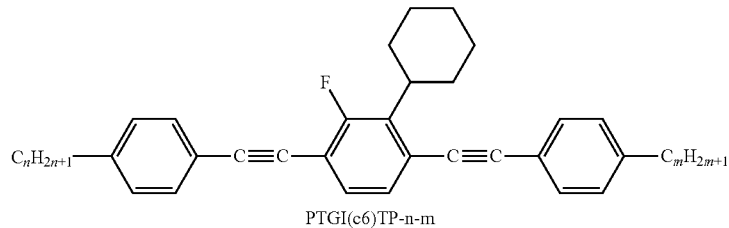
PTGI(c6)TP-n-m -continued
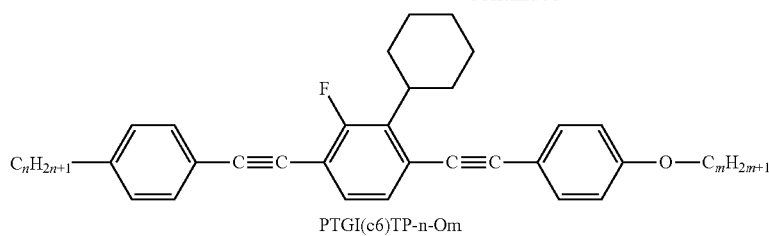
PTGI(c6)TP-n-Om
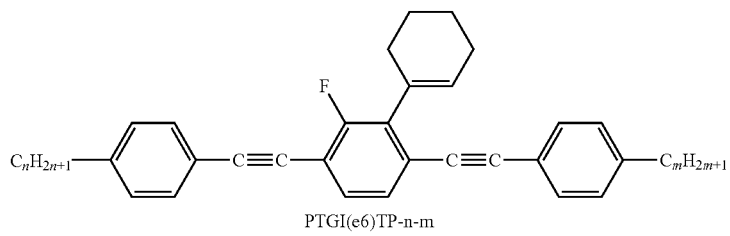
PTGI(e6)TP-n-m
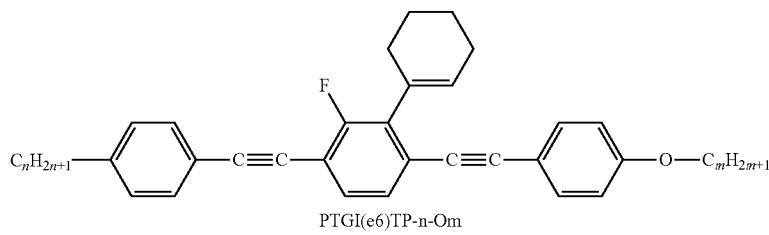
PTGI(e6)TP-n-Om
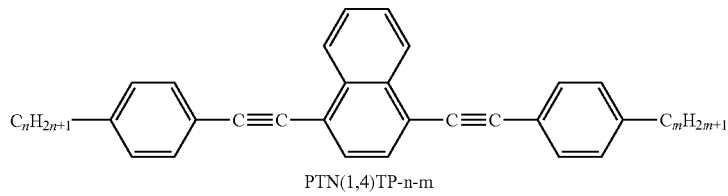
PTN(1,4)TP-n-m
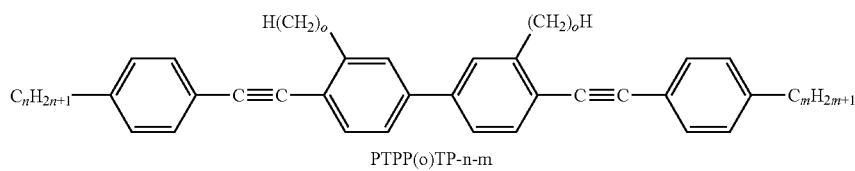
PTPP(o)TP-n-m
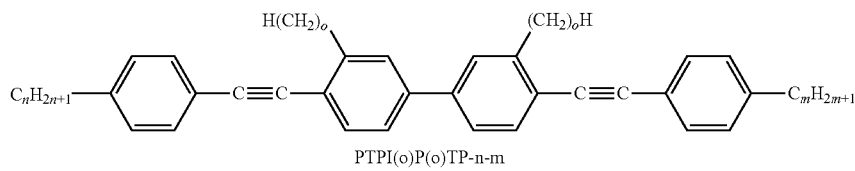
PTPI(o)P(o)TP-n-m
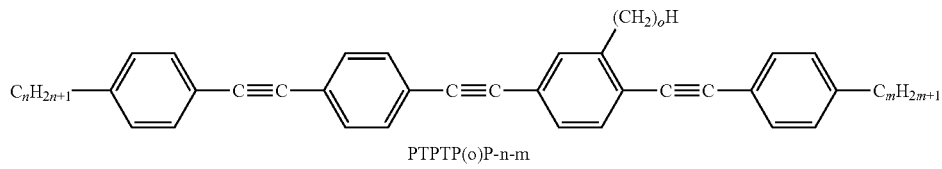
PTPTP(o)P-n-m
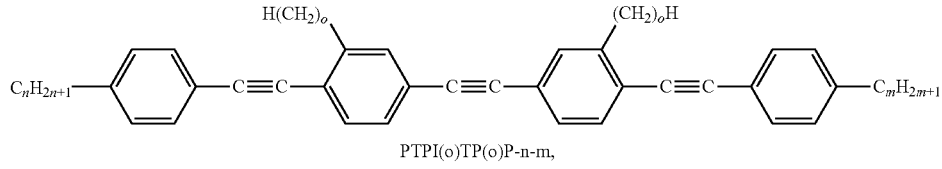
PTPI(o)TP(o)P-n-m,
X = F, Cl,
$o \in \{1;2;3;4;5;6\}$
($n \in \{1;2;3;4;5;6;7\}$ and $m \in \{1;2;3;4;5;6;7\}$)

Examples of Compounds of Component C
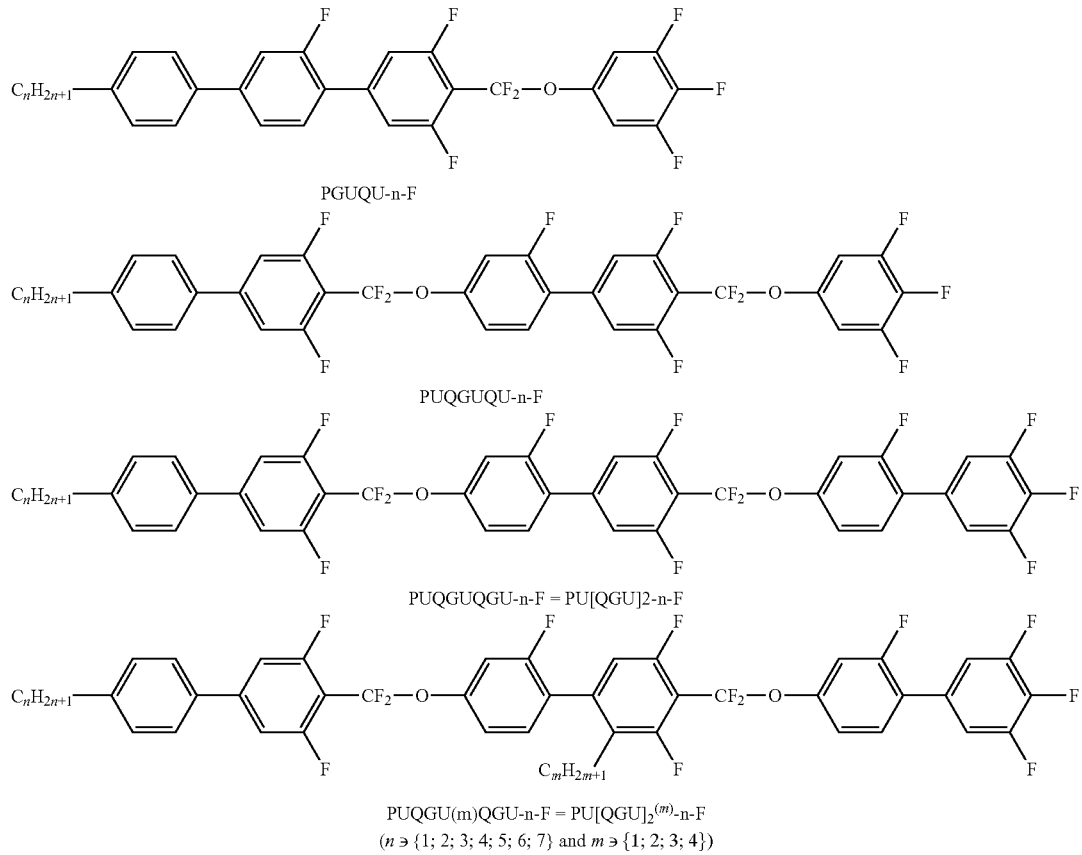
Examples of Compounds of Component D
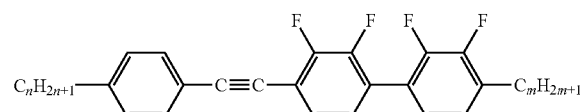
PTYY-n-m
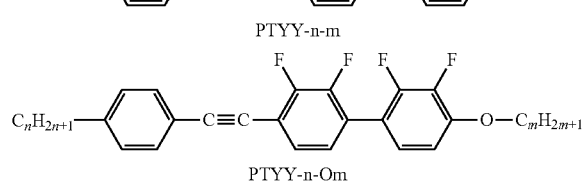
PTYY-n-Om
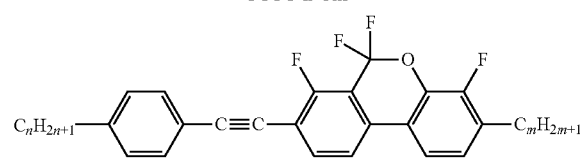
PfX-n-m
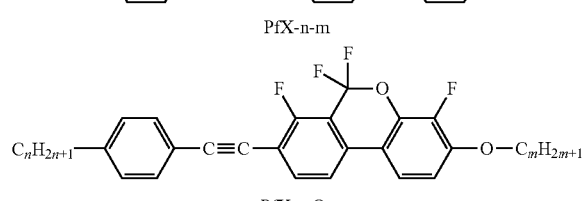
PfX-n-Om
($n \ni \{1;2;3;4;5;6;7\}$ and $m \ni \{1;2;3;4;5;6;7\}$)
Examples of Compounds of Component E
Compounds Having Three 6-Membered Rings
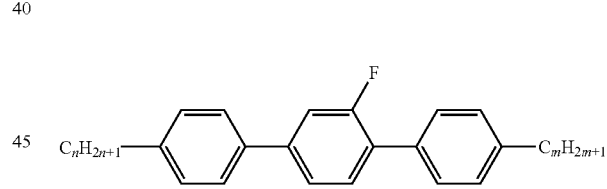
PGP-n-m
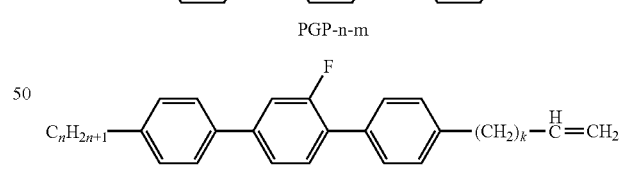
PGP-n-kV
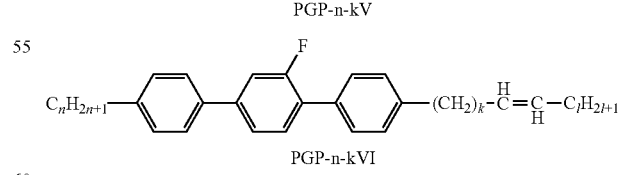
PGP-n-kVI
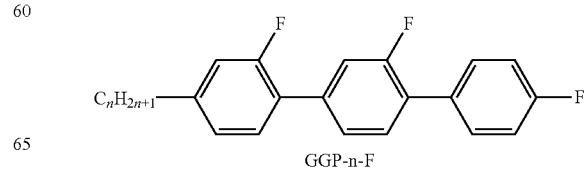
GGP-n-F -continued
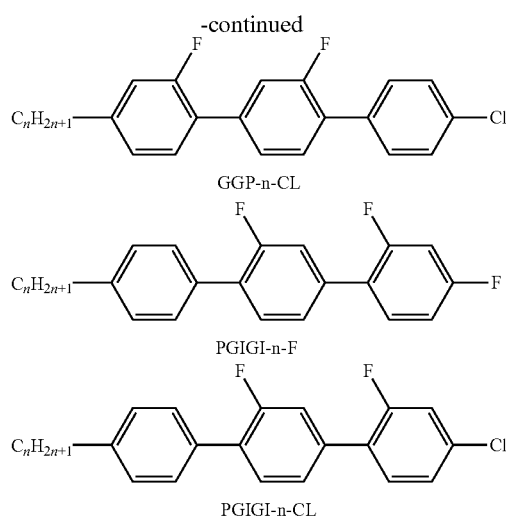
($n \ni \{1;2;3;4;5;6;7\}$, $m \ni \{1;2;3;4;5;6;7\}$, and $k \ni \{0;1;2;3;4\}$, preferably 0 or 2, and $l \ni \{1;2;3\}$)
Compounds Having Four 6-Membered Rings
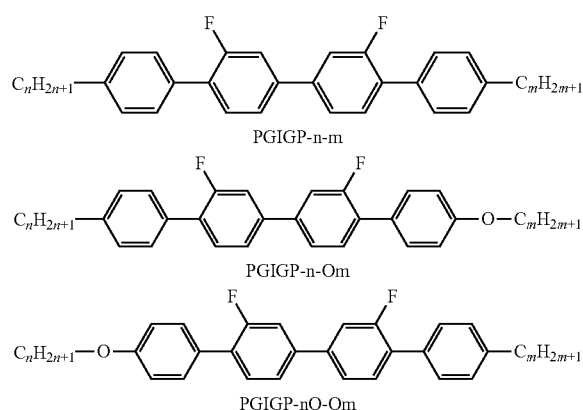
-continued
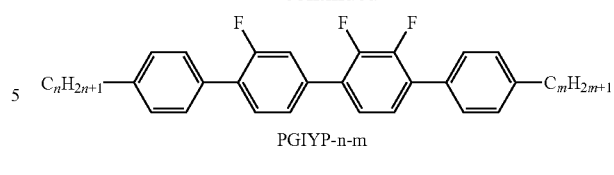
($n \ni \{1;2;3;4;5;6;7\}$ and $m \ni \{1;2;3;4;5;6;7\}$)
Illustrative Structures of Polar Compounds Employed:
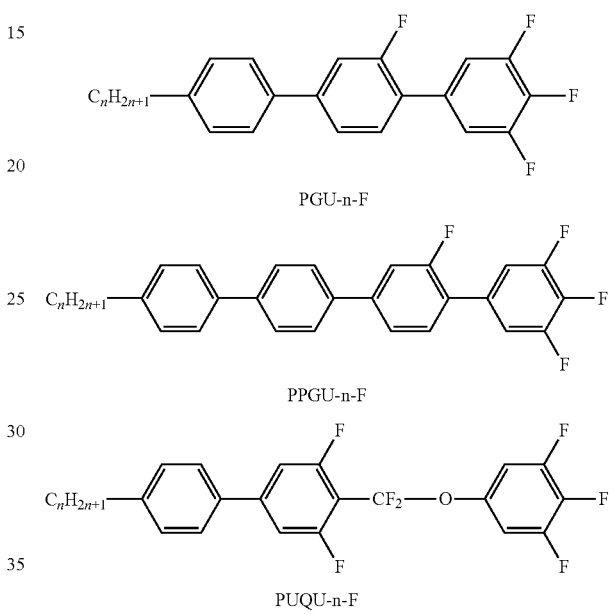
($n \ni \{1;2;3;4;5;6;7\}$)
Illustrative Structures of Further Neutral Compounds Preferably Employed:
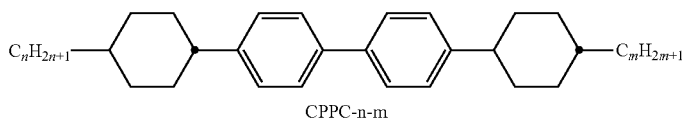
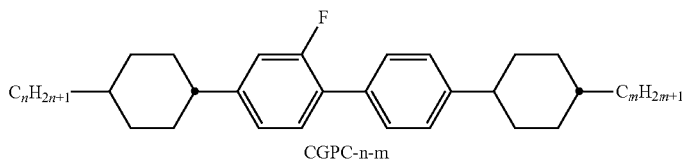
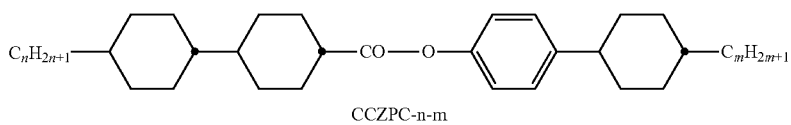
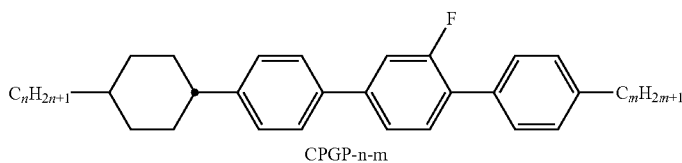

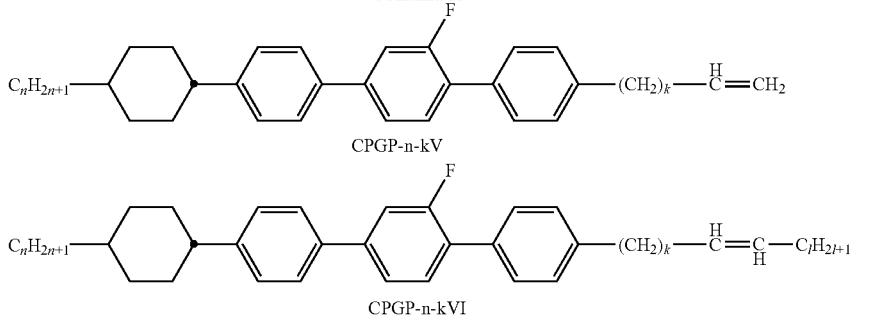
(n ∋ {1;2;3;4;5;6;7}, m ∋ {1;2;3;4;5;6;7}, and k ∋ {0;1;2;3;4}, preferably 0 or 2, and l ∋ {1;2;3})
Illustrative Structures of Further Compounds Employed:
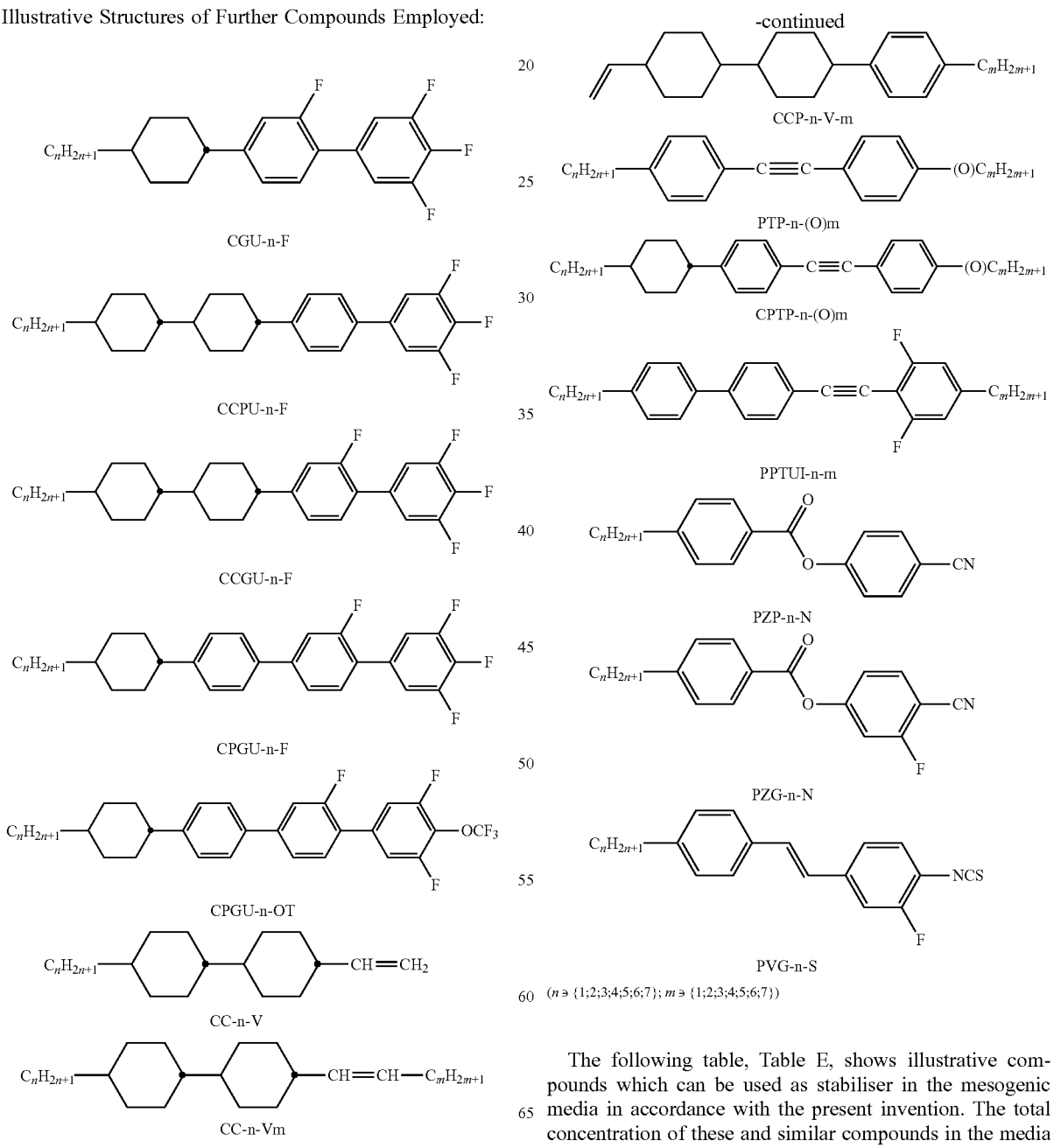
(n ∋ {1;2;3;4;5;6;7}; m ∋ {1;2;3;4;5;6;7})
The following table, Table E, shows illustrative compounds which can be used as stabiliser in the mesogenic media in accordance with the present invention. The total concentration of these and similar compounds in the media is preferably 5% or less.

TABLE E
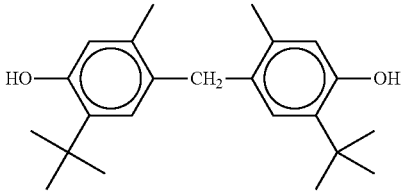
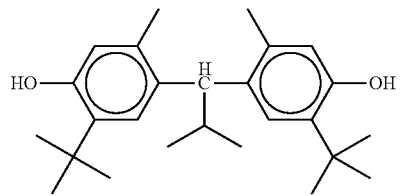
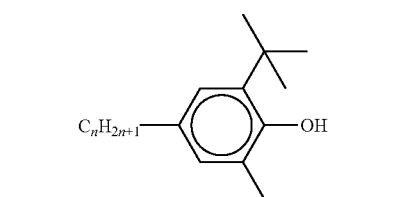
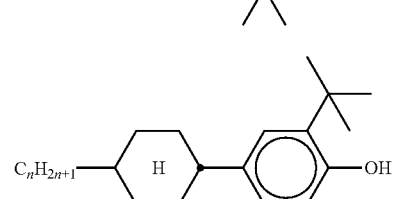
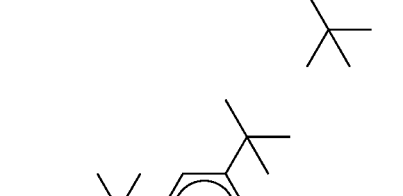
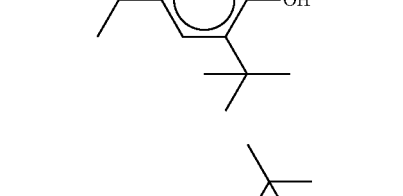
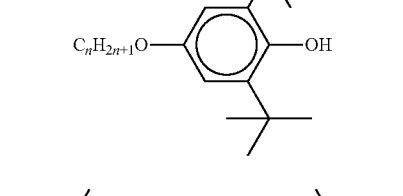
TABLE E-continued
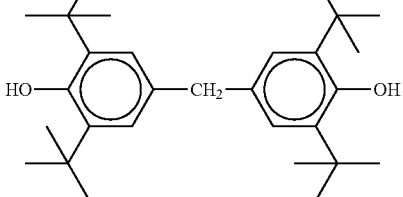
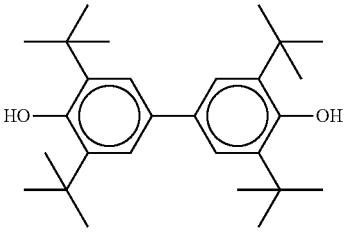
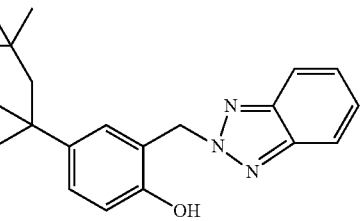
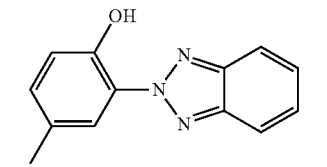 [SMILES: Cc1ccc(O)c(-n2nc3ccccc3n2)c1]
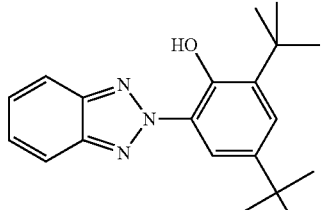
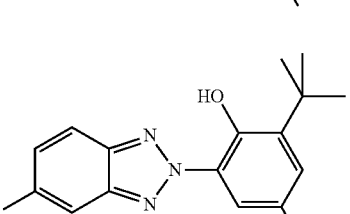

TABLE E-continued
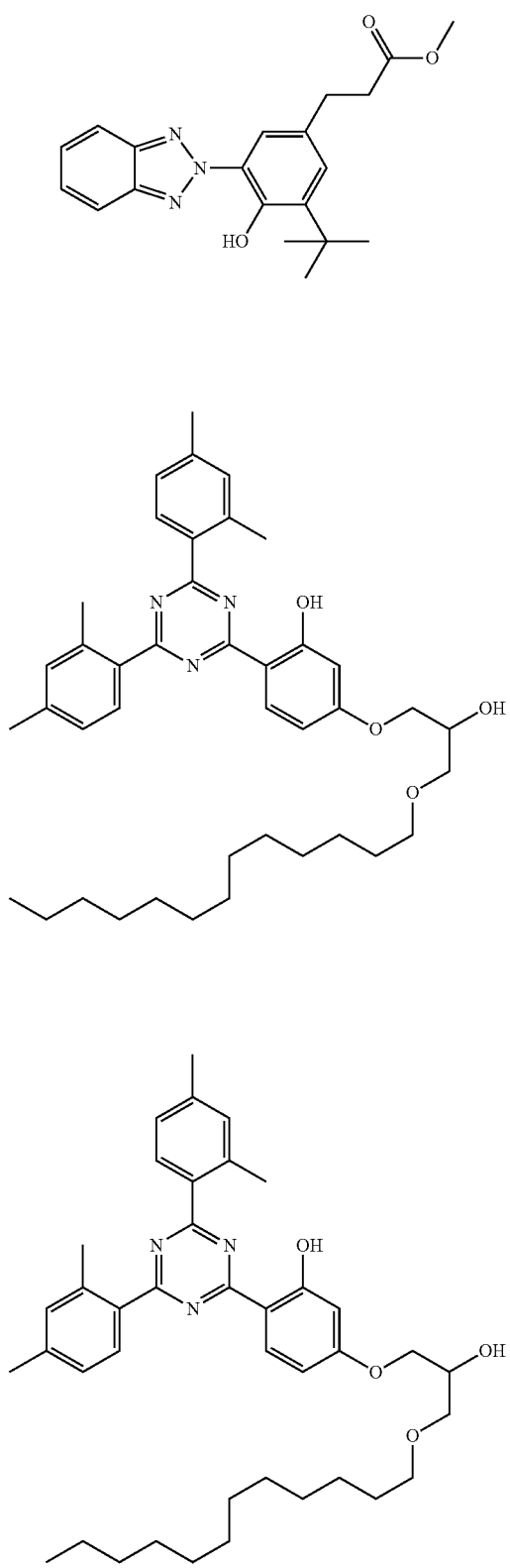
TABLE E-continued
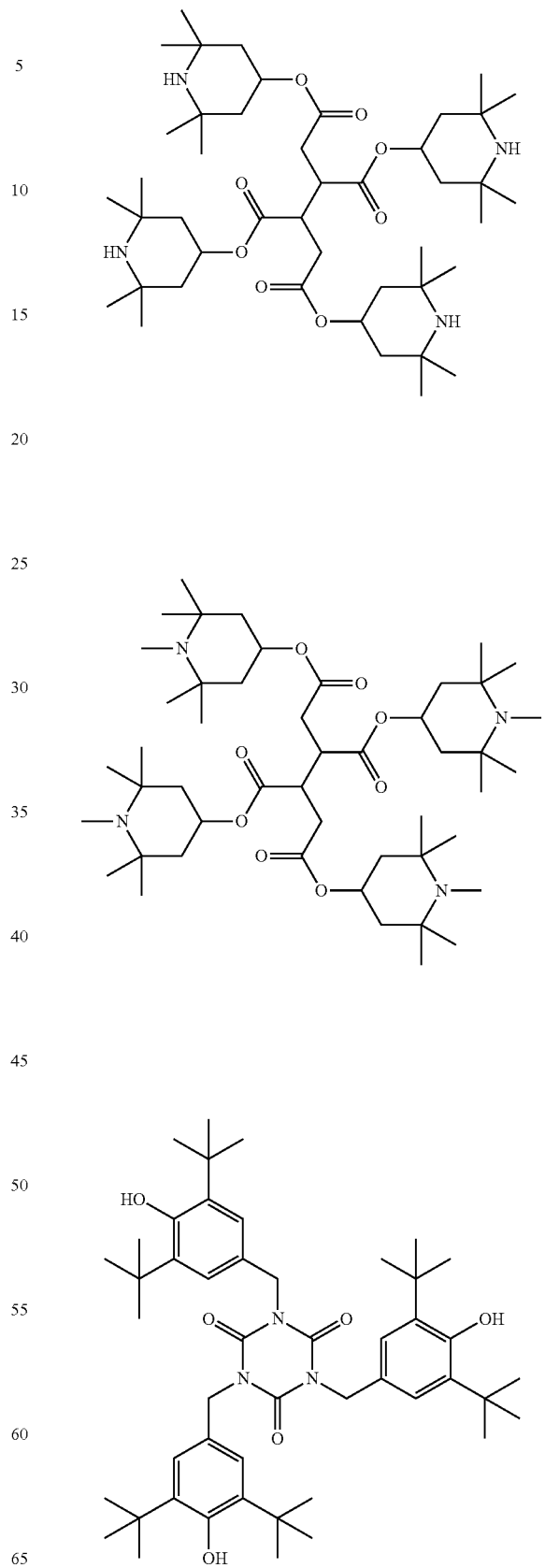

TABLE E-continued

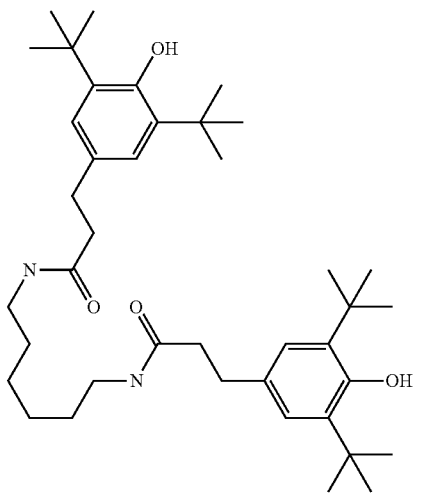 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]

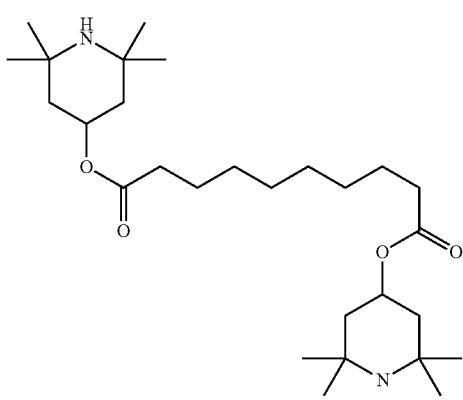

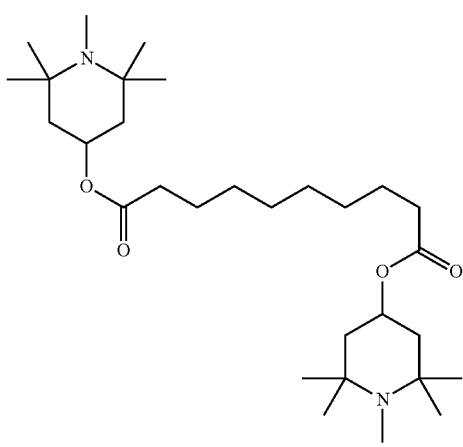

TABLE E-continued

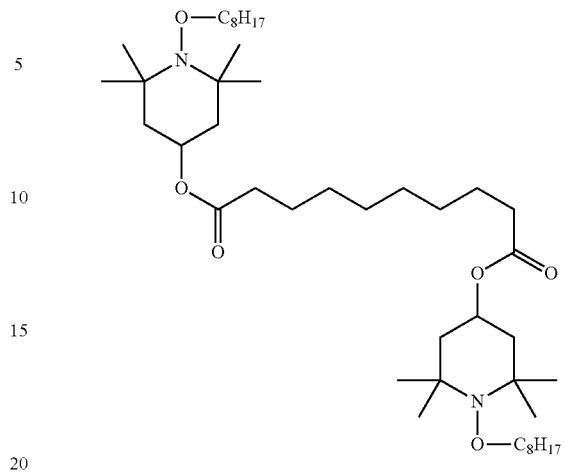

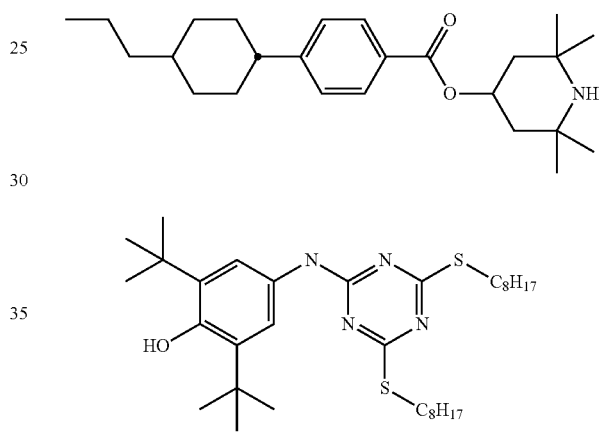

In a preferred embodiment of the present invention, the mesogenic media comprise one or more compounds selected from the group of the compounds from Table E.

The mesogenic media in accordance with the present application preferably comprise two or more, preferably four or more, compounds selected from the group consisting of the compounds from the above tables.

The liquid-crystal media in accordance with the present invention preferably comprise seven or more, preferably eight or more, compounds, preferably compounds having three or more, preferably four or more, different formulae, selected from the group of the compounds from Table D.

EXAMPLES

The following examples illustrate the present invention without limiting it in any way. However, it becomes clear to the person skilled in the art from the physical properties what properties can be achieved and in what ranges they can be modified. In particular, the combination of the various properties which can preferably be achieved is thus well defined for the person skilled in the art.

Synthesis Example S1

Step 1

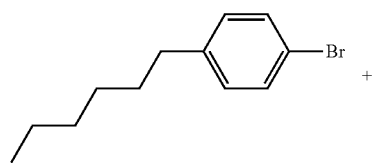

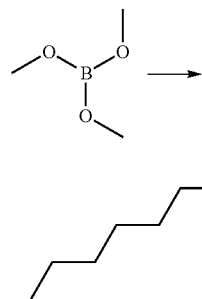

16.3 g (0.67 mol) magnesium turnings are placed in a round bottom flask under 90 ml THF and 70 ml of 1-brom-4-hexyl benzene (150 g, 0.622 mol) in 400 ml THF are added slowly. The reaction is started by addition of one drop of bromine. Once the reaction has started, the rest of the hexylbromide solution is added in such a way that the reaction is kept under reflux. After the addition is complete, the reaction is refluxed for 1 h, cooled to −25° C. and diluted with 100 ml THF. Then, 75 ml (0.67 mol) trimethylborate in 90 ml THF are added so that the temperature is kept between −25° C. and 0° C. Another 100 ml THF are added and the reaction is stirred 1 h at 0 to 5° C. Water is added and the mixture is acidified with hydrochloric acid. Extraction with MTB ether followed by evaporation of the solvent yields 4-hexylbenzene boronic acid as a colourless solid (purity 86% by HPLC).

Step 2

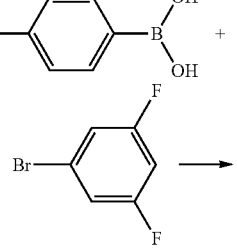

22.7 g (15 mmol) sodiumtetraborate-tetrahydrate are dissolved in 100 ml water and 1.4g (2 mmol) bis(triphenylphosphino)palladium(II)chloride and two drops of hydrazinium hydroxide are added. After 5 min, 25 g 4-hexylbenzene boronic acid of step 1 and 20.4 g 1-bromo-3,5-difluorobenzene (10 mmol) in 100 ml THF are added and the reaction is refluxed overnight. The solvent is evaporated and the residue is filtered with n-heptane through silica to give 1,3-difluoro-5-(4-hexylphenyl)benzene as colourless crystals.

Step 3

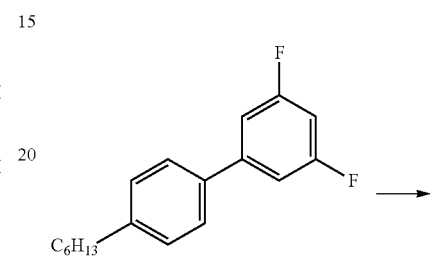

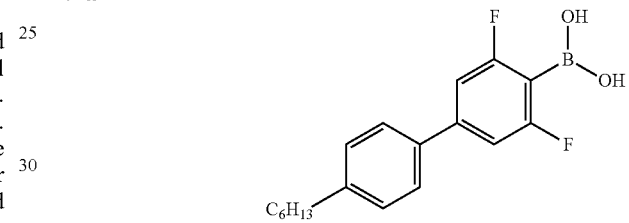

29.3 g 1,3-difluoro-5-(4-hexylphenyl)benzene are dissolved in 350 ml THF, cooled to −70° C. and 42 ml hexyllithium (30% in hexane, 0.104 mol) are added dropwise. The mixture is stirred at −65° C. for one hour and 15.4 ml (0.135 mol) in trimethylborate in 50 ml THF are added dropwise. After an additional hour, it is warmed to −10° C. and hydrolysed with conc. hydrochloric acid. The solution is washed with water, the solvent is removed i. vac. and the residue is treated with hot heptane, filtered off and dried, to give 2,6-difluoro-4-(4-hexylphenyl)benzene boronic acid as colourless solid.

Step 4

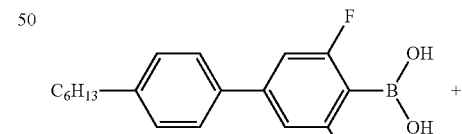

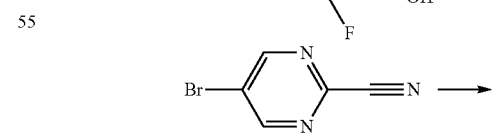

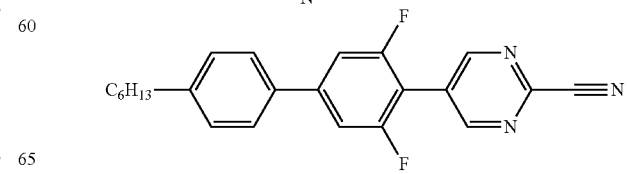

40 ml water, 4.4 g (52.2 mmol) sodium carbonate, 10 g (31 mmol) 2,6-difluoro-4-(4-hexylphenyl)benzene boronic acid and 4.8 g (26 mmol) 2-cyano-5-bromopyrimidine are dissolved in 80 ml THF under inert atmosphere and 27 mg bis(tert-butylphospino)palladium(0) (52 mmol) are added. The reaction is refluxed for 4 h and stirred at room temp. overnight. The solvent is removed i. vac. and the crude product is purified by column chromatography with toluene on silica. Crystallisation from isopropanol yields 5-[4-(4-hexylphenyl)-2,6-difluoro-phenyl]pyrimidine-2-carbonitrile (PUM-6-N) as colourless crystals.

In analogy to example S1, the following compounds are obtained:

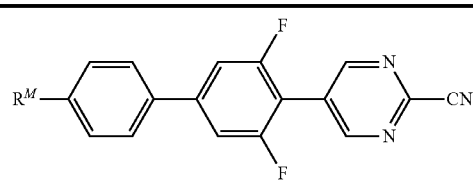

| Example | $R^M$ | Phase sequence | Δε | Δn | $\gamma_1$ |
|---|---|---|---|---|---|
| S1 | n-$C_6H_{13}$ | K 98 N 146.3 I | 55.0 | 0.2696 | 2080 |
| S2 | n-$C_3H_7$— | K 122 N 169.1 I | | | |
| S3 | n-$C_4H_9$ | K 118 N 152.6 I | 66.7 | 0.2815 | 1559 |
| S4 | n-$C_5H_{11}$ | K 118 N 155.6 I | 55.2 | 0.2875 | |
| S5 | $C_2H_5$— | | | | |
| S6 | n-$C_7H_{15}$ | | | | |
| S7 | $CH_2$=CH—$CH_2$ | | | | |
| S8 | $CH_2$=CH—$(CH_2)_2$— | | | | |
| S9 | $CH_2$=CH—$(CH_2)_3$— | | | | |
| S10 | $CH_2$=CH—$(CH_2)_4$— | | | | |
| S11 | $CH_2$=CH—$(CH_2)_5$— | | | | |
| S12 | E-$CH_3$—CH=CH—$CH_2$— | | | | |
| S13 | E-$CH_3$—CH=CH—$(CH_2)_2$— | | | | |
| S14 | E-$CH_3$—CH=CH—$(CH_2)_3$— | | | | |
| S15 | E-$CH_3$—CH=CH—$(CH_2)_4$— | | | | |

Use Examples

Comparative Example C-1 and Mixture Example M-1 are prepared and characterised as shown in the following tables.

Comparative Example C-1

| | Composition Compound | |
|---|---|---|
| No. | Abbreviation | c [%] |
| 1 | CCP-V-1 | 8.0 |
| 2 | PPTUI-3-2 | 8.0 |
| 3 | PPTUI-3-4 | 15.0 |
| 4 | PPTUI-4-4 | 30.0 |
| 5 | CPGP-5-2 | 3.0 |
| 6 | CPGP-5-3 | 3.0 |
| 7 | PTPI(1)-4-A1 | 29.0 |
| 8 | UMU-6-N | 4.0 |
| Σ | | 100.0 |

| Physical properties | |
|---|---|
| T(N, I) = | 122° C. |
| $n_e$ (20° C., 589.3 nm) > | 1.860 |
| $n_o$ (20° C., 589.3 nm) = | 1.5219 |
| Δε (20° C., 1 kHz) = | 3.8 |
| $\varepsilon_\parallel$ = | 6.7 |
| $\gamma_1$ (20° C.) = | 582 mPa · s |
| $K_1$ = | 13.8 |
| $K_3$ = | 24.2 |
| $V_0$ = | 2.00 V |

Mixture Example M-1

| | Composition Compound | |
|---|---|---|
| No. | Abbreviation | c [%] |
| 1 | CCP-V-1 | 8.0 |
| 2 | PPTUI-3-2 | 8.0 |
| 3 | PPTUI-3-4 | 15.0 |
| 4 | PPTUI-4-4 | 30.0 |
| 5 | CPGP-5-2 | 3.0 |
| 6 | CPGP-5-3 | 3.0 |
| 7 | PTPI(1)-4-A1 | 29.0 |
| 8 | PUM-6-N | 4.0 |
| Σ | | 100.0 |

| Physical properties | |
|---|---|
| T(N, I) = | 125° C. |
| $n_e$ (20° C., 589.3 nm) > | 1.860 |
| $n_o$ (20° C., 589.3 nm) = | 1.5220 |
| Δε (20° C., 1 kHz) = | 3.4 |
| $\varepsilon_\parallel$ = | 6.2 |
| $\gamma_1$ (20° C.) = | 561 mPa · s |
| $K_1$ = | 13.7 |
| $K_3$ = | 26.4 |
| $V_0$ = | 2.12 V |

TABLE 1

| Example | $\varepsilon_{r,\parallel}$ | tan $\delta_{\varepsilon\,r,\parallel}$ | $\varepsilon_{r,\perp}$ | tan $\delta_{\varepsilon\,r,\perp}$ | $\Delta\varepsilon_r$ | τ | η |
|---|---|---|---|---|---|---|---|
| C-1 | 3.12 | 0.0028 | 2.39 | 0.0098 | 0.73 | 0.234 | 24.0 |
| M-1 | 3.13 | 0.0030 | 2.40 | 0.0095 | 0.73 | 0.232 | 24.5 |

The comparison of Comparative Example C-1 and Mixture Example M-1 above shows that surprisingly, by using PUM-6-N instead of UMU-6-N a liquid-crystal mixture (M-1) with higher clearing temperature and lower rotational viscosity can be achieved. At the same M-1 has very similar excellent application properties with even an improved material η.

Mixture examples M-2 to M-6 are prepared and characterised as shown in the following tables.

Mixture Example M-2

| No. | Abbreviation | c [%] |
|---|---|---|
| | Composition Compound | |
| 1 | PPTUI-3-2 | 10.0 |
| 2 | PPTUI-3-4 | 16.0 |
| 3 | PPTUI-4-4 | 30.0 |
| 4 | CC-3-V | 9.0 |
| 5 | PTPI(1)-4-A1 | 30.0 |
| 6 | PUM-6-N | 5.0 |
| Σ | | 100.0 |

Physical properties $T(N, I)$ = 103° C.
$n_e$ (20° C., 589.3 nm) > 1.860
$n_o$ (20° C., 589.3 nm) = 1.5203
$\Delta\varepsilon$ (20° C., 1 kHz) = 3.9
$\varepsilon_\parallel$ = 6.7
$\gamma_1$ (20° C.) = 377 mPa·s
$K_1$ = 11.6
$K_3$ = 19.8
$V_0$ = 1.83 V

Mixture Example M-3

| No. | Abbreviation | c [%] |
|---|---|---|
| | Composition Compound | |
| 1 | CCP-V-1 | 7.0 |
| 2 | PPTUI-3-2 | 8.0 |
| 3 | PPTUI-3-4 | 15.0 |
| 4 | PPTUI-4-4 | 30.0 |
| 5 | CPGP-5-2 | 3.0 |
| 6 | CPGP-5-3 | 3.0 |
| 7 | PTPI(1)-4-A1 | 29.0 |
| 8 | PUM-6-N | 5.0 |
| Σ | | 100.0 |

Physical properties $T(N, I)$ = 125° C.
$n_e$ (20° C., 589.3 nm) > 1.860
$n_o$ (20° C., 589.3 nm) = 1.5221
$\Delta\varepsilon$ (20° C., 1 kHz) = 4.0
$\varepsilon_\parallel$ = 6.9
$\gamma_1$ (20° C.) = 565 mPa·s
$K_1$ = 13.8
$K_3$ = 23.2
$V_0$ = 1.96 V

Mixture Example M-4

| No. | Abbreviation | c [%] |
|---|---|---|
| | Composition Compound | |
| 1 | PPTUI-3-2 | 10.0 |
| 2 | PPTUI-3-4 | 16.0 |
| 3 | PPTUI-4-4 | 30.0 |
| 4 | CC-3-V | 10.0 |
| 5 | PTPI(1)-4-A1 | 30.0 |
| 6 | PUM-6-N | 4.0 |
| Σ | | 100.0% |

Physical properties $T(N, I)$ = 102° C.
$n_e$ (20° C., 589.3 nm) > 1.860
$n_o$ (20° C., 589.3 nm) = 1.5191
$\Delta\varepsilon$ (20° C., 1 kHz) = 3.3
$\varepsilon_\parallel$ = 6.1
$\gamma_1$ (20° C.) = 370 mPa·s
$K_1$ = 11.4
$K_3$ = 21.6
$V_0$ = 1.96 V

Mixture Example M-5

| No. | Abbreviation | c [%] |
|---|---|---|
| | Composition Compound | |
| 1 | PPTUI-3-2 | 10.0 |
| 2 | PPTUI-3-4 | 17.0 |
| 3 | PPTUI-4-4 | 30.0 |
| 4 | CC-4-V | 10.0 |
| 5 | PTPI(1)-4-A1 | 30.0 |
| 6 | PUM-6-N | 3.0 |
| Σ | | 100.0% |

Physical properties $T(N, I)$ = 102.5° C.
$n_e$ (20° C., 589.3 nm) > 1.860
$n_o$ (20° C., 589.3 nm) = 1.5200
$\Delta\varepsilon$ (20° C., 1 kHz) = 2.7
$\varepsilon_\parallel$ = 5.4
$\gamma_1$ (20° C.) = 386 mPa·s
$K_1$ = 11.2
$K_3$ = 21.9
$V_0$ = 2.16 V

Mixture Example M-6

| No. | Abbreviation | c [%] |
|---|---|---|
| | Composition Compound | |
| 1 | PPTUI-3-2 | 10.0 |
| 2 | PPTUI-3-4 | 16.0 |
| 3 | PPTUI-4-4 | 30.0 |
| 4 | CCP-V-1 | 10.0 |
| 5 | PTPI(1)-4-A1 | 30.0 |
| 6 | PUM-6-N | 4.0 |
| Σ | | 100.0% |

Physical properties $T(N, I)$ = 115° C.
$n_e$ (20° C., 589.3 nm) > 1.860
$n_o$ (20° C., 589.3 nm) = 1.5225
$\Delta\varepsilon$ (20° C., 1 kHz) = 3.4
$\varepsilon_\parallel$ = 6.2
$\gamma_1$ (20° C.) = 498 mPa·s
$K_1$ = 12.3

-continued

| | |
|---|---|
| K₃ = | 23.7 |
| V₀ = | 2.01 V |

TABLE 2

| Example | $\varepsilon_{r,\parallel}$ | $\tan \delta_{\varepsilon, r, \parallel}$ | $\varepsilon_{r,\perp}$ | $\tan \delta_{\varepsilon, r, \perp}$ | $\Delta\varepsilon_r$ | $\tau$ | $\eta$ |
|---|---|---|---|---|---|---|---|
| M-2 | 3.09 | 0.0032 | 2.40 | 0.0103 | 0.69 | 0.225 | 21.9 |
| M-3 | 3.14 | 0.0030 | 2.40 | 0.0093 | 0.74 | 0.236 | 25.4 |
| M-4 | 3.09 | 0.0032 | 2.40 | 0.0100 | 0.69 | 0.223 | 22.4 |
| M-5 | 3.10 | 0.0032 | 2.41 | 0.0099 | 0.69 | 0.223 | 22.6 |
| M-6 | 3.12 | 0.0030 | 2.40 | 0.0099 | 0.72 | 0.232 | 23.4 |

As shown in Table 2, the mixtures containing PUM-n-N do all show high material qualities (η) and low loss (τ) which makes them very well suitable for applications in the microwave region and/or millimetre wave region, in particular for phase shifters.

The invention claimed is:
1. A liquid crystal medium comprising one or more compounds of formula M

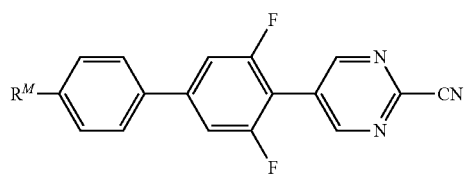

wherein
$R^M$ denotes alkyl or alkenyl having 1 to 7 C atoms,
one or more compounds of formula IA

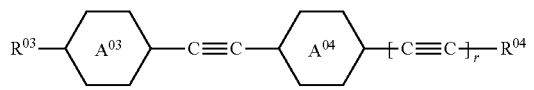

wherein
r denotes 0 or 1,

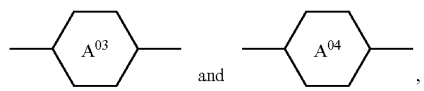

independently of one another, denote

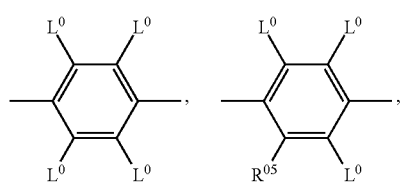

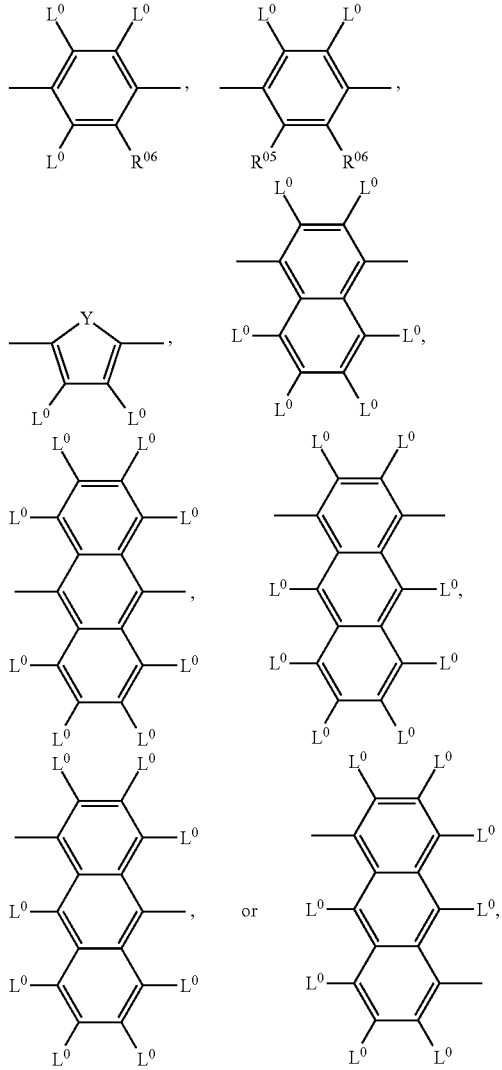

wherein
Y denotes S or O and wherein in the 1,4-phenylene groups, one C—H group or a plurality of CH groups, may be replaced by N, and
$L^0$ on each occurrence, independently of one another, denotes H, Br, Cl, F, —CN, —NCS, —SCN, SF₅, $C_1$-$C_{10}$ alkyl, C1-$C_{10}$ alkoxy, $C_3$-$C_6$ cycloalkyl or a mono- or polyfluorinated $C_1$-$C_{10}$ alkyl or alkoxy group,
$R^{03}$, $R^{04}$ each, independently of one another, denote a halogenated or unsubstituted alkyl radical having 1 to 15 C atoms, where, in addition, one or more $CH_2$ groups in these radicals may each be replaced, independently of one another, by —C≡C—, —CH=CH—, —CF=CF—, —CF=CH—, —CH=CF—, —C(O)O—, —OC(O)—, —C(O)—, —O— or —S— in such a way that O or S atoms are not linked directly to one another and, optionally, independently of one another, $R^{03}$ may also denote ethynyl (i.e. —C≡CH) and $R^{04}$ may also denote H, and
$R^{05}$ and $R^{06}$ each, independently of one another, denote a halogenated or unsubstituted alkyl radical having 1 to 6 C atoms, where, in addition, one or more $CH_2$ groups in these radicals may each be replaced, independently of one another, by —C≡C—, —CH=CH—, —CF=CF—, —CF=CH—, —CH=CF—, —C(O)O—, —OC(O)—, —C(O)—, —O— or —S— in such a way that O or S atoms are not linked directly to one another, and one or more compounds of formula VI

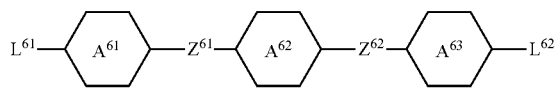

VI in which

L61 denotes $R^{61}$ and, in the case where $Z^{61}$ and/or $Z^{62}$ denote trans-CH=CH— or trans-CF=CF—, alternatively also denotes $X^{61}$, L62 denotes $R^{62}$ and, in the case where $Z^{61}$ and/or $Z^{62}$ denote trans-CH=CH— or trans-CF=CF—, alternatively also denotes $X^{62}$, $R^{61}$ and $R^{62}$, independently of one another, denote H, unfluorinated alkyl or unfluorinated alkoxy having 1 to 17 C atoms or un-fluorinated alkenyl, unfluorinated alkenyloxy or unfluorinated alkoxyalkyl having 2 to 15 C atoms, $X^{61}$ and $X^{62}$, independently of one another, denote F or Cl, —CN, —NCS, —SF$_5$, fluorinated alkyl or alkoxy having 1 to 7 C atoms or fluorinated alkenyl, alkenyloxy or alkoxyalkyl having 2 to 7 C atoms, or —NCS, one of $Z^{61}$ and $Z^{62}$ denotes trans-CH=CH—, trans-CF=CF— or —C≡C— and the other, independently thereof, denotes trans-CH=CH—, trans-CF=CF— or a single bond, and

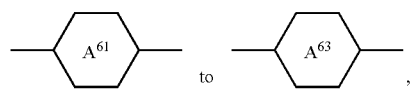

independently of one another, denote

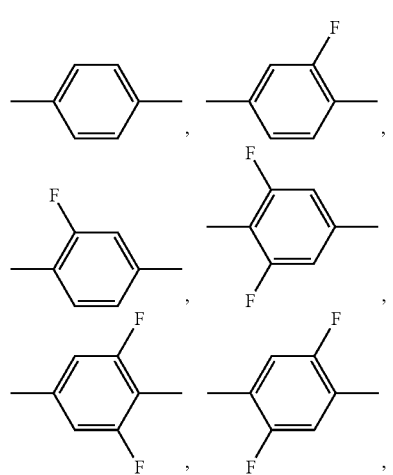

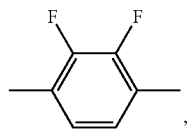

said liquid crystalline medium having a birefringence of 0.200 to 0.90.

2. The liquid crystal medium according to claim 1, wherein one or more compounds of formula IA are compounds of formulae IA-1 to IA-7

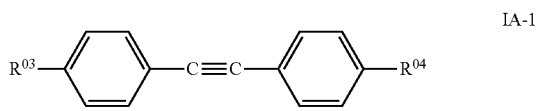
IA-1

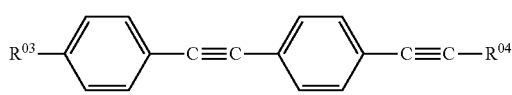
IA-2

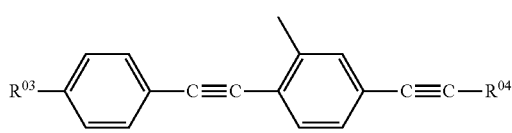
IA-3

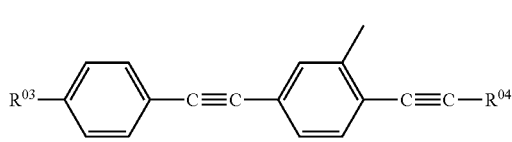
IA-4

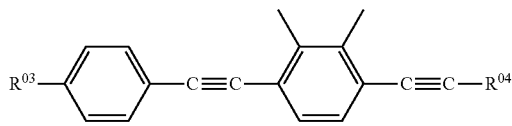
IA-5

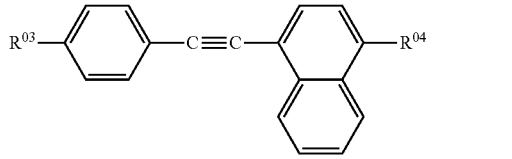
IA-6

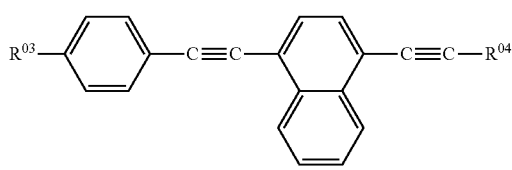
IA-7 wherein $R^{03}$ and $R^{04}$ denote alkyl having 1 to 7 C atoms.

3. The liquid crystal medium according to claim 1, comprising one or more compounds of formula I

I wherein

denotes

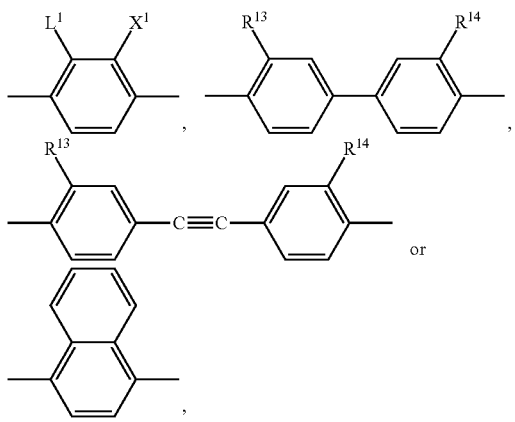

,

L¹ denotes H, alkyl having 1 to 6 C atoms, cycloalkyl having 3 to 6 C atoms or cycloalkenyl having 4 to 6 C atoms, X¹ denotes H or alkyl having 1 to 3 C atoms or halogen, $R^{11}$ to $R^{14}$ independently of one another, denote unfluorinated alkyl or unfluorinated alkoxy, each having 1 to 15 C atoms, unfluorinated alkenyl, unfluorinated alkenyloxy or unfluorinated alkoxyalkyl, each having 2 to 15 C atoms, or cycloalkyl, alkylcycloalkyl, cycloalkenyl, alkylcycloalkenyl, alkylcycloalkylalkyl or alkylcycloalkenylalkyl, each having up to 15 C atoms, and alternatively one of $R^{13}$ and $R^{14}$ or both also denote H.

4. The liquid crystal medium according to claim 1, wherein one or more compounds of formula VI are compounds of the formula VI-1a VI-1a

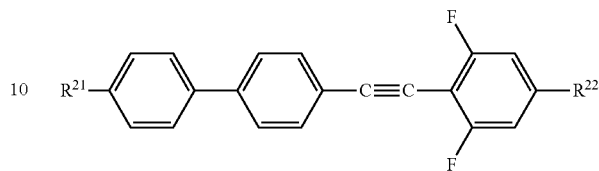

wherein $R^{21}$ and $R^{22}$ have the meaning indicated in claim 1.

5. The liquid crystal medium according to claim 1, additionally comprising one or more of the following components, components C to F:

a strongly dielectrically positive component, component C, which has a dielectric anisotropy of 10 or more at a temperature of 20° C. and a frequency of 1 kHz, a strongly dielectrically negative component, component D, which has a dielectric anisotropy of −5 or less at a temperature of 20° C. and a frequency of 1 kHz, a component, component E, which consists of compounds having seven or more five- or six-membered rings and has a dielectric anisotropy in the range from more than −5.0 to less than 10.0 at a temperature of 20° C. and a frequency of 1 kHz, and/or a component, component F, which and consists of compounds having up to six five- or six-membered rings and also has a dielectric anisotropy in the range from more than −5.0 to less than 10.0 at a temperature of 20° C. and a frequency of 1 kHz.

6. A process for the preparation of a liquid-crystal medium according to claim 1, comprising mixing one or more compounds of formula M with one or more further compounds and/or with one or more additives.

7. A high-frequency technology component, that is a phase shifter, varactor, wireless or radio wave antenna array, or matching circuit adaptive filter, comprising in said component a liquid-crystal medium according to claim 1.

8. A microwave antenna array, comprising in said array a liquid-crystal medium according to claim 1.

* * * * *